United States Patent [19]

Nagata et al.

[11] Patent Number: 5,225,422

[45] Date of Patent: Jul. 6, 1993

[54] PYRIDINE COMPOUNDS WHICH ARE USEFUL AS LEUKOTRIENE B4 ANTAGONIST

[75] Inventors: Hideo Nagata, Ibaraki; Hajime Kawakami, Nishinomiya, both of Japan

[73] Assignee: Sumitomo Pharmaceuticals Co., Ltd., Osaka, Japan

[21] Appl. No.: 891,256

[22] Filed: Jun. 1, 1992

[30] Foreign Application Priority Data

May 31, 1991 [JP] Japan ................... 3-157725

[51] Int. Cl.$^5$ ..................... A61K 31/44; C07D 213/55
[52] U.S. Cl. .................... 514/354; 546/316; 546/323; 514/355
[58] Field of Search ............... 546/323, 316; 514/354, 514/355

[56] References Cited

U.S. PATENT DOCUMENTS 4,663,332 5/1987 Carson et al. .................. 514/340
4,672,066 6/1987 Carson et al. .................. 514/256

FOREIGN PATENT DOCUMENTS 276065 7/1988 European Pat. Off. ........... 514/256

64-29363 1/1989 Japan ........................... 546/323

OTHER PUBLICATIONS

Chemical Abstracts, vol. 111, No. 11, Abstract 97094e, p. 729, Sep. 11, 1989.

*Primary Examiner*—C. Warren Ivy
*Assistant Examiner*—Zinna W. Davis
*Attorney, Agent, or Firm*—Sughrue, Mion, Zinn, Macpeak & Seas

[57] ABSTRACT

Leukotriene B4 antagonists of the formula:

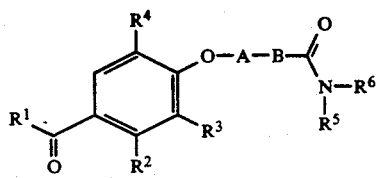

wherein each symbol is as defined in the specification, processes for producing them, and pharmaceutical compositions containing them. The compounds of the present invention are very useful as the drugs for the treatment of allergic and inflammatory diseases.

15 Claims, No Drawings

PYRIDINE COMPOUNDS WHICH ARE USEFUL AS LEUKOTRIENE B4 ANTAGONIST

BACKGROUND OF THE INVENTION

1. Technical Field

The present invention relates to compounds effective as leukotriene $B_4$ antagonists.

More particularly, this invention relates to leukotriene $B_4$ antagonists, to processes for producing them and to pharmaceutical compositions containing at least one of those leukotriene $B_4$ antagonists, which have excellent anti-leukotriene $B_4$ activity and are useful as an anti-allergic agent or an anti-inflammatory agent.

2. Prior Art

In 1979 B. Sammuelsson reported the isolation and biological effects of leukotrienes (B. Sammuelsson et al. (1980): Advances in Prostaglandin and Thromboxane Research, Vol. 6, edited by B. Sammuelsson, R. Ramwell, and R. Paaletti, P. I. Raven Press, New York).

Since then, a tremendous amount of research in the synthetic organic chemistry and pharmacology of leukotriene $A_4$, $B_4$, $C_4$, $D_4$, etc. has been performed.

Leukotrienes induce an increase in capillary permeability and cause smooth muscle contraction. Leukotriene $B_4$, one of leukotrienes which is shown below, has different pharmacological properties from the others. It is chemotactic for macrophages and neutrophils at concentrations of ~1 ng/ml (greater than any other known lipid chemotactic factor). It is detected in the synovia of patients with rheumatoid arthritis or gouty arthritis, and in the sputum of obstructive airways diseases which suggest that it is a primary mediator of inflammatory and allergic states.

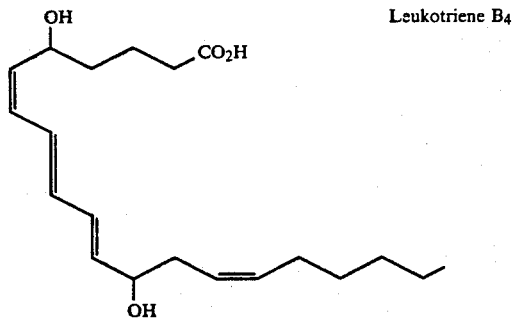

Leukotriene $B_4$

In recent research some compounds having an antagonism on $LTB_4$ have been reported. For example,

1) EP-A-0183177 (SUMITOMO PHARMACEUTICALS CO.)

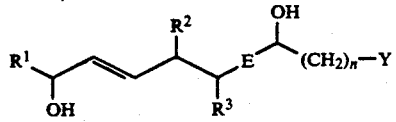

2) EP-A-276065 (ELI LILLY & CO)

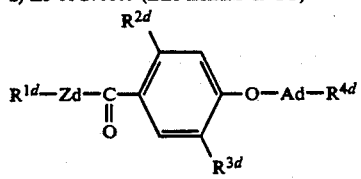

3) EP-A-276064 (ELI LILLY & CO)

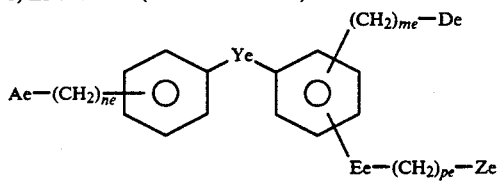

4) EP-A-0405116 (ONO PHARMACEUTICAL CO)

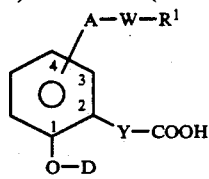

5) EP-A-292977 (SEARLE G D & CO)

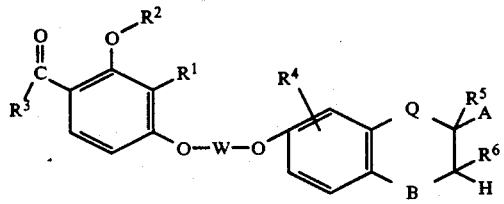

6) WO-A-8805045 (UPJOHN CO)

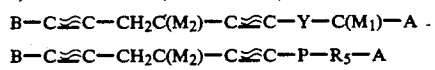

SUMMARY OF THE INVENTION

In accordance with the present invention, leukotriene $B_4$ antagonists of the following general formula [I] and their non-toxic pharmaceutically acceptable salts are provided, which have potent anti-leukotriene $B_4$ activity which include suppression of chemotaxis, degranulation and $O_2$-production of leukocytes, and modulation of lymphocytes activity, etc. This action may render these compounds very useful as the drugs for the treatment of inflammatory states or immunological disorders such as allergy, rheumatoid arthritis, and inflammatory bowel disease.

DISCLOSURE OF THE INVENTION

The novel leukotriene $B_4$ antagonists provided by the present invention are those represented by the formula [I]:

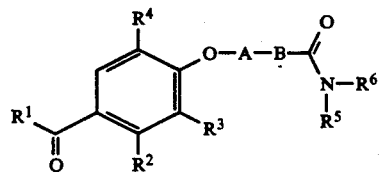

wherein
A is a $C_1$-$C_5$ alkylene chain;
B is a phenylene or 6 membered heteroaromatic group which is constituted by carbon atoms and one or two nitrogen atoms, and B may be, optionally substituted with one or two substituents selected from the group, consisting of a $C_1$-$C_5$ alkyl group, a $C_1$-$C_5$ alkoxy group, a hydroxyl group, a carboxyl group, a nitro group and a halogen atom;

$R^1$ is a $C_1$-$C_5$ alkyl group;
$R^2$ is a hydroxyl group or a $C_1$-$C_5$ alkoxy group;
$R^3$ and $R^4$ are each independently a hydrogen atom, a $C_1$-$C_5$ alkyl group, a $C_2$-$C_5$ alkenyl group or a $C_2$-$C_5$ alkynyl group;
$R^5$ is a hydrogen atom, a $C_1$-$C_5$ alkyl group or a hydroxy $C_1$-$C_5$ alkyl group;
$R^6$ is a group of the formula:

—X—Y—Z—R$^{6'}$ wherein
X is a phenylene group or a monocyclic 5~6 membered hetero aromatic group, and X is optionally substituted with one or two substituents selected from the group consisting of a $C_1$-$C_5$ alkyl group, a hydroxyl group, a carboxyl group, a nitro group and a halogen atom;
Y is a single bond or an oxygen atom;
Z is a single bond or a $C_1$-$C_5$ alkylene chain;
provided that when Y is an oxygen atom,
X is a phenylene group and Z is a $C_1$-$C_5$ alkylene chain;
$R^{6'}$ is a COOR$^7$ group,
a CONR$^8$R$^9$ group,
a CONHCHR$^{20}$(CH$_2$)$_n$COOR$^7$ group,
a CONHCHR$^{20}$(CH$_2$)$_n$CONR$^8$R$^9$ group,
a CONHCHR$^{20}$CONHCHR$^{22}$CO$_2$R$^7$ group or
a sulfamoyl group,
wherein
$R^7$ is a hydrogen atom, a benzyl group, a $C_1$-$C_5$ alkyl group or an $C_1$-$C_5$ alkyl group substituted with an aminoheteroaromatic group wherein the heteroaromatic group is a monocyclic 5~6 membered heteroaromatic group;
$R^8$ and $R^9$ are each independently a hydrogen atom, a $C_1$-$C_5$ alkyl group, hydroxy $C_1$-$C_5$ alkyl group, a hydroxyethylpyridyl group or a hydroxyethylthiazolyl group, or the group of the formula:

—NR$^8$R$^9$ represents a pyrrolidino, a piperidino or a morpholino group;
$R^{20}$ is a hydrogen atom, a hydroxyl group, a $C_1$-$C_5$ alkyl group, a phenyl group, a hydroxyphenyl group, a benzyl group, a hydroxy benzyl group or a substituted $C_1$-$C_5$ alkyl group wherein the substituent is selected from the group consisting of a hydroxyl group, a $C_1$-$C_5$ alkoxy group, a mercapto group, a methylthio group, an amino group, an indolyl group, an imidazolyl group, a carboxyl group, a $C_1$-$C_5$ alkoxycarbonyl group, a carbamoyl group and a quanidino group;
n is 0, 1, 2, 3, 4 or 5; and
$R^{22}$ is a hydrogen atom, a $C_1$-$C_5$ alkyl group or a $C_1$-$C_5$ hydroxyalkyl group;
or $R^6$ is a CHR$^{20}$(CH$_2$)$_n$COOR$^7$ group,
a CH$_2$CHR$^{20}$COOR$^7$ group,
a CHR$^{20}$(CH$_2$)$_n$CONR$^8$R$^9$ group,
a CH$_2$CHR$^{20}$CONR$^8$R$^9$ group,
a CHR$^{20}$(CH$_2$)$_n$OH group,
a CR$^{20}$R$^{22}$(CH$_2$)$_n$OH group,
a CH$_2$CHR$^{20}$OH group, or
a CHR$^{20}$CONHCHR$^{22}$CO$_2$R$^7$ group,
wherein $R^7$, $R^8$, $R^9$, $R^{20}$, $R^{22}$ and n are as defined above, or the group of the formula:

represents an azetidino group, pyrrolidino group, a piperidino group or a homopiperidino group, which is optionally substituted with one to two substituents selected from the group consisting of a hydroxyl group, a $C_1$-$C_5$ hydroxyalkyl group, carboxyl group, $C_1$-$C_5$ alkoxycarbonyl group and benzyloxycarbonyl group; or pharmaceutically acceptable salts thereof.

In the definitions as used above, the term "$C_1$-$C_5$ alkylene" means a straight or branched chain $C_1$-$C_5$ alkylene (e.g. methylene, ethylene, trimethylene, tetramethylene, pentamethylene, 1-methyethylene, 2-ethyltrimethylene, etc.).

The term "$C_1$-$C_5$ alkyl" means a straight or branched chain $C_1$-$C_5$ alkyl (e.g. methyl, ethyl, n-propyl, iso-propyl, n-butyl, iso-butyl, sec-butyl, tert-butyl, n-pentyl, iso-pentyl, sec-pentyl, neo-pentyl, etc.).

The term "$C_2$-$C_5$ alkenyl" means a straight or branched chain $C_2$-$C_5$ alkenyl (e.g. 1-methylethenyl, 1-ethylethenyl, 1-propenyl, 2-propenyl, 1-methyl-1-propenyl, 2-methyl-1-propenyl, 1-methyl-2-propenyl, 2-methyl-2-propenyl, 1,2-dimethyl-1-propenyl, 1-n-butenyl, 2-n-butenyl, 3-n-butenyl, 1-methyl-1-butenyl, 2-methyl-1-butenyl, 3-methyl-1-butenyl, 1-methyl-2-butenyl, 2-methyl-3-butenyl, 3-methyl-3-butenyl, 1-pentenyl, 2-pentenyl, 3-pentenyl, 4-pentenyl, etc.).

The term "$C_2$-$C_5$ alkynyl" means a straight or branched chain $C_2$-$C_5$ alkynyl (e.g. ethynyl, 1-propynyl, 2-propynyl, 1-methyl-2-propynyl, 1-n-butynyl, 2-n-butynyl, 3-n-butynyl, 3-methyl-1-butynyl, 1-methyl-2-butynyl, 2-methyl-3-butynyl, 1-pentynyl, 2-pentynyl, 3-pentynyl, 4-pentynyl, etc.).

The term "$C_1$-$C_5$ alkoxy" means alkoxy having $C_1$-$C_5$ alkyl moiety (e.g. methoxy, ethoxy, n-propoxy, iso-propoxy, n-butoxy, iso-butoxy, sec-butoxy, tert-butoxy, n-pentoxy, iso-pentoxy, sec-pentoxy, neo-pentoxy, etc.).

The term "6 membered heteroaromatic group which is constituted by carbon atoms and one or two nitrogen atoms" includes pyridinediyl, pyrazinediyl, pyrimidinediyl, etc.

The term "monocyclic 5~6 membered heteroaromatic group" contains, for example, 1-3 hetero atoms which can be a nitrogen, oxygen or sulfur atom, or an oxydized nitrogen atom (N→O), and examples of the monocyclic 5-6 membered heteroaromatic group are a pyridinediyl group and any one of the group of the formula (i)–(viii):

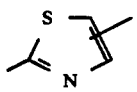 (i)

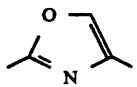 (ii)

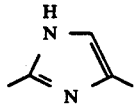 (iii)

-continued (iv) 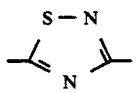

(v) 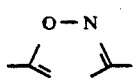

(vi) 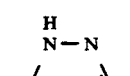

(vii) 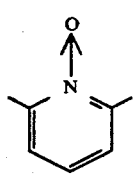

(viii) 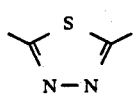

The term "hydroxyphenyl group" may be a 2-hydroxyphenyl, a 3-hydroxyphenyl or a 4-hydroxyphenyl group.

The term "hydroxybenzyl group" may be a 2-hydroxybenzyl, a 3-hydroxybenzyl or a 4-hydroxybenzyl group.

The term "halogen" may be a chlorine, a bromine or a fluorine atom.

The term "indolyl group" may be a 2-indolyl or 3-indolyl group.

The term "imidazolyl group" may be a 4-imidazolyl group.

A basic object of the present invention is to provide novel compounds effective as leukotriene $B_4$ antagonists [I] having excellent pharmacological activities.

Another object of the present invention is to provide processes for producing those compounds [I]. A further object of the present invention is to provide a pharmaceutical composition containing a compound of the formula [I]. These and other objects will be apparent to those skilled in the art to which the present invention pertains from the foregoing and subsequent descriptions.

The novel leukotriene $B_4$ antagonists [I] of the invention can be prepared by the following methods:

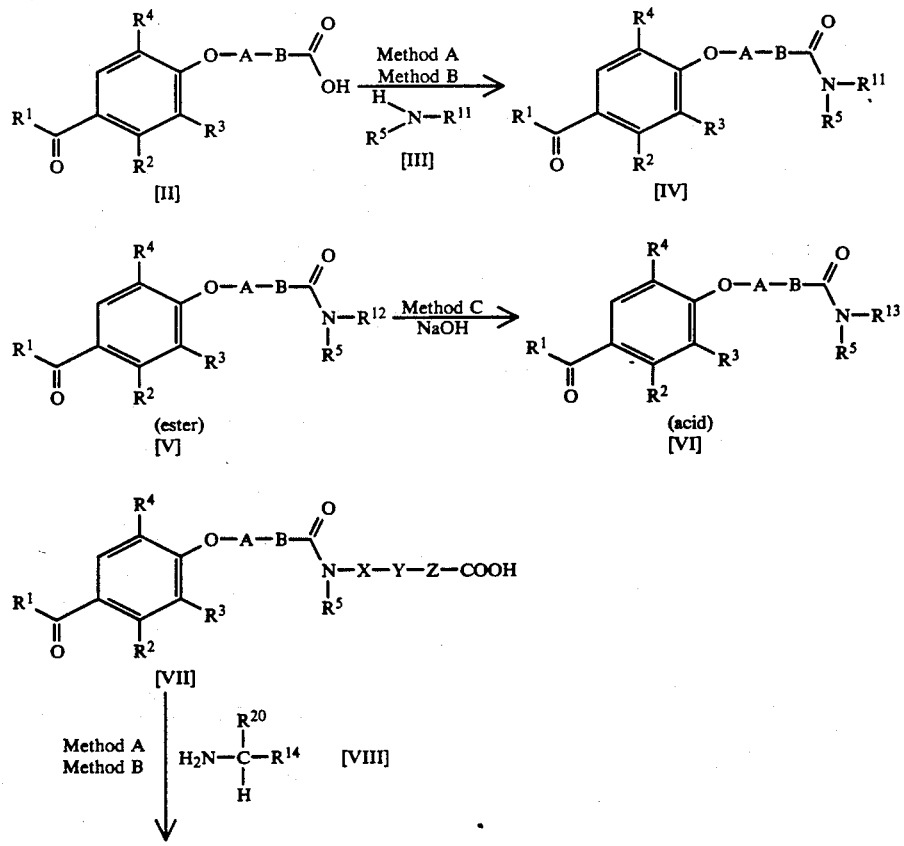

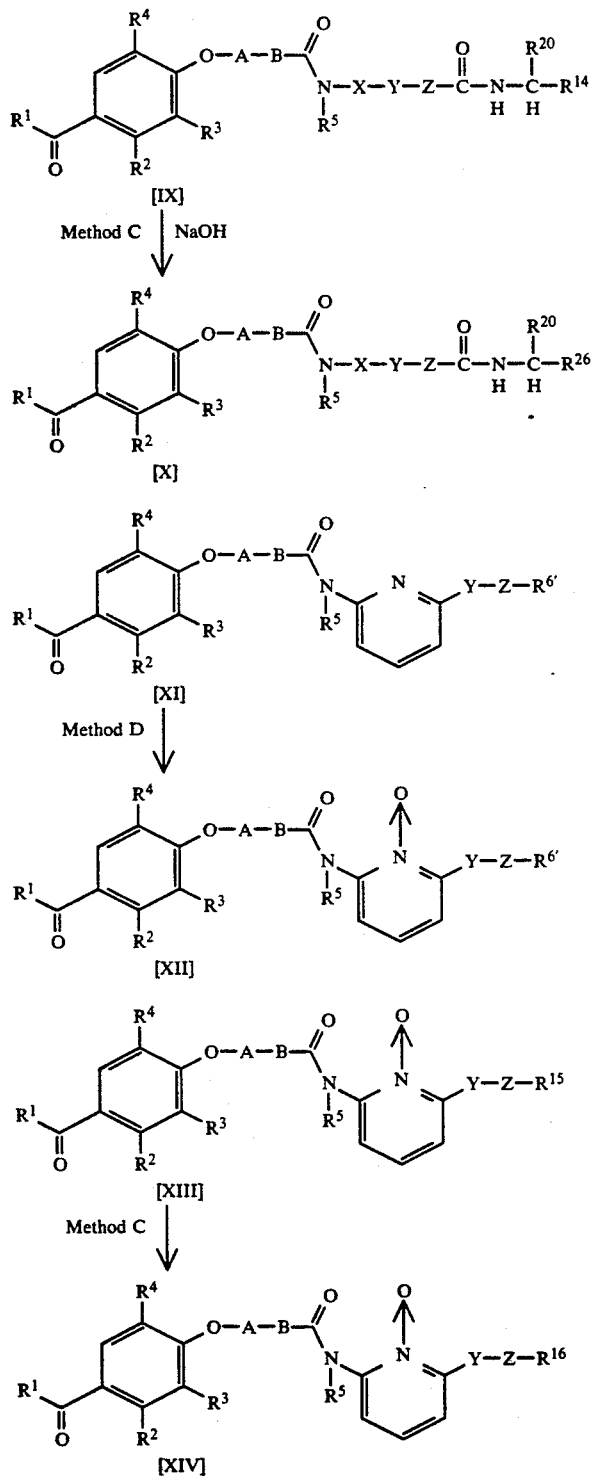

wherein
A, B, $R^1$, $R^2$, $R^3$, $R^4$, $R^5$, $R^{6'}$, X, Y, Z and $R^{20}$ are as defined above, and
$R^{11}$ is the same as $R^{6'}$, but it does not means free carboxylic group;
$R^{12}$ is a group of the formula:
  X-Y-Z-COOR$^{7'}$,
  X-Y-Z-CONHCHR$^{20}$(CH$_2$)$_n$COOR$^{7'}$,
  X-Y-Z-CONHCHR$^{20}$CONHCHR$^{22}$CO$_2$R$^{7'}$,
  CHR$^{20}$(CH$_2$)$_n$COOR$^{7'}$,
  CH$_2$CHR$^{20}$COOR$^{7'}$, or
  CHR$^{20}$CONHCHR$^{22}$COOR$^{7'}$,
wherein
X, Y, Z, $R^{20}$, $R^{22}$ and n are as defined above, and $R^{7'}$ is the same as $R^7$ but it does not mean a hydrogen atom,
$R^{13}$ is a group of the formula:
  X-Y-Z-COOH,
  X-Y-Z-CONHCHR$^{20}$(CH$_2$)$_n$ COOH,
  X-Y-Z-CONHCHR$^{20}$CONHCHR$^{22}$CO$_2$H, CHR²⁰(CH₂)ₙCOOH,
CH₂CHR²⁰COOH, or
CHR²⁰CONHCHR²²COOH,
wherein
X, Y, Z, R²⁰, R²² and n are as defined above,
R¹⁴ is a group of the formula:
(CH₂)ₙCOOR⁷', or
CONHCHR²²COOR⁷',
wherein
R⁷', R²² and n are as defined above,
R¹⁵ is a group of the formula:
COOR⁷',
CONHCHR²⁰(CH₂)ₙCOOR⁷', or
CONHCHR²⁰CONHCHR²²CO₂R⁷',
wherein
R⁷', R²⁰, R²² and n are as defined above,
R¹⁶ is a group of the formula:
COOH,
CONHCHR²⁰(CH₂)ₙCOOH, or
CONHCHR²⁰CONHCHR²²CO₂H,
wherein
R²⁰, R²² and n are as defined above,
R²⁶ is a group of the formula:
(CH₂)ₙCOOH, or
CONHCHR²²COOH, wherein R²² and n are as defined above.

Method A

The amide compound [IV] or [IX] can be prepared from an acid compound [II] or [VII] by reacting an amine compound [III] or [VIII] in the presence of a condensing agent (e.g. dicyclohexylcarbodiimide, ethyldimethylaminopropylcarbodiimide hydrochloride, etc.), hydroxybenzotriazole and a tertiary amine (e.g. triethylamine, 4-dimethylaminopyridine, etc.) in an inert solvent (e.g. dichloromethane, mixed solvent of dichloromethane and N,N-dimethylformamide, etc.) at a temperature in the range from 0° C. to the boiling temperature of the solvent.

If a substituent of R²⁰ of compound [VIII] is an impediment group (e.g. mercapto, carboxyl, amino group, etc.), the compound is previously protected by a protecting group (e.g. benzyl, benzyloxycarbonyl, t-butoxycarbonyl group, etc.), and after the reaction is carried out, the protecting group is eliminated. The protection and deprotection of R²⁰ can be carried out by the conventional procedure. [Protective Group in Organic Chemistry, Edited by J. F. W. McOmic (1973) 95-143].

Method B

The amide compound [IV] or [IX] can be obtained from an acid chloride or an acid anhydride of an acid compound [II] or [VII] by reacting with an amine compound [III] or [VIII] in the presence of a tertiary amine (e.g. triethylamine, etc.), or by reacting with a salt of an amine compound [III] or [VIII] (e.g. sodium salt, potassium salt, etc.) in the absence of amine in an inert solvent (e.g. tetrahydrofuran, etc.) at a temperature in the range from 0° C. to a boiling temperature of the solvent.

The transformation of an acid group to an acid chloride group can be carried out by treating the acid compound with phosphorous oxychloride or thionyl chloride in an inert solvent (e.g. chloroform, etc.) or in the absence of solvent at a temperature in the range of from −40° C. to the boiling temperature of the reaction mixture.

The transformation of an acid group to an acid anhydride group can be carried out by treating the acid compound with chloroformate ester (e.g. ethyl chloroformate, etc.) in the presence of a tertiary amine (e.g. triethylamine, etc.) in an inert solvent (e.g. chloroform, etc.) at a temperature in the range of from −40° C. to the boiling temperature of the solvent.

If a substituent of R²⁰ of compound [VIII] is a impediment group (e.g. mercapto, carboxyl, amino group, etc.), the compound is previously protected by a protecting group (e.g. benzyl group, benzyloxycarbonyl group, t-butoxycarbonyl group, etc.), and after the reaction is carried out, the protecting group is eliminated.

The protection and deprotection of R²⁰ can be carried out by the conventional procedure [Protective Group in Organic Chemistry, Edited by J. F. W. McOmic (1973) 95-143].

Method C

The acid compound [VI], [X] or [XIV] can be prepared by hydrolysis of the ester compound [V], [IX] or [XIII] by treating with an aqueous alkali (e.g. sodium hydroxide, lithium hydroxide) in an inert solvent (e.g. tetrahydrofuran, methanol, ethanol, etc.).

Method D

The N-oxide compound [XII] can be prepared from pyridine compound [XI] by treating with an oxidizing agent (e.g. m-chloroperbenzoic acid, etc.) in an inert solvent (e.g. methylene chloride, etc.).

The amine compounds [III] and [VIII] are known compounds or easily obtained as described in e.g. J. Goto, K. Sakane, Y. Nakai, T. Teraji, The journal of antibiotics, 37, 532 (1984), I. Csendes, B. W. Müller, W. Tosch, The journal of antibiotics, 36, 1020 (1983), M. Ohta, Yakugaku zassi, 72, 1536 (1983), JP-A-58-23697. And, the starting compounds [II], [II-1] and [II-2] can be obtained by the following method.

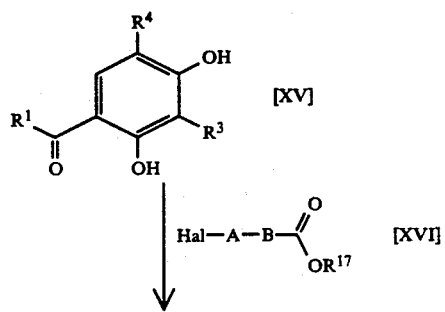

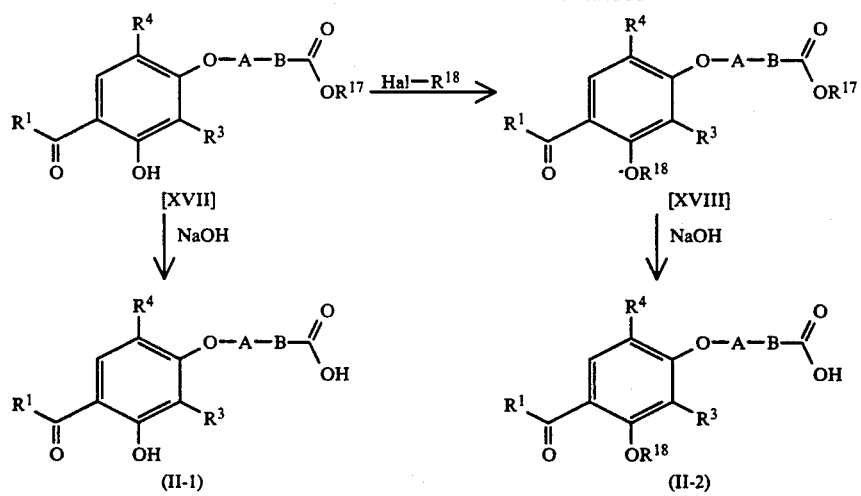

(wherein A, B, $R^1$, $R^2$, $R^3$ and $R^4$ are as defined above, $R^{17}$ is a $C_1$-$C_5$ alkyl group, $R^{18}$ is a $C_1$-$C_5$ alkyl group, $R^{18}$ is a $C_1$-$C_5$ alkyl group, Hal is a chlorine or bromine atom)

Alkylation of the compound [XV] into the compound [XVII] can be accomplished by treating the former with the compound [XVI] in an inert solvent (e.g. N,N-dimethylformamide, etc.) in the presence of a base (e.g. anhydrous potassium carbonate, etc.). Optionally, the compound [XVII] can be alkylated to produce the compound [XVIII] by the same procedure as used in the synthesis of the compound [XVII] from the compound [XV]. And, the compound (II-1) and (II-2), respectively, can be prepared from the compound [XVII] and [XVIII] by hydrolysis (Method C).

The compound [XV] is a known compound or easily obtained as described in e.g. J. Hurst, J. Wibberley, Journal of Chemical Society, 1962, 119.

The compound [XVI] is obtained by;

(1) In the case where both Hal and B of compound [XVI] are jointed to the same carbon atom:

the compound [XVI] is a known compound or easily obtained as described in e.g. J. Hurst, J. Wibberley, Journal of Chemical Society, 1962, 119, etc, (2) In the case that there are two carbon atoms between Hal and B in compound [XVI]:

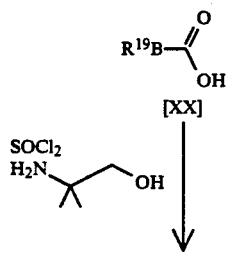

(wherein A, B and Hal are as defined above, $R^{19}$ is a $C_1$-$C_5$ alkyl group (but, there is at least one hydrogen atom at the α carbon bonded to B), $R^{21}$, $R^{23}$ are each independently a hydrogen atom or a $C_1$-$C_5$ alkyl group, $R^{24}$ is a $C_1$-$C_5$ alkyl group, and $R^{25}$ is a $C_1$-$C_5$ alkyl group or phenyl group)

the compound [XVI] is prepared in the following way:
first step: the carboxylic acid group of a compound [XX] is protected to yield a 4,4-dimethyl-2-oxazoline compound,
second step: the 4,4-dimethyl-2-oxazoline compound is treated with a base to deprotonate a hydrogen atom attached to a carbon atom adjacent to B group (e.g. sodium amide, n-butyl lithium, etc.), third step: the deprotected compound is reacted with the compound of the formula [XXI] (aldehyde or ketone) to yield a hydroxy compound, fourth step: the hydroxyl compound is alkylated by reacting with a compound of the formula $R^{24}$-Hal, fifth step: the alkylated compound is treated with halogenated hydrogen (e.g. hydrogen chloride, hydrogen bromide, etc.) in the alcohol represented by $R^{17}$OH.

(3) In the case that there are 3 or more carbon atoms between Hal and B in the compound [XVI]:

the compound [XVI] is prepared in the same way, except modifying the alkylation reaction, as described in above (2), i.e., the compound [XX] is protected and deprotonated, and then alkylated by alkylhalide [XXII]. The alkylated product is treated with halogenated hydrogen (e.g. hydrogen chloride, hydrogen bromide, etc.) in the alcohol represented by $R^{17}$OH.

Specific examples of the leukotriene $B_4$ antagonists are as follows:

TABLE 1

| $R^3$ | H | H | H | n-Pr | H | H | H | H | H |
|---|---|---|---|---|---|---|---|---|---|
| $R^4$ | Me | n-Pr | n-Pr | H | Et | Et | Et | Et | Et |
| $R^5$ | H | H | H | H | $CH_3$ | Et | n-Pr | i-Pr | H |
| $R^{6'}$ | $CONH_2$ | $CONH_2$ | $CONH_2$ | $CONH_2$ | $CONH_2$ | $CONH_2$ | $CONH_2$ | $CONH_2$ | CONHMe |

TABLE 2

| A | $-CH_2-$ | $-CH_2-$ | $-CH_2-$ | $-CH_2-$ | $-CH_2-$ | $-(CH_2)_2-$ | $-(CH_2)_3-$ | $-(CH_2)_4-$ | $-(CH_2)_5-$ |
|---|---|---|---|---|---|---|---|---|---|
| $R^{6'}$ | $CONMe_2$ | CONHiPr | C(O)-N-pyrrolidine | C(O)-N-piperazine-N-C(O) | C(O)-N-morpholine | $CONH_2$ | $CONH_2$ | $CONH_2$ | $CONH_2$ |

TABLE 3

| A | $-CHMe-$ | $-CH_2-$ | $-CH_2-$ | $-CH_2-$ | $-CH_2-$ | $-CH_2-$ | $-CH_2-$ | $-CH_2-$ | $-CH_2-$ |
|---|---|---|---|---|---|---|---|---|---|
| B | pyridine | pyrazine | pyrazine | pyrazine | pyrazine | pyrazine | pyrazine | pyrazine | pyrimidine |
| Z | $-CH_2-$ | single bond | $-CH_2-$ | $-(CH_2)_2-$ | $-(CH_2)_3-$ | $-(CH_2)_4-$ | $-(CH_2)_5-$ | $-CH_2-$ | single bond |

TABLE 4
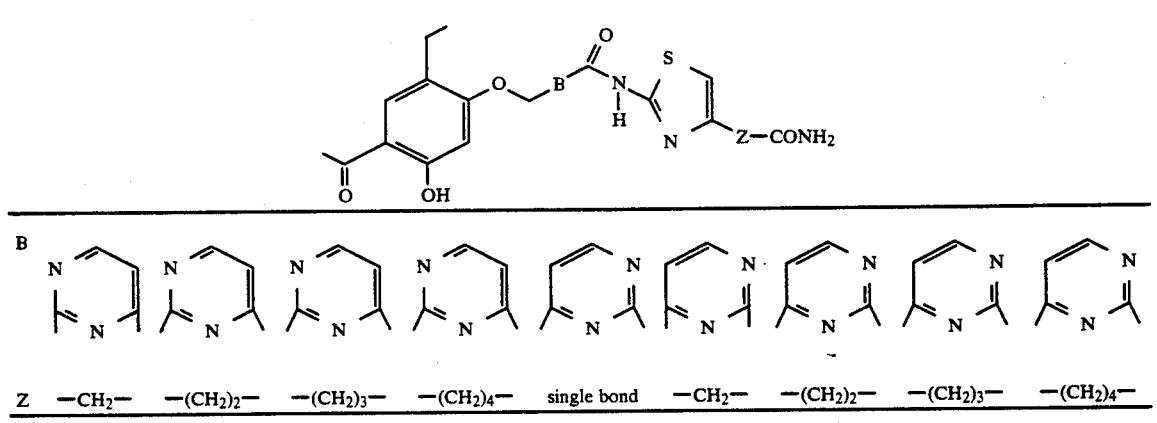
TABLE 5
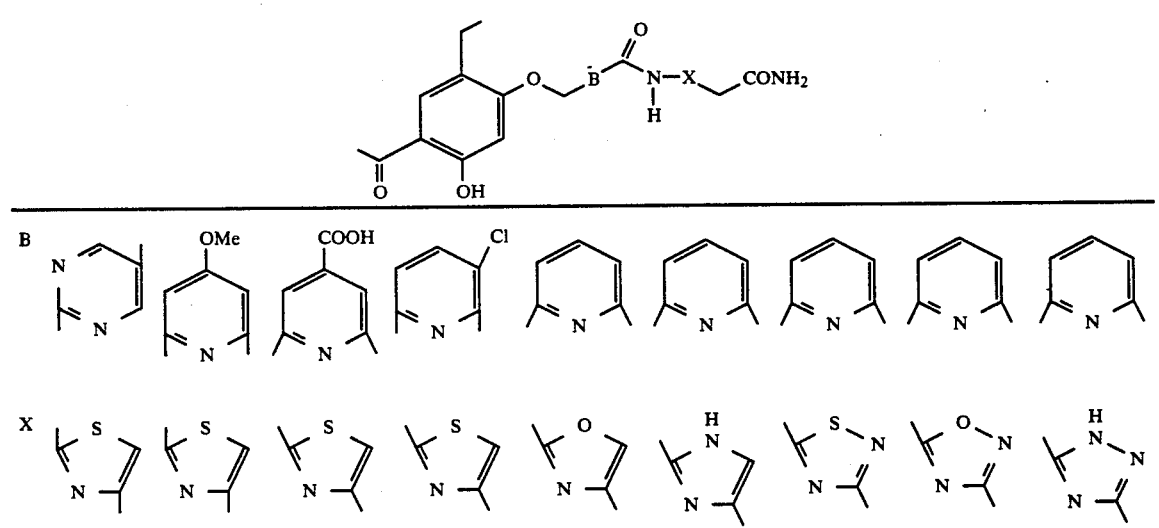
TABLE 6
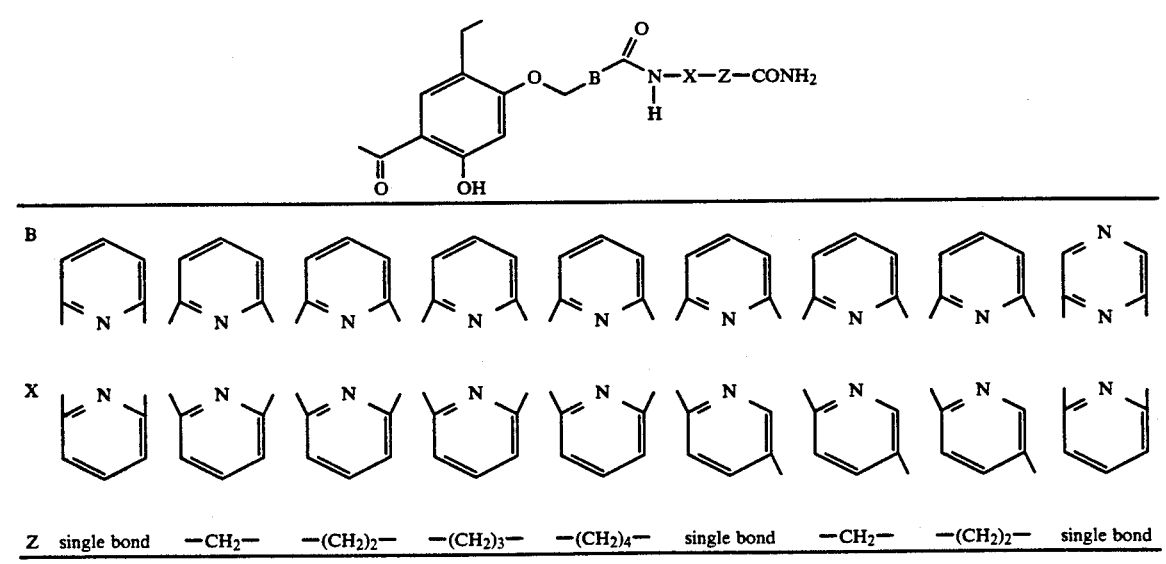

TABLE 7
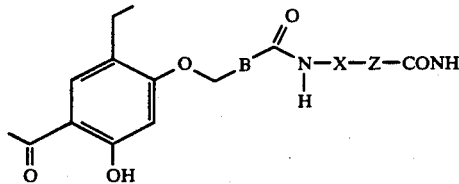
| B | | | | | | | | | |
|---|---|---|---|---|---|---|---|---|---|
| X | | | | | | | | | |
| Z | —CH₂— | —(CH₂)₂— | —(CH₂)₃— | —(CH₂)₄— | single bond | —CH₂— | —(CH₂)₂— | single bond | —CH₂— |
TABLE 8
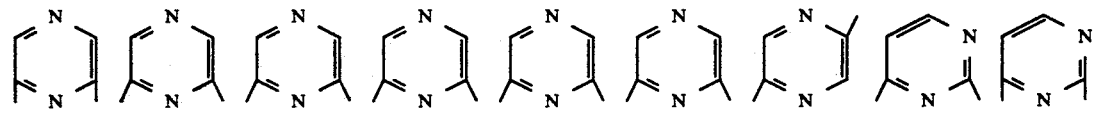
| B | | | | | | | | | |
|---|---|---|---|---|---|---|---|---|---|
| X | | | | | | | | | |
| Z | —(CH₂)₂— | —(CH₂)₃— | —(CH₂)₄— | —CH₂— | single bond | —(CH₂)₂— | —(CH₂)₃— | —(CH₂)₄— | —CMe₂— |
TABLE 9
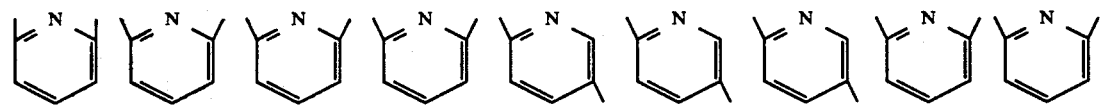
| X | | | | | | | | | |
|---|---|---|---|---|---|---|---|---|---|
| Z | single bond | single bond | single bond | single bond | —CH₂— | —(CH₂)₂— | —CH₂— | —(CH₂)₂— | —CH₂— |
| R⁶' | CONH₂ | CONH₂ | SO₂NH₂ | SO₂NH₂ | CONH₂ | CONH₂ | SO₂NH₂ | SO₂NH₂ | SO₂NH₂ |

TABLE 10

[Structure: ethyl- and acetyl-substituted phenol with R² substituent, linked via -O-CH₂- to a pyridine-2-carboxamide bearing -N(R⁵)-X-Y-Z-R⁶']

| R² | OH | OH | OH | OH | OMe | OH | OH | OH | OH |
|---|---|---|---|---|---|---|---|---|---|
| R⁵ | H | H | H | H | H | H | Me | Et | n-Pr |
| X | phenyl (1,2) | phenyl (1,3) | phenyl (1,4) | phenyl (1,4) | thiazole | thiazole | thiazole | thiazole | thiazole |
| Y | —O— | —O— | —O— | —O— | single bond | single bond | single bond | single bond | single bond |
| Z | —CH₂— | —(CH₂)₂— | —CH₂— | —(CH₂)₂— | —CH₂— | —CH₂— | —CH₂— | —CH₂— | —CH₂— |
| R⁶' | CONH₂ | CONH₂ | CONH₂ | CONH₂ | CONH₂ | CO₂Et | CO₂Et | CO₂Et | CO₂Et |

TABLE 11

[Structure: ethyl- and acetyl-substituted phenol (5-OH) with -O-A-B-C(O)-N(R⁵)- linked to thiazole bearing -Z-CO₂Et]

| A | —CH₂— | —(CH₂)₂— | —(CH₂)₃— | —(CH₂)₄— | —(CH₂)₅— | —CHMe— | —CH₂— | —CH₂— | —CH₂— |
|---|---|---|---|---|---|---|---|---|---|
| B | pyridine | pyridine | pyridine | pyridine | pyridine | pyridine | pyrazine | pyrazine | pyrazine |
| R⁵ | i-Pr | H | H | H | H | H | H | H | H |
| Z | —CH₂— | —CH₂— | —CH₂— | —CH₂— | —CH₂— | —CH₂— | —CH₂— | —(CH₂)₂— | —(CH₂)₃— |

TABLE 12

[Structure: ethyl- and acetyl-substituted phenol (5-OH) with -O-CH₂-B-C(O)-NH-X-Z-CO₂Et]

| B | pyrimidine | pyrimidine | pyrimidine | pyrimidine | pyrimidine | pyrimidine | pyridine | pyridine | pyridine |
|---|---|---|---|---|---|---|---|---|---|
| X | thiazole | thiazole | thiazole | thiazole | thiazole | thiazole | oxazole | imidazole (NH) | thiadiazole |
| Z | —CH₂— | —(CH₂)₂— | —(CH₂)₃— | —CH₂— | —(CH₂)₂— | —(CH₂)₃— | —CH₂— | —CH₂— | —CH₂— |

TABLE 15

| X | | | | | | | | | |
|---|---|---|---|---|---|---|---|---|---|
| Y | —O— | —O— | —O— | —O— | single bond | single bond | single bond | single bond | single bond |
| Z | —CH₂— | —CH₂— | —(CH₂)₂— | —(CH₂)₂— | single bond | —CH₂— | —(CH₂)₂— | —(CH₂)₃— | —(CH₂)₄— |
| R⁶' | CO₂Et | CO₂Et | CO₂Et | CO₂Et | CO₂H | CO₂H | CO₂H | CO₂H | CO₂H |

TABLE 16
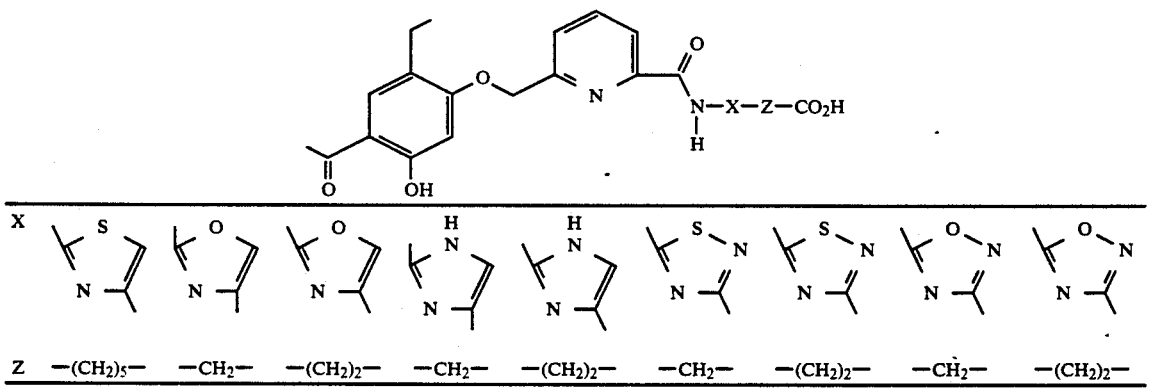
TABLE 17
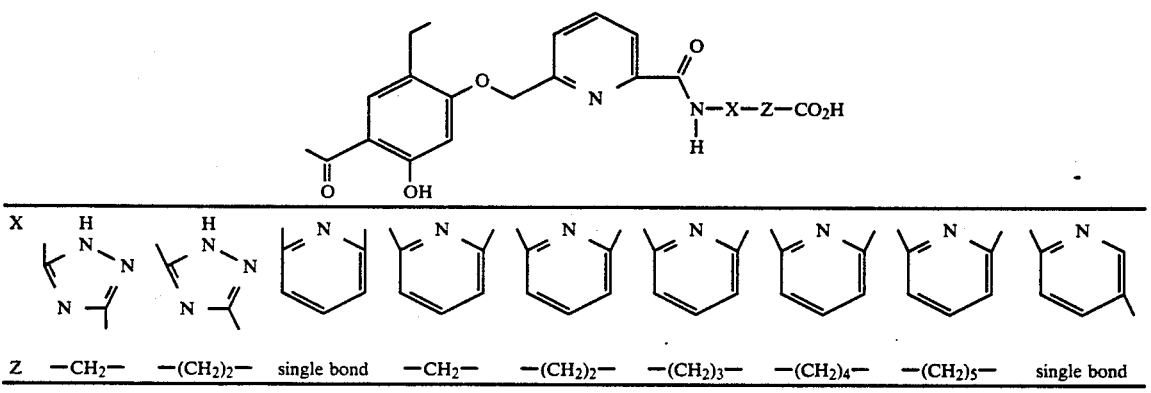
TABLE 18
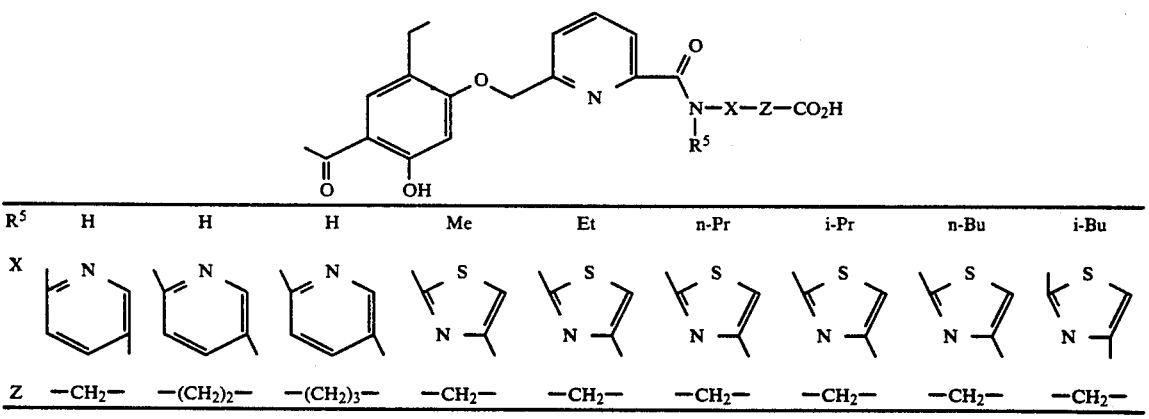
TABLE 19
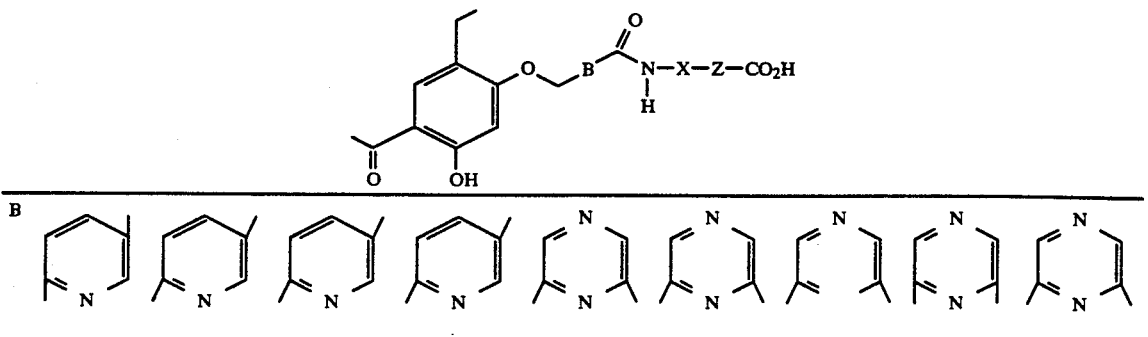

TABLE 19-continued

| X | [thiazole] | [thiazole] | [pyridine] | [pyridine] | [thiazole] | [thiazole] | [thiazole] | [pyridine] | [pyridine] |
|---|---|---|---|---|---|---|---|---|---|
| Z | —CH$_2$— | —(CH$_2$)$_2$— | —CH$_2$— | —(CH$_2$)$_2$— | —CH$_2$— | —(CH$_2$)$_2$— | —(CH$_2$)$_3$— | —CH$_2$— | —(CH$_2$)$_2$— |

TABLE 20

[Structure: 2-ethyl-4-acetyl-5-hydroxyphenyl-O-CH$_2$-B-C(=O)-NH-X-Z-CO$_2$H]

| B | [pyrazine] | [pyrazine] | [pyrazine] | [pyrazine] | [pyrazine] | [pyrazine] | [pyrazine] | [pyrimidine] | [pyrimidine] |
|---|---|---|---|---|---|---|---|---|---|
| X | [pyridine] | [thiazole] | [thiazole] | [thiazole] | [pyridine] | [pyridine] | [pyridine] | [thiazole] | [thiazole] |
| Z | —(CH$_2$)$_3$— | —CH$_2$— | —(CH$_2$)$_2$— | —(CH$_2$)$_3$— | —CH$_2$— | —(CH$_2$)$_2$— | —(CH$_2$)$_3$— | —CH$_2$— | —(CH$_2$)$_2$— |

TABLE 21

[Structure: 2-ethyl-4-acetyl-5-hydroxyphenyl-O-CH$_2$-B-C(=O)-NH-X-Z-CO$_2$H]

| B | [pyrimidine] | [pyrimidine] | [pyrimidine] | [pyrimidine] | [pyrimidine] | [pyrimidine] | [pyrimidine] | [pyrimidine] | [pyrimidine] |
|---|---|---|---|---|---|---|---|---|---|
| X | [thiazole] | [pyridine] | [pyridine] | [pyridine] | [thiazole] | [thiazole] | [thiazole] | [pyridine] | [pyridine] |
| Z | —(CH$_2$)$_3$— | —CH$_2$— | —(CH$_2$)$_2$— | —(CH$_2$)$_3$— | —CH$_2$— | —(CH$_2$)$_2$— | —(CH$_2$)$_3$— | —CH$_2$— | —(CH$_2$)$_2$— |

TABLE 22

[Structure: 2-ethyl-4-acetyl-5-hydroxyphenyl-O-A-B-C(=O)-NH-X-Z-CO$_2$H]

| A | —CH$_2$— | —CH$_2$— | —CH$_2$— | —CH$_2$— | —CH$_2$— | —CH$_2$— | —CH$_2$— | —(CH$_2$)$_2$— | —(CH$_2$)$_3$— |
|---|---|---|---|---|---|---|---|---|---|

TABLE 22-continued

| B | (pyrimidine) | (pyrimidine) | (pyrimidine) | (pyrimidine) | (pyrimidine) | (pyrimidine) | (pyridine) | (pyridine) |
|---|---|---|---|---|---|---|---|---|
| X | (pyridine) | (thiazole) | (thiazole) | (thiazole) | (pyridine) | (pyridine) | (thiazole) | (thiazole) |
| Z | $-(CH_2)_3-$ | $-CH_2-$ | $-(CH_2)_2-$ | $-(CH_2)_3-$ | $-CH_2-$ | $-(CH_2)_2-$ | $-(CH_2)_3-$ | $-CH_2-$ | $-CH_2-$ |

TABLE 23

| $R^4$ | Et | Et | Et | Me | Et | n-Pr | n-Bu | $-CH_2-CH=CH_2$ (via CH) | $CH_2C{\equiv}CH$ |
|---|---|---|---|---|---|---|---|---|---|
| A | $-(CH_2)_4-$ | $-(CH_2)_5-$ | $-CHMe-$ | $-CH_2-$ | $-CH_2-$ | $-CH_2-$ | $-CH_2-$ | $-CH_2-$ | $-CH_2-$ |

TABLE 24

| $R^3$ | Me | Et | n-Pr | n-Bu | n-Pentyl | $-CH_2-CH=CH_2$ (via CH) | $CH_2C{\equiv}CH$ | Me | Et |
|---|---|---|---|---|---|---|---|---|---|
| $R^4$ | Et | Et | Et | Et | Et | Et | Et | H | H |

TABLE 25

| $R^1$ | Me | Me | Me | Me | Me | Me | Me | Et | n-Pr |
|---|---|---|---|---|---|---|---|---|---|
| $R^2$ | OH | OH | OH | OH | OMe | OEt | O-n-Pr | OH | OH |
| $R^3$ | i-Pr | i-Bu | n-Bu | n-Pentyl | H | H | H | H | H |
| $R^4$ | H | H | H | H | Et | Et | Et | Et | Et |

TABLE 26

[Structure: ethyl/hydroxy-substituted benzene with R¹C(O)- group, linked via -OCH₂- to pyridine-2,6-diyl, then -C(O)NH-C(=S)N=CH-CH₂-R⁶']

| R¹ | n-Bu | n-Pentyl | Me | Me | Me |
|---|---|---|---|---|---|
| R⁶' | CO₂H | CO₂H | -C(O)NH-CH₂CO₂Me | -C(O)NH-(CH₂)₂CO₂Me | -C(O)NH-CH₂CO₂H |

TABLE 27

[Structure: acetyl/hydroxy-substituted ethylbenzene linked via -OCH₂- to pyridine-2,6-diyl then -C(O)NH-X-CH₂-R⁶']

| X | thiazol-2,4-diyl | pyridine-2,6-diyl | pyridine-2,6-diyl | pyridine-2,6-diyl | pyridine-2,6-diyl |
|---|---|---|---|---|---|
| R⁶' | -C(O)NH-(CH₂)₂CO₂H | -C(O)NH-CH₂CO₂Me | -C(O)NH-(CH₂)₂CO₂Me | -C(O)NH-CH₂CO₂H | -C(O)NH-(CH₂)₂CO₂H |

TABLE 28

[Structure: acetyl/hydroxy-substituted ethylbenzene linked via -OCH₂- to pyridine-2,6-diyl then -C(O)NH-X-CH₂-R⁶']

| X | pyridine-2,6-diyl | thiazol-2,4-diyl | thiazol-2,4-diyl | thiazol-2,4-diyl | thiazol-2,4-diyl |
|---|---|---|---|---|---|
| R⁶' | -C(O)NH-(CH₂)₃CO₂H | -C(O)NH-CH(i-Pr)CO₂Me | -C(O)NH-CH(CH₂CO₂H)CO₂H | -C(O)NH-CH((CH₂)₄NH₂)CO₂H | -C(O)NH-CH(CH₂OH)CO₂H |

TABLE 29

[Structure: acetyl/hydroxy-substituted ethylbenzene linked via -OCH₂- to pyridine-2,6-diyl then -C(O)NH-R⁶]

| R⁶ | CH₂CO₂H | (CH₂)₂CO₂H | (CH₂)₃CO₂H | (CH₂)₄CO₂H | CH₂CO₂Me |

TABLE 30

Structure: 2-ethyl-4-acetyl-5-hydroxyphenoxy-methyl-pyridine-6-carboxamide-NH-R⁶

| R⁶ | CH₂CO₂Et | CH₂CO₂CH₂–C₆H₅ | CHCO₂H\|CH₃ | CHCO₂H\|CH(CH₃)₂ | CHCO₂H\|CH(CH₃)CH₂CH₃ |

TABLE 31

Structure: 2-ethyl-4-acetyl-5-hydroxyphenoxy-methyl-pyridine-6-carboxamide-NH-R⁶

| R⁶ | CHCO₂H\|CH₂CH(CH₃)₂ | CHCO₂H\|C₆H₅ | CHCO₂H\|CH₂C₆H₅ | CHCO₂H\|CH₂-C₆H₄-OH | CHCO₂H\|CH₂OH |

TABLE 32

Structure: 2-ethyl-4-acetyl-5-hydroxyphenoxy-methyl-pyridine-6-carboxamide-NH-R⁶

| R⁶ | CHCO₂H\|CH(CH₃)OH | CH₂CO₂H\|CH₂CH₂OH | CH₂CO₂H\|CH₂CH₂SMe | CH₂CO₂H\|CH₂SH | CHCO₂H\|(CH₂)₄NH₂ |

TABLE 33

Structure: 2-ethyl-4-acetyl-5-hydroxyphenoxy-methyl-pyridine-6-carboxamide-NH-R⁶

| R⁶ | CHCO₂H–CH₂–(indol-3-yl) | CHCO₂H–CH₂–(imidazol-4-yl) | CHCO₂H\|CH₂CO₂H | CHCO₂H\|CH₂CH₂CO₂H | CHCO₂H\|CH₂CH₂CONH₂ |

TABLE 34

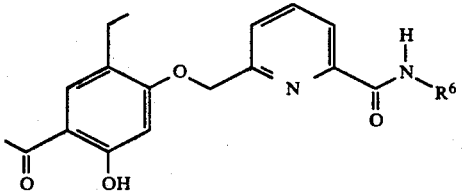

| R⁶ | CHCO₂H<br>\|<br>CH₂CONH₂ | CHCO₂H<br>\|<br>(CH₂)₄NHCNH₂<br>\|\|<br>NH | CH₂CONH₂ | CH₂CONHCH₃ | CH₂CONMe₂ |

TABLE 35

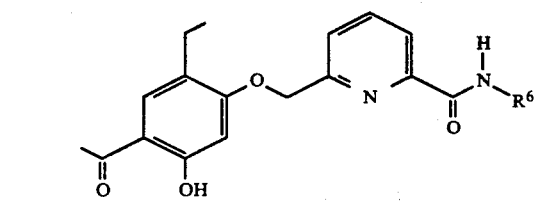

| R⁶ | (CH₂)₂CONH₂ | (CH₂)₃CONMe₂ | CH₂CON(piperidinyl) | CH₂CON(morpholinyl) | CH₂CON(pyrrolidinyl) |

TABLE 36

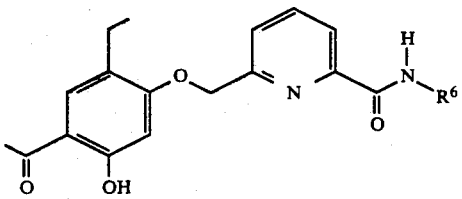

| R⁶ | CHCONH₂<br>\|<br>CH₃ | CHCONH₂<br>\|<br>iPr | CHCONMe₂<br>\|<br>Ph | CHCONMe₂<br>\|<br>OH | CHCONHMe<br>\|<br>OH |

TABLE 37

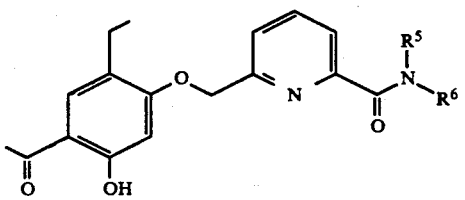

| N(R⁵)(R⁶) | piperidine-4-CO₂H | piperidine-3-CO₂H | 3-hydroxypyrrolidine | 2-(hydroxymethyl)pyrrolidine | 4-hydroxypyrrolidine-2-CO₂H |

TABLE 38

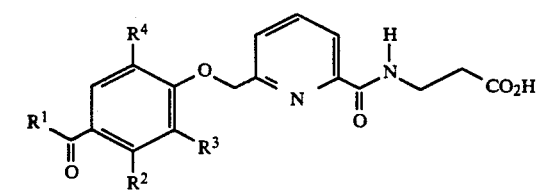

| R[1] | Et | n-Pr | Me | Me | Me |
|---|---|---|---|---|---|
| R[2] | OH | OH | OMe | OEt | OH |
| R[3] | H | H | H | H | n-Pr |
| R[4] | Et | Et | Et | Et | H |

TABLE 39

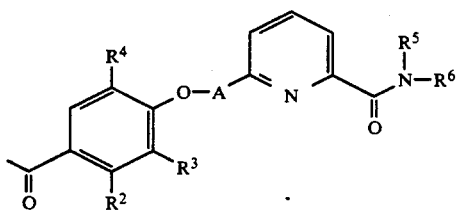

| R[2] | OH | OMe | OMe | OH | OH |
|---|---|---|---|---|---|
| R[3] | n-Pr | n-Pr | n-Pr | H | H |
| R[4] | H | H | H | Et | Et |
| A | —CH$_2$— | —CH$_2$— | —CH$_2$— | —(CH$_2$)$_2$— | —CH$_2$— |
| R[5] | H | H | H | H | Me |
| R[6] | CHCO$_2$H<br>\|<br>CH$_3$ | CHCO$_2$H<br>\|<br>CH$_3$ | (CH$_2$)$_2$CO$_2$H | (CH$_2$)$_2$CO$_2$H | (CH$_2$)$_2$CO$_2$H |

TABLE 40

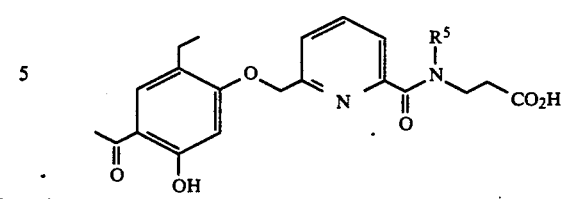

| R[5] | Et | n-Pr | isoBu | sec-Bu | (CH$_2$)$_2$OH |
|---|---|---|---|---|---|

TABLE 41

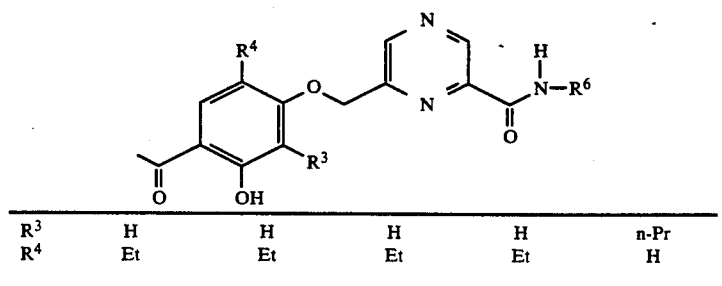

| R[3] | H | H | H | H | n-Pr |
|---|---|---|---|---|---|
| R[4] | Et | Et | Et | Et | H |
| R[6] | (CH$_2$)$_2$CO$_2$H | CHCO$_2$H<br>\|<br>CH$_3$ | CHCO$_2$H<br>\|<br>CH$_2$OH | CHCO$_2$H<br>\|<br>CH$_2$CO$_2$H | CHCO$_2$H<br>\|<br>CH$_2$CO$_2$H |

TABLE 42

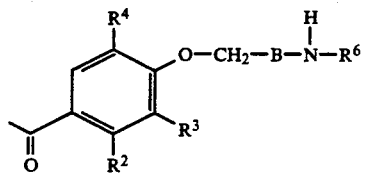

| R[2] | OMe | OH | OH | OH | OH |
|---|---|---|---|---|---|
| R[3] | n-Pr | H | H | H | H |
| R[4] | H | Et | Et | Et | Et |
| B | 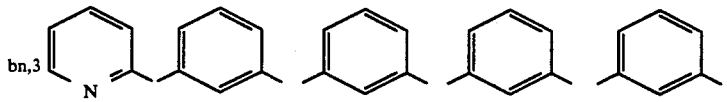 | | | | |

TABLE 42-continued

| R⁶ | CHCO₂H<br>CH₂CO₂H | (CH₂)₂CO₂H | CHCO₂H<br>CH₃ | CHCO₂H<br>CH₂OH | CHCO₂H<br>CH₂CO₂H |
|---|---|---|---|---|---|

TABLE 43

Structure: acetyl-phenyl(R², R³, R⁴)-O-CH₂-B-C(=O)-NH-R⁶

| R² | OH | OMe | OH | OH | OH |
|---|---|---|---|---|---|
| R³ | n-Pr | n-Pr | H | H | H |
| R⁴ | H | H | Et | Et | Et |

| B | 1,3-phenylene | 1,3-phenylene | 2,4-pyrimidinediyl | 2,4-pyrimidinediyl | 2,4-pyrimidinediyl |
|---|---|---|---|---|---|

| R⁶ | CHCO₂H<br>CH₂CO₂H | CHCO₂H<br>CH₂CO₂H | (CH₂)₂CO₂H | CHCO₂H<br>CH₃ | CHCO₂H<br>CH₂OH |
|---|---|---|---|---|---|

TABLE 44

Structure: acetyl-phenyl(R², R³, R⁴)-O-CH₂-(pyrimidin-2,4-diyl)-CH₂-NH-R⁶

| R² | OH | OH | OMe | OH | OH |
|---|---|---|---|---|---|
| R³ | H | n-Pr | n-Pr | H | H |
| R⁴ | Et | H | H | Et | Et |

| R⁶ | CHCO₂H<br>CH₂CO₂H | CHCO₂H<br>CH₂CO₂H | CHCO₂H<br>CH₂CO₂H | CHCO₂H<br>CH₃ | CHCO₂H<br>CH₂OH |
|---|---|---|---|---|---|

TABLE 45

Structure: 4-acetyl-2-ethyl-5-hydroxyphenyl-O-CH₂-(pyridin-2,5-diyl)-C(=O)-NH-R⁶

| R⁶ | CHCO₂H<br>iPr | 2-methylthiazol-4-yl-CH₂CH₂OH | pyridin-2-yl-CH₂CH₂OH | CHCO₂H<br>CH₂OH | CHCH₂CO₂H<br>CH₃ |
|---|---|---|---|---|---|

TABLE 46

| R¹ | Me | Et | Me | Me | Me |
|---|---|---|---|---|---|
| R⁶ | (CH₂)₂OH | (CH₂)₃OH | (CH₂)₄OH | CHCH₂OH<br>\|<br>CH₃ | CHCH₂OH<br>\|<br>CH₂CH₃ |

TABLE 47

| R² | OH | O-n-Pr | OH | OH | OH |
|---|---|---|---|---|---|
| R³ | Me | H | H | H | H |
| R⁴ | Me | H | Et | Et | Et |
| R⁵ | H | H | H | Me | H |
| R⁶ | (CH₂)₂CO₂H | (CH₂)₂CO₂H | CH(CH₂OH)₂ | CH(CH₂OH)₂ | CH₂CONHCH₂CO₂H |

Among the leukotriene $B_4$ antagonists thus obtained, the compound [I] can be converted to a pharmaceutically acceptable salt form. The pharmaceutically acceptable salts of these leukotriene $B_4$ antagonists can be formed with pharmaceutically acceptable metal cation such as sodium, potassium, magnesium and calcium, ammonium or amine cations.

The preparations of pharmaceutical compositions can be carried out by conventional methods. For example, leukotriene $B_4$ antagonists [I] may be mixed with carriers, diluents, lubricants, fillers and/or binders such as lactose, sucrose, calcium phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, injections, ointment, suppositories and the like. In a clinical practice, the leukotriene $B_4$ antagonists [I] can be administered orally, intranasally, intradermally or the like.

The daily dosage may vary depending upon the administration route, symptom, age or weight of the patient, and the usual oral dosage of the active ingredient is between about 1 mg and about 1000 mg daily for human beings.

DESCRIPTION OF THE PREFERRED EMBODIMENTS

Practical and preferred embodiments of the present invention are illustrated in the following examples, which are not intended to limit the scope of the invention.

REFERENCE EXAMPLE 1

5-Ethyl-2,4-dihydroxyacetophenone (0.97 g, 5.0 mmol) and methyl 6-bromomethylpyridine-2-carboxylate (1.38 g, 5.8 mmol) were dissolved in an N,N-dimethylformamide solution (50 ml), and anhydrous potassium carbonate (480 mg) was added to the above solution, and the mixture was stirred at room temperature for 16 hours. The reaction mixture was poured into water and extracted with ethyl acetate (100 ml×3).

The extract was dried, concentrated and chromatographed on silica gel to give methyl 6-[(4-acetyl-2-ethyl-5-hydroxyphenoxy)methyl]pyridine-2-carboxylate.

REFERENCE EXAMPLE 2

Methyl 6-[(4-acetyl-2-ethyl-5-hydroxyphenoxy)methyl]pyridine-2-carboxylate (38 mg, 12 mmol) was dissolved in a methanol solution (2 ml), and one normal sodium hydroxide (1 ml) was added to the above solution at 0° C., and the mixture was stirred at room temperature for 1 hour. One-tenth normal potassium bisulfate was titrated to the above solution until it became pH2. Then, precipitated white crystals were separated by filtration, and washed with water, and dried to give 6-[(4-acetyl-2-ethyl-5-hydroxyphenoxy)methyl]pyridine-2-carboxylic acid.

REFERENCE EXAMPLE 3

3-n-Propyl-2,4-dihydroxyacetophenone (816 mg, 4.2 mmol) was added to a methanol solution (10 ml), sodium metal was added to the solution at 0° C., and the mixture was stirred for 30 min, and evaporated under reduced pressure, and dried to give a sodium salt of 3-n-propyl-2,4-dihydroxyacetophenone. The salt was dissolved in N,N-dimethylformamide (10 ml), and it was added to a N,N-dimethylformamide solution (10 ml) of methyl-6-bromomethylpyridine-2-carboxylate (920 mg, 4.0 mmol) at room temperature, and the mixture was stirred for 1 hour.

The reaction mixture was poured into water, and normal potassium bisulfate was titrated until it became pH3, and extracted with ethyl acetate (100 ml×3). The extract was dried, concentrated and chromatographed on silica gel to give methyl 6-[(4-acetyl-3-hydroxy-2-n-propylphenoxy)methyl]pyridine-2-carboxylate.

REFERENCE EXAMPLE 4

According to the procedure of Reference Example 2, 6-[(4-acetyl-3-hydroxy-2-n-propylphenoxy)methyl]-pyridine-2-carboxylic acid was obtained by hydrolysis of methyl 6-[(4-acetyl-3-hydroxy-2-n-propylphenoxy)-methyl]pyridine-2-carboxylate.

REFERENCE EXAMPLE 5

Anhydrous potassium carbonate (1.0 g) was added to a N,N-dimethylformamide solution (10 ml) of methyl 6-[(4-acetyl-2-ethyl-5-hydroxyphenoxy)methyl]pyridine-2-carboxylate (500 mg, 1.4 mmol) and methyliodide (5 ml), and the mixture was stirred at 70° C. for 2 hours.

The reaction mixture was poured into water and extracted with ethylacetate and washed with saturated aqueous sodium chloride. Then, the extract was dried, concentrated and chromatographed on silica gel to give methyl 6-[(4-acetyl-2-ethyl-5-methoxyphenoxy)methyl]pyridine-2-carboxylate.

REFERENCE EXAMPLE 6

According to the procedure of Reference Example 2, 6-[(4-acetyl-2-ethyl-5-methoxyphenoxy)methyl]pyridine-2-carboxylic acid was obtained by hydrolysis of methyl 6-[(4-acetyl-2-ethyl-5-methoxyphenoxy)methyl]pyridine-2-carboxylate.

REFERENCE EXAMPLE 7

According to the procedure of Reference Example 5, methyl 6-[(4-acetyl-2-n-propyl-3-methoxyphenoxy)methyl]pyridine-2-carboxylate was obtained from methyl 6-[(4-acetyl-3-hydroxy-2-n-propylphenoxy)methyl]-pyridine-2-carboxylate.

REFERENCE EXAMPLE 8

According to the procedure of Reference Example 2, 6-[(4-acetyl-2-n-propyl-3-methoxyphenoxy)methyl]-pyridine-2-carboxylic acid was obtained by hydrolysis of methyl 6-[(4-acetyl-2-n-propyl-3-methoxyphenoxy)-methyl]pyridine-2-carboxylate.

REFERENCE EXAMPLE 9 a compound included in formula [XVI]

A mixture of 6-methylpyridine-2-carboxylic acid (13.7 g, 100 mmol) and thionyl chloride (40 ml) was stirred at 70° C. for 1 hour. The mixture was dried, and dichloromethane (40 ml) was added to the residue. The solution was added to a dichloromethane solution of 2-amino-2-methyl-propanol (36.0 g, 400 mmol), and stirred. The mixture was washed with water, and dried over anhydrous magnesium sulfate. The extract was concentrated and chromatographed on silica gel to give an amide compound. 4,4-Dimethyl-2-oxazoline compound was obtained by reacting the amide compound and thionyl chloride in dichloromethane. 4,4-Dimethyl-2-oxazoline compound was reacted with n-butyl lithium at −78° C. in anhydrous tetrahydrofuran, and chloroethyl phenyl ether (782 mg, 5 mmol) was added. Purified alkylated compound was treated with ethanol saturated with HCl to give ethyl 6-(3-chloropropyl)pyridine-2-carboxylate.

REFERENCE EXAMPLE 10 a compound included in formula [II]

According to the procedure of Reference Examples 1,2, 6-[3-(4-acetyl-2-ethyl-5-hydroxyphenoxy)propyl]-pyridine-2-carboxylic acid was obtained from ethyl 6-(3-chloropropyl)pyridine-2-carboxylate and 5-ethyl-2,4-dihydroxyacetophenone.

TABLE 48

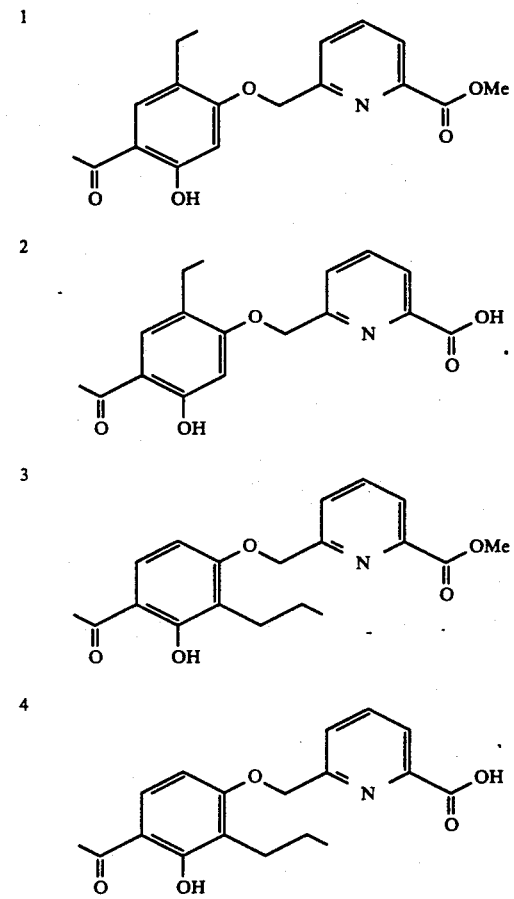

TABLE 49

| | $^1$H-NMR δ ppm |
|---|---|
| 1 | (solvent:CDCL$_3$) 0.99(3H, J=7.4Hz), 1.62(2H, tq, J=7.4Hz, J=7.4Hz), 2.57(3H, s), 2.76(2H, t, J=7.4Hz), 4.04(3H, s), 5.39(2H, s), 6.46(1H, d, J=8.9Hz), 7.59(1H, d, J=8.9Hz), 7.79(1H, d, J=6.6Hz), 7.92(1H, dd, J=6.6Hz, J=7.9Hz), 8.10(1H, d, J=7.9Hz) |
| 2 | (solvent:CDCL$_3$) 1.26(3H, t, J=7.6Hz), 2.59(3H, S), 2.68(2H, q, J=7.6Hz), 5.30(2H, s), 6.43(1H, s), 7.51(1H, s), 7.78(1H, d, J=6.9Hz), 8.04(1H, dd, J=6.9Hz, J=7.9Hz), 8.22(1H, d, J=7.9Hz) |
| 3 | (solvent:CDCL$_3$) 0.99(3H, t, J=7.4Hz), 1.62(2H, tq, J=7.4Hz, J=7.4Hz), 2.57(3H, s), 2.76(2H, t, J=7.4Hz), 4.04(3H, s), 5.39(2H, s), 6.46(1H, d, J=8.9Hz), 7.59(1H, d, J=8.9Hz), 7.79(1H, d, J=6.6Hz), 7.92(1H, dd, J=6.6Hz, J=7.9Hz), 8.10(1H, d, J=7.9Hz) |
| 4 | (solvent:CDCL$_3$) 0.99(3H, t, J=7.4Hz), 1.62(2H, tq, J=7.4Hz, J=7.4Hz), 2.57(3H, s), 2.76(2H, t, J=7.4Hz), 5.34(2H, s), 6.45(1H, d, J=8.9Hz), 7.60(1H, d, J=8.9Hz), 7.79(1H, dd, J=1.0Hz, J=6.9Hz), 8.04(1H, dd, J=6.9Hz, J=7.4Hz), 8.21(1H, dd, J=1.0Hz, J=7.4Hz) |

TABLE 50

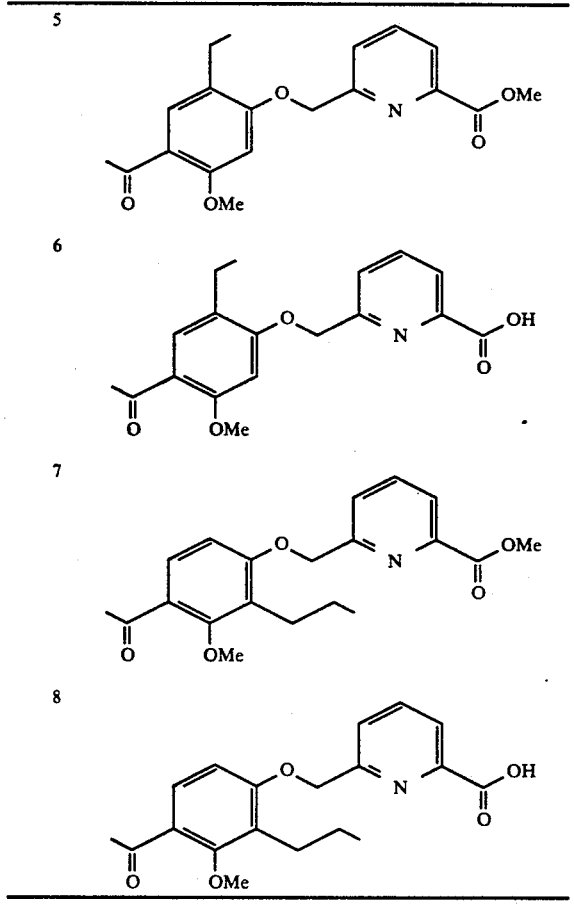

TABLE 51

| | ¹H-NMR δ ppm |
|---|---|
| 5 | (solvent:CDCL₃) 1.24(3H, t, J=7.6Hz), 2.58(3H, s), 2.70(2H, q, J=7.6Hz), 3.86(3H, s), 4.04(3H, s), 5.40(2H, s), 7.72(1H, s), 7.79(1H, d, J=7.9Hz), 7.94(1H, dd, J=7.9Hz), J=7.6Hz), 8.11(1H, d, J=7.6Hz) |
| 6 | (solvent:CDCL₃) 1.24(3H, t, J=7.4Hz), 2.57(3H, s), 2.69(2H, q, J=7.4Hz), 3.90(3H, s), 5.40(2H, s), 6.64(1H, s), 7.65(1H, s), 7.80(1H, d, J=7.3Hz), 8.01(1H, dd, J=7.6Hz, J=7.6Hz), 8.13(1H, d, J=7.9Hz) |
| 7 | (solvent:CDCL₃) 1.02(3H, t, J=7.5Hz), 1.66(2H, q, J=7.6Hz), 2.61(3H, s), 2.75(2H, t, J=7.8Hz), 3.78(3H, s), 5.31(2H, s), 6.70(1H, d, J=8.6Hz), 7.56(1H, d, J=8.9Hz), 7.90(1H, d, J=7.9Hz), 8.04(1H, dd, J=7.6Hz, J=7.9Hz), 8.21(1H, d, J=7.6Hz) |
| 8 | (solvent:CDCL₃) 1.02(3H, t, J=7.6Hz), 1.65(2H, q, J=7.7Hz), 2.62(3H, s), 2.75(2H, t, J=7.8Hz), 3.78(3H, s), 5.31(2H, s), 6.70(1H, d, J=8.6Hz), 7.56(1H, d, J=8.9Hz), 7.90(1H, d, J=7.9Hz), 8.04(1H, dd, J=7.6Hz, J=7.9Hz), 8.21(1H, d, J=7.6Hz) |

EXAMPLE 1

A mixture of 6-[(4-acetyl-2-ethyl-5-hydroxyphenoxy)methyl]pyridine-2-carboxylic acid (63 mg, 0.20 mmol), 1-ethyl-3-(3-dimethylaminopropyl)carbodiimide hydrochloride (40 mg, 0.20 mmol), 1-hydroxybenzotriazole (30 mg, 0.22 mmol), 2-aminothiazole-4-carboxamide (35 mg, 0.24 mg) and triethylamine (20 mg, 0.20 mmol) in a mixed solution of dichloromethane (2 ml) and N,N-dimethylformamide (2 ml) was stirred at room temperature for 44 hours. The reaction mixture was poured into water and extracted with ethyl acetate (80 ml×3). The extract was dried over anhydrous magnesium sulfate, concentrated under reduced pressure and chromatographed on silica gel to give 2-[6-[(4-acetyl-2-ethyl-5-hydroxyphenoxy)methyl]pyridine-2-carboxamide]thiazol-4-ylcarboxamide.

EXAMPLE 2~35,62,88,90,92

According to the procedure of Example 1, the compounds (Example 2~35,62,88,90,92) were obtained.

EXAMPLE 36

Ethyl 2-[6-[(4-acetyl-2-ethyl-5-hydroxyphenoxy)methyl]pyridine-2-carboxamide]thiazole-4-ylcarboxylate (24 mg, 0.05 mmol) was suspended in methanol (1.5 ml), followed by addition of one-second normal sodium hydroxide (1.0 ml).

After the solution was stirred for 2 hr, it was made acidic with one-second normal potassium bisulfate. Precipitated crystals were separated by filtration, and washed with water, and dried to give 2-[6-[(4-acetyl-2-ethyl-5-hydroxyphenoxy)methyl]pyridine-2-carboxamide]thiazol-4-ylcarboxylic acid.

EXAMPLE 37~52,61,87,89,91

According to the procedure of Example 36, the compounds (Example 37~52, 61, 87, 89, 91) were obtained.

EXAMPLE 54~56,64,67,68,70,72,74,76,78,80,82,84,86,94,96,100, 102,104,106,108,112,114,115,116–121,123,126,127,138,1-41

According to the procedure of Example 1, the title compounds were obtained.

EXAMPLE 53,57~60,63,65,69,71,73,75,77,79,81,83,85,93,95,99, 101,105,107,111,113,122,130

According to the procedure of Example 36, the title compounds were obtained.

EXAMPLE 98

Ethyl 2-[6-[(4-acetyl-2-ethyl-5-hydroxyphenoxy)methyl]pyridine-2-carboxamide]pyridine-6-ylcarboxylate (280 mg, 0.60 mM) was dissolved in dichloromethane (5 ml), followed by addition of m-chloroperbenzoic acid (124 mg, 0.72 mM). After being stirred at room temperature for 16 hours, the reaction mixture was washed with aqueous sodium sulfite-sodium bicarbonate, dried over anhydrous magnesium sulfate, and concentrated under reduced pressure to give ethyl 2-[6-[(4-acetyl-2-ethyl-5-hydroxyphenoxy)methyl]pyridine-2-carboxamide]pyridine-N-oxide-6-ylcarboxylate.

EXAMPLE 110,125,129,131,134,136,139,142

According to the procedure of Example 98, the title compounds were obtained.

EXAMPLE 97,109,124,128,132,133,135,137,140

According to the procedure of Example 36, the title compounds were obtained.

EXAMPLE 143~178,212,214,216,218,222,225,226

According to the procedure of Example 1, the title compounds were obtained.

EXAMPLE 179~211,213,215,223,224

According to the procedure of Example 36, the title compounds were obtained.

TABLE 52

| Ex. No. | Structural formula |
|---|---|
| 1 | (structure) |
| 2 | (structure) |
| 3 | (structure) |
| 4 | (structure) |
| 5 | (structure) |

TABLE 53

| | ¹H-NMR δ ppm |
|---|---|
| 1 | (solvent:CDCL₃) 1.28(3H, t, J=7.6Hz), 2.60(3H, s), 2.71(2H, q, J=7.6Hz), 5.34(1H, s), 5.55(1H, bs), 6.48(1H, s), 7.05(1H, bs), 7.52(1H, s), 7.77(1H, d, J=7.3Hz), 9.90(1H, s), 8.04(1H, dd, J=6.6Hz, J=7.3Hz), 8.28(1H, d, J=7.3Hz), 10.98(1H, bs), 12.70(1H, s) |
| 2 | (solvent:CDCL₃) 1.27(3H, t, J=7.6Hz), 2.59(3H, s), 2.70(2H, q, J=7.6Hz), 3.69(2H, s), 5.32(2H, s), 5.43(1H, bs), 6.45(1H, s), 6.60(1H, bs), 6.86(1H, s), 7.51(1H, s), 7.74(1H, d, J=6.9Hz), 8.02(1H, t, J=6.9Hz), 8.27(1H, d, J=6.9Hz), 12.68(1H, s) |
| 3 | (solvent:CDCL₃) 1.26(3H, t, J=7.6Hz), 2.58(3H, s), 2.69(2H, q, J=7.6Hz), 3.70(2H, s), 3.81(3H, s), 5.39(1H, s), 5.43(1H, bs), 6.46(1H, s), 6.70(1H, bs), 6.88(1H, s), 7.49(1H, s), 7.64(1H, dd, J=1.0Hz, J=7.9Hz), 7.79(1H, dd, J=7.6Hz, J=7.9Hz), 7.95(1H, dd, J=1.0Hz, J=7.6Hz), 12.65(1H, s) |
| 4 | (solvent:CDCL₃) 1.26(3H, t, J=7.6Hz), 1.44(3H, t, J=6.9Hz), 2.58(3H, s), 2.69(2H, q, J=7.6Hz), 3.69(2H, S), 4.36(2H, q, J=6.9Hz) 5.25(1H, s), 5.44(1H, bs), 6.43(1H, s), 6.67(1H, bs), 6.89(1H, s), 7.49(1H, s), 7.64(1H, d, J=7.9Hz), 7.74(1H, dd, J=6.9Hz, J=7.9Hz), 7.94(1H, dd, J=6.9Hz, J=7.9Hz), 12.66(1H, s) |
| 5 | (solvent:CDCL₃) 0.78(6H, d, J=6.6Hz), 1.26(3H, t, J=7.6Hz), 2.0-2.2(1H, m), 2.58(3H, s), 2.68(2H, q, J=7.6Hz), 3.66(2H, s), 4.33(2H, d, J=7.3Hz), 5.21(2H, s), 5.84(1H, bs), |

TABLE 53-continued

| | ¹H-NMR δ ppm |
|---|---|
| | 6.42(1H, s), 6.60(1H, bs), 6.88(1H, s), 7.49(1H, s), 7.62(1H, d, J=7.6Hz), 7.74(1H, d, J=7.9Hz), 7.93(1H, dd, J=7.6Hz, J=7.9Hz), 12.66(1H, s) |

TABLE 54

| Ex. No. | Structural formula |
|---|---|
| 6 | (structure) |
| 7 | (structure) |
| 8 | (structure) |
| 9 | (structure) |
| 10 | (structure) |

TABLE 55

| | ¹H-NMR δ ppm |
|---|---|
| 6 | (solvent:CDCL₃) 1.28(3H, t, J=7.6Hz), 2.59(3H, s), 2.70(2H, q, J=7.6Hz), 2.84(3H, d, J=5.0Hz), 3.67(2H, s), 5.33(2H, s), 6.45(1H, s), 6.48(1H, bs), 6.85(1H, s), 7.51(1H, s), 7.74(1H, d, J=6.6Hz), 8.02(1H, t, J=6.6Hz), 8.27(1H, d, J=6.6Hz), 11.06(1H, bs), 12.70(1H, s) |
| 7 | (solvent:CDCL₃) 1.27(3H, t, J=7.6Hz), 2.59(3H, s), 2.70(2H, q, J=7.6Hz), 3.01(3H, s), 3.11(1H, s), 3.83(2H, s), 5.28(2H, s), 6.43(1H, s), 6.86(1H, b), 7.51(1H, s), 7.72(1H, dd, J=1.0Hz, J=7.9Hz), 8.00(1H, t, J=7.9Hz), 8.25(1H, dd, J=1.0Hz, J=7.9Hz), 11.08(1H, bs), 12.70(1H, s) |
| 8 | (solvent:CDCL₃) 1.15(6H, d, J=6.6Hz), 1.27(3H, t, |

TABLE 55-continued

| ¹H-NMR | δ ppm |
|---|---|

J=7.6Hz), 2.59(3H, s), 2.70(2H, q, J=7.6Hz), 3.63(2H, s), 4.0–4.2(1H, m), 5.32(1H, s), 6.06(1H, bs), 6.45(1H, s), 6.85(1H, s), 7.51(1H, s), 7.74(1H, d, J=7.9Hz), 8.02(1H, t, J=7.9Hz), 8.27(1H, d, J=7.9Hz), 11.06(1H, bs), 12.70(1H, s)

9 (solvent:CDCL₃) 1.27(3H, t, J=7.6Hz), 1.31(3H, s), 1.34(3H, s), 2.59(3H, s), 2.70(2H, q, J=7.6Hz), 3.1–3.2(1H, m), 5.30(2H, s), 6.44(1H, s), 6.62(1H, s), 7.51(1H, s), 7.71(1H, d, J=7.9Hz), 7.99(1H, dd, J=6.6Hz, J=7.9Hz), 8.26(1H, d, J=6.6Hz), 11.05(1H, bs), 12.67(1H, s)

10 (solvent:CDCL₃) 1.23(3H, t, J=7.6Hz), 2.60(3H, s), 2.65(2H, q, J=7.6Hz), 5.49(2H, s), 6.64(1H, s), 7.35–7.55(2H, m), 7.6–7.8(3H, m), 8.0–8.3(5H, m), 10.59(1H, bs), 12.60(1H, s)

TABLE 56

| Ex. No. | Structural formula |
|---|---|
| 11 | |
| 12 | |
| 13 | |

TABLE 56-continued

| Ex. No. | Structural formula |
|---|---|
| 14 | 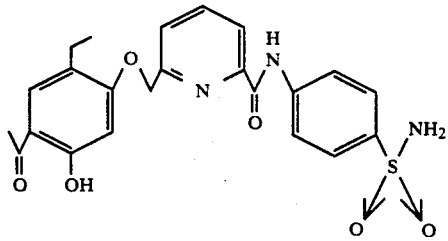 |
| 15 | 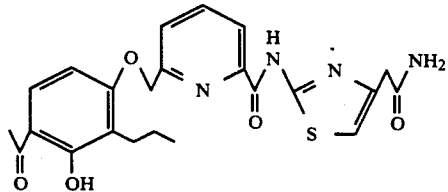 |

TABLE 57

| | ¹H-NMR δ ppm |
|---|---|
| 11 | (solvent:CDCL₃) 1.22(3H, t, J=7.6Hz), 2.58(3H, s), 2.67(2H, q, J=7.6Hz), 5.49(1H, s), 6.64(1H, s), 7.53(1H, bs), 7.71(1H, s), 7.80–7.85(1H, m), 8.1–8.4(5H, m), 8.85–8.90(1H, m), 10.63(1H, bs), 12.56(1H, s) |
| 12 | (solvent:CDCL₃) 1.20(3H, t, J=7.6Hz), 2.58(2H, s), 2.64(2H, q, J=7.6Hz), 5.47(2H, s), 6.62(1H, s), 7.30(2H, s), 7.71(1H, s), 7.75–7.90(3H, m), 8.0–8.2(4H, m), 10.75(1H, bs), 12.56(1H, s) |
| 13 | (solvent:CDCL₃) 1.00(3H, t, J=7.4Hz), 1.63(2H, tq, J=7.4Hz, J=7.4Hz), 2.58(3H, s), 2.77(2H, t, J=7.4Hz), 3.69(2H, s), 5.36(2H, s), 5.40(1H, bs), 6.47(1H, d, J=9.2Hz), 6.50(1H, bs), 6.87(1H, s), 7.62(1H, d, J=9.2Hz), 7.76(1H, d, J=7.9Hz), 8.02(1H, dd, J=7.9Hz, J=7.9Hz), 8.26(1H, d, J=7.9Hz) |
| 14 | (solvent:CDCL₃) 1.27(3H, t, J=7.6Hz) 1.43(3H, t, J=7.1Hz), 2.59(3H, s), 2.70(2H, q, J=7.6Hz), 4.45(2H, q, J=7.1Hz), 5.28(1H, s), 6.43(1H, s), 7.52(1H, s), 7.73(1H, d, J=7.9Hz), 7.94(1H, d, J=0.7Hz), 8.01(1H, t, J=7.9Hz), 8.25(1H, d, J=7.9Hz), 11.32(1H, bs), 12.66(1H, s) |
| 15 | (solvent:CDCL₃) 1.27(3H, t, J=7.6Hz), 1.30(3H, t, J=7.3Hz), 2.59(3H, s), 2.70(2H, q, J=7.6Hz), 3.76(2H, d, J=0.7Hz), 4.22(2H, q, J=7.3Hz), 5.28(1H, s), 6.43(1H, s), 6.90(1H, d, J=0.7Hz), 7.51(1H, s), 7.72(1H, d, J=7.9Hz), 8.00(1H, dd, J=7.6Hz, J=7.9Hz), 8.25(1H, d, J=7.6Hz), 11.11(1H, bs), 12.67(1H, s) |

TABLE 58

| Ex. No. | Structural formula |
|---|---|
| 16 | |
| 17 | |

TABLE 58-continued

| Ex. No. | Structural formula |
|---|---|
| 18 | (structure: acetyl-hydroxy-ethylphenyl-O-CH2-pyridine-C(O)-N(Et)-C(S)=N-C(=CH-)-CH2-C(O)-OEt) |
| 19 | (structure: acetyl-hydroxy-ethylphenyl-O-CH2-pyridine-C(O)-N(iBu)-C(S)=N-C(=CH-)-CH2-C(O)-OEt) |
| 20 | (structure: acetyl-hydroxy-ethylphenyl-O-CH2-pyridine-C(O)-NH-C(S)=N-C(=C(CH3)-)-CH2-C(O)-OEt) |

TABLE 59

| | $^1$H-NMR   δ ppm |
|---|---|
| 16 | (solvent:CDCL$_3$) 1.25(3H, t, J=7.3Hz), 1.27(3H, t, J=7.4Hz), 2.59(3H, s), 2.65-2.80(4H, m), 3.05(2H, t, J=7.3Hz), 4.15(2H, q, J=7.3Hz), 5.30(2H, s), 6.44(1H, s), 6.69(1H, s), 7.51(1H, s), 7.71(1H, d, J=7.7Hz), 7.97(1H, t, J=7.7Hz), 8.24(1H, d, J=7.7Hz), 11.05(1H, bs), 12.67(1H, s) |
| 17 | (solvent:CDCL$_3$) 1.27(3H, t, J=7.6Hz), 1.43(3H, t, J=7.1Hz), 2.59(3H, s), 2.70(2H, q, J=7.6Hz), 4.45(2H, q, J=7.1Hz), 5.28(1H, s) 6.43(1H, s), 7.52(1H, s), 7.73(1H, d, J=7.9Hz), 7.94(1H, d, J=0.7Hz), 8.01(1H, t, J=7.9Hz), 8.25(1H, d, J=7.9Hz), 11.32(1H, bs), 12.66(1H, s) |
| 18 | (solvent:CDCL$_3$) 1.26(3H, t, J=7.6Hz), 1.28(3H, t, J=7.1Hz), 1.40(3H, t, J=6.9Hz), 2.58(3H, s), 2.69(2H, q, J=7.6Hz), 3.76(2H, d, J=0.7Hz), 4.20(2H, q, J=7.1Hz), 4.32(2H, q, J=6.9Hz), 5.25(1H, s), 6.44(1H, s), 6.92(1H, s), 7.49(1H, s), 7.62(1H, d, J=7.6Hz), 7.70(1H, d, J=6.9Hz), 7.92(1H, dd, J=6.9Hz, J=7.6Hz), 12.65(1H, s) |
| 19 | (solvent:CDCL$_3$) 0.76(6H, d, J=6.6Hz), 1.26(3H, t, J=7.6Hz), 1.27(3H, t, J=7.1Hz), 2.0-2.2(1H, m), 2.58(3H, s), 2.68(2H, q, J=7.6Hz), 3.74(2H, s), 4.18(2H, d, J=7.1Hz), 4.28(2H, d, J=6.9Hz), 5.21(2H, s), 6.43(1H, s), 6.91(1H, s), 7.49(1H, s), 7.58(1H, d, J=7.9Hz), 7.71(1H, d, J=7.9Hz), 7.90(1H, t, J=7.9Hz), 12.63(1H, s) |
| 20 | (solvent:CDCL$_3$) 1.27(3H, t, J=7.4Hz), 1.29(3H, t, J=7.3Hz), 2.33(3H, s), 2.59(3H, s), 2.69(2H, q, J=7.4Hz), 3.73(2H, s), 4.20(2H, q, J=7.3Hz), 5.27(2H, s), 6.43(1H, s), 7.51(1H, s), 7.71(1H, d, J=7.9Hz), 7.99(1H, t, J=7.9Hz), 8.24(1H, d, J=7.9Hz), 10.98(1H, bs), 12.67(1H, s) |

TABLE 60

| Ex. No. | Structural formula |
|---|---|
| 21 | (structure: acetyl-hydroxy-ethylphenyl-O-CH2-pyridine-C(O)-NH-C(S)=N-N= ring with CH2-C(O)-OEt substituent) |
| 22 | (structure: acetyl-hydroxy-ethylphenyl-O-CH2-pyridine-C(O)-NH-C(S)=N-N= ring with CH2CH2-C(O)-OMe substituent) |

TABLE 60-continued

| Ex. No. | Structural formula |
|---|---|
| 23 | (structure: 2-ethyl-4-acetyl-5-hydroxyphenoxymethyl pyridine-6-carboxamide linked to 3-(ethoxycarbonylmethyl)phenyl) |
| 24 | (structure: 2-ethyl-4-acetyl-5-hydroxyphenoxymethyl pyridine-6-carboxamide linked to 4-(ethoxycarbonylmethyl)phenyl) |
| 25 | (structure: 2-ethyl-4-acetyl-5-hydroxyphenoxymethyl pyridine-6-carboxamide linked to 6-(ethoxycarbonylmethyl)pyridin-2-yl) |

TABLE 61

| | $^1$H-NMR δ ppm |
|---|---|
| 21 | (solvent:CDCL$_3$) 1.27(3H, t, J=6.7Hz), 1.32(3H, t, J=7.1Hz), 2.59(3H, s), 2.71(2H, J=7.1Hz), 4.16(2H, s), 4.27(2H, q, J=7.6Hz) 5.32(2H, s), 6.44(1H, s), 7.52(1H, s), 7.75(1H, d, J=7.6Hz), 8.02(1H, t, J=7.6Hz), 8.26(1H, d, J=7.6Hz), 11.21(1H, bs), 12.67(1H, s) |
| 22 | (solvent:CDCL$_3$) 1.27(3H, t, J=7.4Hz), 2.58(3H, s), 2.70(2H, q, J=7.4Hz), 2.93(2H, t, J=7.3Hz), 3.40(2H, t, J=7.3Hz), 3.73(3H, s), 5.32(2H, s), 6.43(1H, s), 7.51(1H, s), 7.75(1H, d, J=7.9Hz), 8.01(1H, t, J=7.9Hz), 8.24(1H, d, J=7.9Hz), 11.18(1H, bs), 12.66(1H, s) |
| 23 | (solvent:CDCL$_3$) 1.27(3H, t, J=7.3Hz), 1.27(3H, t, J=7.3Hz), 2.59(3H, s), 2.70(2H, q, J=7.3Hz), 3.66(2H, s), 4.17(2H, q, J=7.3Hz) 5.32(2H, s), 6.52(1H, s), 7.0–7.1(1H, m), 7.3–7.4(1H, m), 7.51(1H, s), 7.65–7.7(2H, m), 7.97(1H, t, J=7.7Hz), 8.26(1H, dd, J=1.0Hz, J=7.7Hz), 9.92(1H, bs), 12.68(1H, s) |
| 24 | (solvent:CDCL$_3$) 1.26(3H, t, J=7.1Hz), 1.27(3H, t, J=7.6Hz), 2.59(3H, s), 2.70(2H, q, J=7.6Hz), 3.62(2H, s), 4.16(2H, q, J=7.1Hz) 5.32(2H, s), 6.51(1H, s), 7.32(1H, d, J=8.6Hz), 7.51(1H, s), 7.67(1H, d, J=7.3Hz), 7.75(1H, d, J=8.6Hz), 7.98(1H, dd, J=7.3Hz, J=7.6Hz), 8.27(1H, d, J=7.6Hz), 9.90(1H, bs), 12.68(1H, s) |
| 25 | (solvent:CDCL$_3$) 1.28(3H, t, J=7.6Hz), 1.29(3H, t, J=7.3Hz), 2.59(3H, s), 2.71(2H, q, J=7.6Hz), 3.80(2H, s), 4.21(2H, q, J=7.3Hz) 5.34(2H, s), 6.47(1H, s), 7.09(1H, d, J=6.9Hz), 7.51(1H, s), 7.65–7.85(2H, m), 7.97(1H, t, J=7.6Hz), 8.26(1H, t, J=7.6Hz), 8.30(1H, t, J=7.6Hz), 10.37(1H, bs), 12.66(1H, s) |

TABLE 62

| Ex. No. | Structural formula |
|---|---|
| 26 | (structure: 2-ethyl-4-acetyl-5-methoxyphenoxymethyl pyridine-6-carboxamide linked to thiazole with ethoxycarbonylmethyl side chain) |
| 27 | (structure: 2-ethyl-4-acetyl-5-methoxyphenoxymethyl pyridine-6-carboxamide linked to 6-(ethoxycarbonylmethyl)pyridin-2-yl) |

TABLE 62-continued

| Ex. No. | Structural formula |
|---------|--------------------|
| 28 | (structure) |
| 29 | (structure) |
| 30 | (structure) |

TABLE 63

| | ¹H-NMR δ ppm |
|---|---|
| 26 | (solvent:CDCL₃) 1.25(3H, t, J=7.3Hz), 1.30(3H, t, J=7.3Hz), 2.59(3H, s), 2.71(2H, q, J=7.5Hz), 3.77(2H, s), 3.92(3H, s), 4.22(2H, q, J=7.5Hz), 5.32(2H, s), 6.50(1H, s), 6.91(1H, s), 7.73(1H, s), 7.80(1H, d, J=7.6Hz), 8.03(1H, dd, J=7.9Hz, J=7.6Hz), 8.24(1H, d, J=7.6Hz), 11.18(1H, s) |
| 27 | (solvent:CDCL₃) 1.26(3H, t, J=7.4Hz), 1.28(3H, t, J=7.4Hz), 2.59(3H, s), 2.72(2H, q, J=7.5Hz), 3.80(2H, s), 3.92(3H, s), 4.21(2H, q, J=7.5Hz), 5.38(2H, s), 6.57(1H, s), 7.10(1H, dd, J=7.0Hz, J=0.7Hz), 7.73(1H, s), 7.76(1H, dd, J=8.3Hz, J=7.9Hz), 7.77(1H, dd, J=7.9Hz, J=1.0Hz), 8.00(1H, dd, J=7.6Hz, J=7.9Hz), 8.27(1H, dd, J=7.9Hz, J=1.0Hz), 8.37(1H, d, J=8.3Hz), 10.40(1H, s) |
| 28 | (solvent:CDCL₃) 1.00(3H, t, J=7.4Hz), 1.30(3H, t, J=7.1Hz), 1.63 (2H, tq, J=7.9Hz, J=7.3Hz), 2.58(3H, s), 2.77(2H, t, J=7.6Hz), 3.77(2H, s), 4.22(2H, q, J=7.0Hz), 5.32(1H, s) 6.46(1H, d, J=8.9Hz), 6.91(1H, s), 7.62(1H, d, J=8.9Hz), 7.74(1H, d, J=7.9Hz), 8.00(1H, dd, J=7.6Hz, J=7.9Hz), 8.24(1H, dd, J=7.6Hz, J=0.6Hz) |
| 29 | (solvent:CDCL₃) 1.00(3H, t, J=7.4Hz), 1.29(3H, t, J=7.2Hz), 1.64(2H, tq, J=7.6Hz, J=7.2Hz), 2.58(3H, s), 2.78(2H, t, J=7.2Hz), 3.81(2H, s), 4.21(2H, q, J=7.0Hz), 5.38(2H, s), 6.50(1H, d, J=8.9Hz), 7.10(1H, dd, J=7.3Hz, J=0.7Hz), 7.62(1H, d, J=8.9Hz), 7.70(1H, d, J=7.9Hz), 7.76(1H, dd, J=8.0Hz, J=7.9Hz), 7.97(1H, dd, J=7.9Hz, J=7.6Hz), 8.25(1H, d, J=6.9Hz), 8.36(1H, d, J=7.6Hz) |
| 30 | (solvent:CDCL₃) 1.03(3H, t, J=7.3Hz), 1.64(2H, tq, J=7.6Hz, J=7.8Hz), 2.59(3H, s), 2.74(2H, t, J=8.0Hz), 3.78(3H, s), 3.82(2H, s), 5.31(2H, s), 6.71(1H, d, J=8.9Hz), 6.83(1H, s), 7.53(1H, d, J=8.9Hz), 7.70(1H, d, J=7.6Hz), 7.97(1H, dd, J=7.6Hz, J=7.9Hz), 8.19(1H, d, J=7.6Hz) |

TABLE 64

| Ex. No. | Structural formula |
|---------|--------------------|
| 31 | (structure) |
| 32 | (structure) |

TABLE 64-continued

| Ex. No. | Structural formula |
|---|---|
| 33 | (structure) |
| 34 | (structure) |
| 35 | (structure) |

TABLE 65

| | ¹H-NMR | δ ppm |
|---|---|---|
| 31 | (solvent:CDCL₃) 1.03(3H, t, J=7.3Hz), 1.65(2H, tq, J=7.6Hz, J=7.9Hz), 2.63(3H, s), 2.76(2H, t, J=7.6Hz), 3.79(3H, s), 3.90(2H, s), 5.37(2H, s), 6.81(1H, d, J=8.6Hz), 7.06(1H, d, J=7.6Hz), 7.59(1H, d, J=8.9Hz), 7.75(1H, d, J=6.9Hz), 7.83(1H, dd, J=7.9Hz, J=7.9Hz), 8.01(1H, dd, J=7.9Hz, J=7.9Hz), 8.28(1H, d, J=6.9Hz), 8.37(1H, d, J=7.9Hz) | |
| 32 | (solvent:CDCL₃) 1.27(3H, t, J=7.6Hz), 1.28(3H, t, J=7.1Hz), 2.59(3H, s), 2.71(2H, q, J=7.6Hz), 3.72(2H, s), 4.17(2H, q, J=7.3Hz) 5.32(2H, s), 6.43(1H, s), 6.89(1H, s), 7.51(1H, s), 7.67(1H, dd, J=0.7Hz, J=8.2Hz), 8.29(1H, dd, J=2.3Hz, J=8.2Hz), 9.14(1H, dd, J=0.7Hz, J=2.3Hz), 9.58(1H, bs), 12.66(1H, s) | |
| 33 | (solvent:CDCL₃) 1.27(3H, t, J=7.6Hz), 1.32(3H, t, J=7.3Hz), 2.59(3H, s), 2.70(2H, q, J=7.6Hz), 4.30(2H, q, J=7.3Hz), 4.68(2H, s) 5.32(2H, s), 6.51(1H, s), 6.70–6.80(1H, m), 7.25–7.35(2H, m) 7.51(1H, s), 7.55–7.65(1H, m), 7.68(1H, d, J=7.6Hz), 7.98(1H, dd, J=6.6Hz, J=7.6Hz), 8.26(1H, d, J=6.6Hz), 9.90(1H, bs), 12.67(1H, s) | |
| 34 | (solvent:CDCL₃) 1.27(3H, t, J=7.6Hz), 1.31(3H, t, J=7.3Hz), 2.59(3H, s), 2.70(2H, q, J=7.6Hz), 4.26(2H, q, J=7.3Hz), 4.63(2H, s) 5.31(2H, s), 6.51(1H, s), 6.96(2H, d, J=9.1Hz), 7.51(1H, s), 7.66(1H, d, J=8.6Hz), 7.71(2H, d, J=9.1Hz), 7.97(1H, dd, J=7.6Hz, J=8.6Hz), 8.26(1H, d, J=7.6Hz), 9.82(1H, s); 12.67(1H, s) | |
| 35 | (solvent:CDCL₃) 1.27(3H, t, J=7.3Hz), 1.27(3H, t, J=7.3Hz), 2.59(3H, s), 2.70(2H, q, J=7.6Hz), 3.73(2H, s), 4.07(2H, d, J=5.3Hz) 4.20(2H, q, J=7.3Hz), 5.32(2H, s), 6.45(1H, s), 6.88(1H, s), 7.03(1H, b), 7.51(1H, s), 7.74(1H, dd, J=1.0Hz, J=7.6Hz), 8.01(1H, dd, J=7.6Hz, J=7.9Hz), 8.25(1H, dd, J=1.0Hz, J=7.9Hz), 11.08(1H, bs), 12.67(1H, s) | |

TABLE 66

| Ex. No. | Structural formula |
|---|---|
| 36 | (structure) |
| 37 | (structure) |

TABLE 66-continued

| Ex. No. | Structural formula |
|---|---|
| 38 | 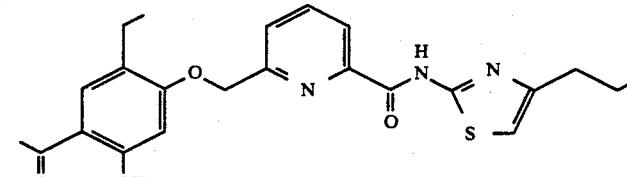 |
| 39 | 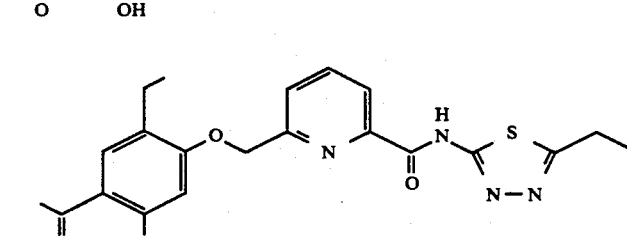 |
| 40 | 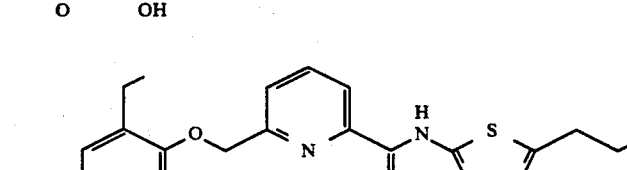 |

TABLE 67

| | ¹H-NMR δ ppm |
|---|---|
| 36 | (solvent:DMSO-d₆) 1.20(3H, J=7.6Hz), 2.59(3H, s), 2.63(2H, q, J=7.6Hz), 5.44(2H, s), 6.71(1H, s), 7.45(1H, s), 7.66(1H, S), 7.7–7.8(1H, m), 8.10–8.20(2H, m), 12.60(1H, bs) |
| 37 | (solvent:DMSO-d₆) 1.21(3H, t, J=7.6Hz), 2.58(3H, s), 2.65(2H, q, J=7.6Hz), 3.67(2H, s), 5.46(2H, s), 6.63(1H, s), 7.11(1H, s), 7.70(1H, s), 7.78(1H, dd, J=1.3Hz, J=7.3Hz), 12.04(1H, bs), 12.55(1H, s) |
| 38 | (solvent:DMSO-d₆) 1.21(3H, t, J=7.4Hz), 2.59(3H, s), 2.55–2.75(4H, m), 2.89(2H, t, J=7.6Hz), 5.47(2H, s), 6.63(1H, s), 6.95(1H, s), 7.70(1H, s), 7.78(1H, d, J=7.3Hz), 8.10–8.20(2H, m), 11.94(1H, bs), 12.57(1H, s) |
| 39 | (solvent:DMSO-d₆) 1.21(3H, t, J=7.4Hz), 2.58(3H, s), 2.65(2H, q, J=7.4Hz), 4.15(2H, s), 5.47(2H, s), 6.63(1H, s), 7.70(1H, s), 7.80(1H, d, J=6.9Hz), 8.10–8.20(2H, m), 12.50(1H, bs), 12.56(1H, s) |
| 40 | (solvent:DMSO-d₆) 1.21(3H, t, J=7.4Hz), 2.59(3H, s), 2.55–2.75(4H, m), 2.89(2H, t, J=7.6Hz), 5.47(2H, s), 6.63(1H, s), 6.95(1H, s), 7.70(1H, s), 7.78(1H, d, J=7.3Hz), 8.10–8.20(2H, m), 11.94(1H, bs), 12.57(1H, s) |

TABLE 68

| Ex. No. | Structural formula |
|---|---|
| 41 | 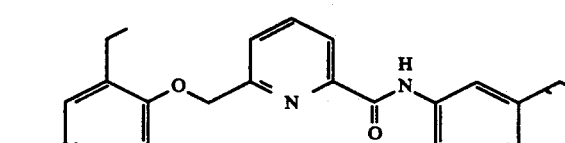 |
| 42 | 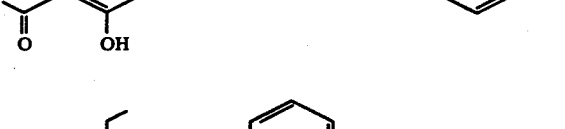 |

TABLE 68-continued

| Ex. No. | Structural formula |
|---|---|
| 43 | (structure: 4-acetyl-2-ethyl-5-hydroxyphenoxymethyl-pyridine-2-carboxamide linked to 6-(carboxymethyl)pyridin-2-yl) |
| 44 | (structure: 4-acetyl-2-ethyl-5-methoxyphenoxymethyl-pyridine-2-carboxamide linked to thiazole-carboxylic acid derivative) |
| 45 | (structure: 4-acetyl-2-ethyl-5-methoxyphenoxymethyl-pyridine-2-carboxamide linked to 6-(carboxymethyl)pyridin-2-yl) |

TABLE 69

| | $^1$H-NMR    δ ppm |
|---|---|
| 41 | (solvent:DMSO-d$_6$) 1.20(3H, t, J=7.6Hz), 2.58(3H, s), 2.65(2H, q, J=7.6Hz), 3.58(1H, s), 5.47(2H, s), 6.63(1H, s), 7.04(1H, d, J=7.9Hz), 7.33(1H, m), 7.7–7.8(4H, m), 8.1–8.2(2H, m), 10.41(1H, s), 12.56(1H, s) |
| 42 | (solvent:DMSO-d$_6$) 1.20(3H, t, J=7.6Hz), 2.58(3H, s), 2.65(2H, q, J=7.6Hz), 5.46(2H, s), 6.62(1H, s), 7.27(2H, d, J=8.2Hz) 7.65–7.85(4H, m), 8.05–8.20(2H, m), 8.10–8.20(2H, m), 10.40(1H, s) 12.56(1H, bs) |
| 43 | (solvent:DMSO-d$_6$) 1.23(3H, t, J=7.6Hz), 2.58(3H, s), 2.67(2H, q, J=7.6Hz), 3.71(2H, s), 5.49(2H, s), 6.65(1H, s), 7.17(1H, d, J=6.9Hz), 7.69(1H, s), 7.75–7.95(2H, m), 8.10–8.20(3H, m), 10.33(1H, s), 12.55(1H, bs) |
| 44 | (solvent:CDCL$_3$) 1.25(3H, t, J=7.4Hz), 2.57(3H, s), 2.70(2H, q, J=7.2Hz), 3.83(2H, s), 3.89(3H, s), 5.35(2H, s), 6.52(1H, s), 6.88(1H, s), 7.70(1H, s), 7.81(1H, d, J=7.6Hz), 8.03(1H, dd, J=7.9Hz, J=7.6Hz), 8.24(1H, d, J=7.6Hz) |
| 45 | (solvent:CDCL$_3$) 1.26(3H, t, J=6.7Hz), 2.59(3H, s), 2.72(2H, q, J=6.9Hz), 3.91(2H, s), 3.93(3H, s), 5.39(2H, s), 6.55(1H, s), 7.07(1H, d, J=7.3Hz), 7.74(1H, s), 7.83(1H, d, J=6.6Hz) 7.86(1H, dd, J=7.8Hz, J=7.6Hz), 8.04(1H, dd, J=7.9Hz, J=7.9Hz), 8.29(1H, d, J=6.6Hz), 8.41(1H, d, J=8.3Hz) |

TABLE 70

| Ex. No. | Structural formula |
|---|---|
| 46 | (structure: 4-acetyl-3-hydroxy-2-propylphenoxymethyl-pyridine-2-carboxamide linked to thiazole-carboxylic acid derivative) |
| 47 | (structure: 4-acetyl-3-hydroxy-2-propylphenoxymethyl-pyridine-2-carboxamide linked to 6-(carboxymethyl)pyridin-2-yl) |

TABLE 70-continued

| Ex. No. | Structural formula |
|---|---|
| 48 | (acetyl-methoxy-propyl-phenoxy)methyl-pyridine-carboxamide-thiazole-acetic acid structure |
| 49 | (acetyl-methoxy-propyl-phenoxy)methyl-pyridine-carboxamide-pyridine-acetic acid structure |
| 50 | (acetyl-ethyl-hydroxy-phenoxy)methyl-pyridine-carboxamide-thiazole-acetic acid structure |

TABLE 71

| ¹H-NMR | δ ppm |
|---|---|
| 46 | (solvent:DMSO-d₆) 0.92(3H, t, J=7.3Hz), 1.55(2H, tq, J=6.9Hz, J=7.7Hz), 2.52(3H, s), 2.67(2H, t, J=7.6Hz), 3.67(2H, s), 5.50(2H, s), 6.77(1H, d, J=9.2Hz), 7.11(1H, s), 7.76(1H, d, J=7.2Hz) 7.81(1H, d, J=8.9Hz), 8.11(1H, dd, J=7.6Hz, J=7.6Hz), 8.15(1H, d, J=7.6Hz) |
| 47 | (solvent:CDCL₃) 1.00(3H, t, J=7.4Hz), 1.64(2H, tq, J=7.6Hz, J=7.3Hz), 2.59(3H, s), 2.78(2H, t, J=7.6Hz), 3.91(2H, s), 5.40(2H, s), 6.55(1H, d, J=8.9Hz), 7.07(1H, d, J=6.6Hz), 7.63(1H, d, J=8.2Hz), 7.77(1H, d, J=6.9Hz), 7.85(1H, dd, J=7.9Hz, J=7.9Hz), 8.02(1H, dd, J=7.6Hz, J=7.9Hz), 8.27(H, d, J=6.9Hz), 8.39(1H, d, J=8.3Hz) |
| 48 | (solvent:CDCL₃) 1.03(3H, t, J=7.3Hz), 1.64(2H, tq, J=7.6Hz, J=7.8Hz), 2.59(3H, s), 2.74(2H, t, J=8.0Hz), 3.78(3H, s), 3.82(2H, s), 5.31(2H, s), 6.71(1H, d, J=8.9Hz), 6.83(1H, s), 7.53(1H, d, J=8.9Hz), 7.70(1H, d, J=7.6Hz), 7.97(1H, dd, J=7.6Hz, J=7.9Hz), 8.19(1H, d, J=7.6Hz) |
| 49 | (solvent:CDCL₃) 1.03(3H, t, J=7.3Hz), 1.65(2H, tq, J=7.6Hz, J=7.9Hz), 2.63(3H, s), 2.76(2H, t, J=7.6Hz), 3.79(3H, s), 3.90(2H, s), 5.37(2H, s), 6.81(1H, d, J=8.6Hz), 7.06(1H, d, J=7.6Hz), 7.59(1H, d, J=8.9Hz), 7.75(1H, d, J=6.9Hz), 7.83(1H, dd, J=7.9Hz, J=7.9Hz), 8.01(1H, dd, J=7.9Hz, J=7.9Hz), 8.28(1H, d, J=6.9Hz) |
| 50 | (solvent:DMSO-d₆) 1.20(3H, t, J=7.6Hz), 2.58(3H, s), 2.64(2H, q, J=7.6Hz), 3.66(2H, s), 5.38(2H, s), 6.57(1H, s), 7.06(1H, s), 7.66(1H, d, J=8.6Hz), 7.69(1H, s), 8.48(1H, dd, J=2.0Hz, J=8.6Hz), 9.22(1H, d, J=2.0Hz), 12.54(1H, s) |

TABLE 72

| Ex. No. | Structural formula |
|---|---|
| 51 | (acetyl-ethyl-hydroxy-phenoxy)methyl-pyridine-carboxamide-phenoxy-acetic acid (meta) structure |
| 52 | (acetyl-ethyl-hydroxy-phenoxy)methyl-pyridine-carboxamide-phenoxy-acetic acid (para) structure |

TABLE 72-continued

| Ex. No. | Structural formula |
|---|---|
| 53 | (structure shown) |
| 54 | (structure shown) |
| 55 | (structure shown) |

TABLE 73

| | $^1$H-NMR  δ ppm |
|---|---|
| 51 | (solvent: DMSO-d$_6$) 1.19(3H, t, J=7.6Hz), 2.58(3H, s), 2.64(2H, q, J=7.6Hz), 4.64(2H, s), 5.45(2H, s), 6.62(1H, s), 6.93(2H, d, J=8.2Hz), 7.65–7.85(4H, m), 8.05–8.20(2H, m), 10.35(1H, s), 12.55(1H, s) |
| 52 | (solvent:DMSO-d$_6$) 1.20(3H, t, J=7.6Hz), 2.58(3H, s), 2.64(2H, q, J=7.6Hz), 4.66(2H, s), 5.46(2H, s), 6.62(1H, s), 6.65–6.75(1H, m), 7.20–7.80(5H, m), 8.05–8.20(2H, m), 10.41(1H, s) 12.56(1H, s), |
| 53 | (solvent:DMSO-d$_6$) 1.21(3H, t, J=7.3Hz), 2.58(3H, s), 2.65(2H, q, J=7.3Hz), 3.60(2H, s), 3.79(2H, d, J=5.6Hz), 5.46(2H, s) 6.63(1H, s), 7.09(1H, s), 7.75–7.85(1H, m), 8.1–8.4(3H, m), 12.04(1H, bs), 12.56(1H, s) |
| 54 | (solvent:CDCL$_3$) 1.31(3H, t, J=7.6Hz), 1.52(2H, d, J=6.9Hz), 2.57(3H, s), 2.74(2H, q, J=7.6Hz), 3.71(2H, s), 4.60(1H, dq, J=7.6Hz, J=7.9Hz), 5.49(2H, s), 6.84(1H, s), 7.01(1H, d, J=7.3Hz), 7.51(1H, s), 7.63(1H, d, J=7.6Hz), 7.75(1H, dd, J=7.6Hz, J=8.2Hz), 7.93(1H, dd, J=7.6Hz, J=7.6Hz), 8.22(1H, d, J=7.9Hz), 8.33(1H, d, J=8.3Hz) |
| 55 | (solvent:CDCL$_3$) 1.27(3H, t, J=7.6Hz), 1.43(2H, d, J=7.3Hz), 2.59(3H, s), 2.71(2H, q, J=7.3Hz), 3.72(3H, s), 3.74(2H, s), 4.61(2H, dq, J=6.9Hz, J=7.2Hz), 5.39(2H, s), 6.49(1H, s), 7.06(1H, d, J=7.6Hz), 7.51(1H, s), 7.72(1H, d, J=7.6Hz), 7.76(1H, dd, J=7.2Hz, J=8.4Hz), 8.00(1H, dd, J=7.6Hz, J=7.9Hz), 8.27(1H, d, J=7.9Hz), 8.34(1H, d, J=8.6Hz) |

TABLE 74

| Ex. No. | Structural formula |
|---|---|
| 56 | (structure shown) |
| 57 | (structure shown) |

TABLE 74-continued

| Ex. No. | Structural formula |
|---|---|
| 58 | (structure) |
| 59 | (structure) |
| 60 | (structure) |

TABLE 75

| | ¹H-NMR δ ppm |
|---|---|
| 56 | (solvent:CDCL₃) 1.28(3H, t, J=7.4Hz), 2.59(3H, s), 2.54(2H, t, J=6.1Hz), 2.70(2H, t, J=7.4Hz), 3.55(3H, s), 3.56(2H, dd, J=5.9Hz, J=6.3Hz), 3.69(2H, s), 5.39(2H, s), 6.50(1H, s), 7.06(1H, d, J=7.6Hz), 7.51(1H, s), 7.73(1H, dd, J=7.9Hz, J=1.0Hz), 7.75(1H, dd, J=7.6Hz, J=7.9Hz), 7.99(1H, dd, J=7.6Hz, J=7.9Hz), 8.30(1H, d, J=7.9Hz, J=1.0Hz), 8.32(1H, d, J=8.3Hz), |
| 57 | (solvent:CDCL₃) 1.28(3H, t, J=7.6Hz), 2.60(3H, s), 2.72(2H, q, J=7.5Hz), 3.76(2H, s), 5.40(2H, s), 6.55(1H, s), 7.13(1H, d, J=7.3Hz), 7.54(1H, s), 7.76(1H, dd, J=7.3Hz, J=7.6Hz), 7.81(1H, d, J=7.6Hz), 8.02(1H, dd, J=7.9Hz, J=7.9Hz), 8.25(1H, d, J=7.3Hz), 8.31(1H, d, J=8.2Hz) |
| 58 | (solvent:CDCL₃) 1.31(3H, t, J=7.6Hz), 1.52(2H, d, J=6.9Hz), 2.57(3H, s), 2.74(2H, q, J=7.6Hz), 3.71(2H, s), 4.60(1H, dq, J=7.6Hz, J=7.9Hz), 5.49(2H, s), 6.84(1H, s), 7.01(1H, d, J=7.3Hz), 7.51(1H, s), 7.63(1H, d, J=7.6Hz), 7.75(1H, dd, J=7.6Hz, J=8.2Hz), 7.93(1H, dd, J=7.6Hz, J=7.6Hz), 8.22(1H, d, J=7.9Hz), 8.33(1H, d, J=8.3Hz) |
| 59 | (solvent:CDCL₃) 1.28(3H, t, J=7.6Hz), 2.58(3H, s), 2.60(2H, q, J=5.9Hz), 2.71(2H, q, J=7.9Hz), 3.70(2H, s), 3.60(2H, q, J=5.7Hz), 5.44(1H, s), 6.74(1H, s), 7.03(1H, d, J=7.6Hz) 7.50(1H, s), 7.73(1H, d, J=7.3Hz), 7.74(1H, dd, J=8.5Hz, J=7.3Hz), 8.00(1H, dd, J=7.9Hz, J=7.6Hz), 8.25(1H, d, J=7.6Hz), 8.31(1H, d, J=8.2Hz) |
| 60 | (solvent:CDCL₃) 1.29(3H, t, J=7.6Hz), 2.60(3H, s), 2.73(2H, q, J=7.5Hz), 2.85(1H, dd, J=17.2Hz, J=5.3Hz), 3.00(1H, dd, J=14.2Hz, J=4.6Hz), 3.76(2H, s), 4.78(1H, t, J=5.0Hz), 5.41(2H, s), 6.55(1H, s), 7.13(1H, d, J=7.6Hz), 7.55(1H, s), 7.74(1H, d, J=7.8Hz), 7.79(1H, dd, J=7.6Hz, J=8.2Hz), 8.02(1H, dd, J=7.6Hz, J=7.9Hz), 8.23(1H, d, J=6.9Hz), 8.30(1H, d, J=8.6Hz) |

TABLE 76

| Ex. No. | Structural formula |
|---|---|
| 61 | (structure) |
| 62 | (structure) |

TABLE 76-continued

| Ex. No. | Structural formula |
|---|---|
| 63 | |
| 64 | |
| 65 | |

TABLE 77

| | $^1$H-NMR δ ppm |
|---|---|
| 61 | (solvent:DMSO-d$_6$) 1.19(3H, t, J=7.6Hz), 2.59(3H, s), 2.64(2H, q, J=7.6Hz), 3.67(2H, s), 5.49(2H, s), 6.69(1H, s), 7.12(1H, s), 7.71(1H, s), 9.04(1H, s), 9.27(1H, s), 10.06(1H, s), 12.58(1H, br) |
| 62 | (solvent:CDCl$_3$) 1.26(3H, t, J=7.6Hz), 1.30(3H, t, J=7.3Hz), 2.60 (3H, s), 2.69(2H, q, J=7.6Hz), 3.76(2H, d, J=0.7Hz), 4.22(2H, q, J=7.3Hz), 5.33(2H, s), 6.47(1H, s), 6.94(1H, s), 7.53(1H, s), 9.08 (1H, s), 9.48(1H, s), 10.90(1H, br), 12.70(1H, s) |
| 63 | (solvent:DMSO-d$_6$) 1.19(3H, t, J=7.6Hz), 2.59(3H, s), 2.66(2H, q, J=7.6Hz), 2.89(1H, dd, J=8.3Hz, 15.0Hz), 3.00(1H, dd, J=5.3Hz, 15.0Hz), 3.58(2H, s), 4.4–4.5(1H, m), 5.49(2H, s), 6.68(1H, s), 6.94(1H, s), 7.00(1H, s), 7.71(1H, s), 7.87(1H, s), 8.33(1H, d, J=7.6Hz), 9.05(1H, s), 9.27(1H, s), 12.60(1H, br) |
| 64 | (solvent:CDCl$_3$) 1.20(3H, t, J=7.3Hz), 2.60(3H, s), 2.70(2H, q, J=7.3Hz), 3.1–3.2(2H, m), 3.72(3H, s), 3.75(2H, s), 4.8–4.9(1H, m), 5.36(2H, s), 6.48(1H, s), 6.79(1H, s), 6.91(1H, s), 7.53(1H, s), 7.56(1H, s), 9.10(1H, s), 9.48(1H, s), 12.78(1H, br) |
| 65 | (solvent:DMSO-d$_6$) 1.19(3H, t, J=7.6Hz), 2.59(3H, s), 2.6–2.7(4H, m), 3.61(2H, s), 4.5–4.6(1H, m), 5.49(2H, s), 6.69(1H, s), 7.08(1H, s), 8.35(1H, d, J=7.6Hz), 9.05(1H, s), 9.27(1H, s), 12.60(1H, s), |

TABLE 78

| Ex. No. | Structural formula |
|---|---|
| 66 | |
| 67 | |

TABLE 78-continued

| Ex. No. | Structural formula |
|---|---|
| 68 | (structure) |
| 69 | (structure) |
| 70 | (structure) |

TABLE 79

| | $^1$H-NMR δ ppm |
|---|---|
| 66 | (solvent:CDCl$_3$) 1.16(3H, t, J=7.6Hz), 1.25(3H, t, J=7.6Hz), 1.26(3H, t, J=7.6Hz), 2.59(3H, s), 2.69(2H, q, J=7.6Hz), 2.8–3.1(2H, m), 3.71(2H, s), 4.11(2H, q, J=7.6Hz), 4.21(2H, q, J=7.6Hz), 4.8–4.9(1H, m), 5.37(2H, s), 6.47(1H, s), 6.91(1H, s), 7.52(1H, s), 8.03(1H, s), 9.08(1H, s), 9.49(1H, s), 12.68(1H, s), |
| 67 | (solvent:CDCl$_3$) 1.27(3H, t, J=7.6Hz), 2.59(3H, t), 2.70(2H, J=7.6Hz), 3.76(2H, s), 3.78(2H, d, J=0.7Hz), 5.28(2H, s), 6.43(1H, s), 7.51(1H, s), 6.90(1H, s), 7.72(1H, dd, J=7.9, 1.0Hz), 8.00(1H, dd, J=7.9, 7.6Hz), 8.25(1H, d, J=7.9Hz) |
| 68 | (solvent:CDCl$_3$) 1.28(3H, t, J=7.4Hz), 2.58(3H, s), 2.72(2H, q, J=7.5Hz), 3.77(2H, s), 4.05(2H, d, J=5.0Hz), 5.46(2H, s), 6.89(1H, s), 7.03(1H, d, J=6.6Hz), 7.5(1H, s), 7.72(1H, d, J=7.9Hz), 7.76(1H, dd, J=7.6, 7.9Hz), 7.99(1H, dd, J=7.6, 7.9Hz), 8.24(1H, d, J=7.6Hz), 8.30(1H, d, J=8.3Hz) |
| 69 | (solvent:CDCl$_3$) 1.27(3H, t, J=7.6Hz), 2.59(3H, s), 2.70(2H, q, J=7.3Hz), 3.72(2H, s), 3.8–4.0(2H, m), 4.58(3H, t, J=3.8Hz), 5.33 (2H, s), 6.48(1H, s), 6.94(1H, s), 7.52(1H, s), 7.76(1H, d, J=7.6Hz), 8.03(1H, dd, J=7.9, 7.9Hz), 8.25(1H, d, J=7.9Hz) |
| 70 | (solvent:CDCl$_3$) 1.27(3H, t, J=7.4Hz), 2.60(3H, s), 2.71(2H, q, J=7.5Hz), 3.37(2H, s), 3.73(3H, s), 3.87(1H, dd, J=11.5, 3.3Hz), 3.97(1H, dd, 11.5, 3.3Hz), 4.6–4.7(1H, m), 5.34(2H, s), 6.48(1H, s), 6.96(1H, s), 7.54(1H, s), 7.77(1H, d, J=7.6Hz), 8.04(1H, dd, J=7.9, 7.9Hz), 8.25(1H, d, J=7.6Hz) |

TABLE 80

| Ex. No. | Structural formula |
|---|---|
| 71 | (structure) |
| 72 | (structure) |

TABLE 80-continued

| Ex. No. | Structural formula |
|---|---|
| 73 | 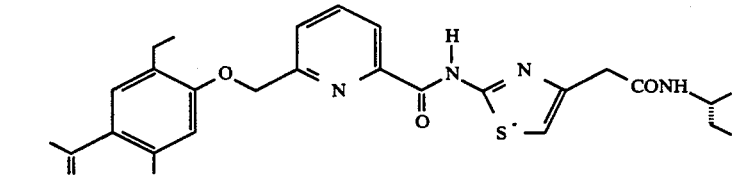 |
| 74 | |
| 75 | |

TABLE 81

| | $^1$H-NMR  δ ppm |
|---|---|
| 71 | (solvent:CDCl$_3$) 1.27(3H, t, J=7.6Hz), 1.5-2.2(4H, m), 2.59(3H, s), 2.70(2H, q, J=7.6Hz), 3.5-3.7(2H, m), 3.85(2H, J=2.3Hz), 4.6-4.7(1H, m), 5.32(2H, s), 6.49(1H, s), 6.92(1H, s), 7.51(1H, s), 7.73(1H, d, J=7.9Hz), 7.99(1H, dd, J=7.9, 7.9Hz), 8.23(1H, d, J=7.9Hz) |
| 72 | (solvent:CDCl$_3$) 1.26(3H, t, J=7.6Hz), 1.9-2.3(4H, m), 2.59(3H, s), 2.70(2H, q, J=7.5Hz), 3.6-3.8(2H, m), 3.82(2H, s), 4.12(2H, q, J=7.2Hz), 4.63(1H, dd, J=8.3, 3.6Hz), 5.18(2H, d, J=7.9Hz), 5.27(2H, s), 6.44(1H, s), 6.94(1H, s), 7.35(5H, m), 7.51(1H, s), 7.72(1H, d, J=6.9Hz), 8.00(1H, dd, J=7.9, 7.9Hz), 8.25(1H, d, J=7.9Hz) |
| 73 | (solvent:CDCl$_3$) 1.27(3H, t, J=7.6Hz), 2.60(3H, s), 2.71(2H, q, J=7.3Hz), 2.8-3.1(2H, m), 3.37(2H, d, J=5.0Hz), 3.71(2H, s), 4.80(1H, t, J=4.8Hz), 5.35(2H, s), |

TABLE 81-continued

| | $^1$H-NMR  δ ppm |
|---|---|
| | 6.49(1H, s), 6.93(1H, s), 7.54(1H, s), 7.76(1H, d, J=7.9Hz), 8.03(1H, dd, J=7.9, 7.9Hz), 8.23(1H, d, J=7.9Hz) |
| 74 | (solvent:CDCl$_3$) 1.19(3H, t, J=7.1Hz), 1.24(3H, t, J=7.4Hz), 1.27(3H, t, J=7.8Hz), 2.59(3H, s), 2.70(2H, q, J=7.2Hz), 2.85(1H, dd, J=17.2, 4.6Hz), 3.02(1H, dd, J=16.8, 4.6Hz), 3.72(2H, s), 4.10(2H, q, J=7.2Hz), 4.20(2H, q, J=7.1Hz), 4.85(1H, td, J=4.9, 7.6Hz), 5.31(2H, s), 6.44(1H, s), 6.89(1H, s), 7.51(1H, s), 7.74(1H, d, J=7.6Hz), 8.01(1H, dd, J=7.6, 7.9Hz), 8.26(1H, d, J=7.6Hz) |
| 75 | (solvent:CDCl$_3$) 1.27(3H, t, J=7.5Hz), 2.59(3H, s), 2.69(2H, q, J=7.3Hz), 3.26(2H, d, J=5.0Hz), 3.70(2H, s), 4.70(1H, t, J=5.0Hz), 5.33(2H, s), 6.48(1H, s), 6.95(1H, s), 7.05(1H, s), 7.50(1H, s), 7.76(1H, d, J=8.0Hz), 8.00(1H, dd, J=8.0, 8.0Hz), 8.22(1H, d, J=8.0Hz) |

TABLE 82

| Ex. No. | Structural formula |
|---|---|
| 76 | 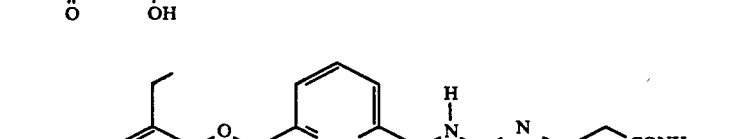 |
| 77 | 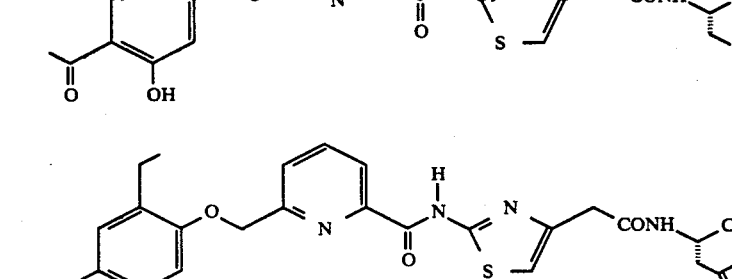 |

TABLE 82-continued

| Ex. No. | Structural formula |
|---|---|
| 78 | (structure) |
| 79 | (structure) |
| 80 | (structure) |

TABLE 83

| | $^1$H-NMR    δ ppm |
|---|---|
| 76 | (solvent:CDCl$_3$) 1.26(3H, t, J=7.5Hz), 2.59(3H, s), 2.69(2H, q, J=7.5Hz), 3.15(2H, t, J=4.2Hz), 3.71(3H, s), 3.73(2H, s), 4.84(1H, dt, J=7.3, 4.2Hz), 5.31(2H, s), 6.45(1H, s), 6.78(1H, s), 6.88(1H, s), 7.50(1H, s), 7.59(1H, s), 7.72(1H, d, J=7.6Hz), 8.01(1H, dd, J=7.9, 7.9Hz), 8.26(1H, d, J=7.6Hz), |
| 77 | (solvent:CDCl$_3$) 1.27(3H, t, J=7.5Hz), 1.9-2.5(4H, m), 2.0-2.5(4H, m), 2.60(3H, s), 2.71(2H, q, J=7.5Hz), 3.70(2H, s), 4.56(1H, t, J=4.0Hz), 5.35(2H, s), 6.49(1H, s), 6.94(1H, s), 7.36(1H, s), 7.77(1H, d, J=7.9Hz), 8.04(1H, dd, J=7.6, 7.9Hz), 8.24(1H, d, J=7.6Hz) |
| 78 | (solvent:CDCl$_3$) 1.21(3H, t, J=7.1Hz), 1.26(3H, t, J=7.4Hz), 1.29(3H, t, J=7.6Hz), 1.9-2.4(4H, m), 2.59(3H, s), 2.70(2H, q, J=7.4Hz), 3.70(2H, s), 4.09(2H, q, J=7.2Hz), 4.19(2H, q, J=6.9Hz), 4.63(1H, td, J=3.7, 7.6Hz), 5.33(2H, s), 6.47(1H, s), 6.88(1H, s), 7.51(1H, s), 7.75(1H, d, J=6.9Hz), 8.02(1H, dd, J=6.9, 7.6Hz), 8.26(1H, d, J=6.9Hz) |
| 79 | (solvent:CDCl$_3$) 1.21(3H, t, J=7.6Hz), 2.51(3H, s), 2.62(2H, q, J=7.6Hz), 3.20(2H, br), 4.71(1H, t, J=5.3Hz), 5.23(2H, s), 6.43(1H, s), 7.41(1H, s), 7.05(1H, s), 7.05(1H, d, J=7.3Hz), 7.31(1H, s), 7.61(1H, dd, J=7.9Hz), 7.67(1H, dd, J=7.9, 7.9Hz), 7.90(1H, dd, J=7.6, 7.6Hz), 8.12(1H, d, J=7.3Hz), 8.19(1H, d, J=8.3Hz), |
| 80 | (solvent:CDCl$_3$) 1.27(3H, t, J=7.4Hz), 2.59(3H, s), 2.70(2H, q, J=7.4Hz), 3.17(2H, J=5.0Hz), 3.67(3H, s), 3.77(2H, s), 4.82(1H, dt, J=6.9, 5.0Hz), 5.22(2H, s), 6.35(1H, s), 6.71(1H, s), 7.07(1H, d, J=7.3Hz), 7.45(1H, s), 7.51(1H, s), 7.67(1H, d, J=7.3Hz), 7.76(1H, dd, J=7.9, 7.9Hz), 7.98(1H, dd, J=7.9, 7.9Hz), 8.26(1H, d, J=6.9Hz), 8.32(1H, d, J=7.9Hz) |

TABLE 84

| Ex. No. | Structural formula |
|---|---|
| 81 | (structure) |

TABLE 84-continued

| Ex. No. | Structural formula |
|---|---|
| 82 | (structure) |
| 83 | (structure) |
| 84 | (structure) |
| 85 | (structure) |

TABLE 85

| | $^1$H-NMR δ ppm |
|---|---|
| 81 | (solvent:CDCl$_3$) 1.28(3H, t, J=7.4Hz), 1.9-2.5(4H, m), 2.60(3H, s), 2.72(2H, q, J=7.4Hz), 3.84(2H, s), 4.5-4.6(1H, m), 5.42(2H, s), 6.56(2H, s), 7.26(1H, d, J=7.9Hz), 7.54(1H, s), 7.76(1H, d, J=8.3Hz, 7.94(1H, dd, J=7.9, 7.9Hz), 8.03(1H, dd, J=7.9, 7.6Hz), 8.24(1H, d, J=7.9Hz), 8.39(1H, d, J=8.6Hz) |
| 82 | (solvent:CDCl$_3$) 1.16(3H, t, J=7.3Hz), 1.20(3H, t, J=7.1Hz), 1.27(3H, t, J=7.4Hz), 2.59(3H, s), 2.71(2H, q, J=7.4Hz), 2.0-2.4(4H, m), 3.74(2H, s), 4.03(2H, q, J=7.1Hz), 4.1-4.3(2H, m), 4.65(1H, td, J=7.6, 5.3Hz), 5.39(2H, s), 6.49(1H, s), 7.06(1H, d, J=6.6Hz), 7.51(1H, s), 7.71(1H, d, J=7.3Hz), 7.73(1H, dd, J=7.9, 7.9Hz), 7.99(1H, dd, J=7.6, 7.9Hz), 8.27(1H, d, J=7.9Hz), 8.34(1H, d, J=7.9Hz) |
| 83 | (solvent:CDCl$_3$) 1.27(3H, t, J=7.4Hz), 2.0-2.1(4H, m), 2.58(3H, s), 2.71(2H, q, J=7.4Hz), 3.67(2H, m), 3.94(2H, d, J=4.3Hz), 4.75(1H, d, J=5.9Hz), 5.39(2H, s), 6.56(2H, s), 7.10(1H, d, J=7.6Hz), 7.50(1H, s), 7.71(1H, d, J=7.9Hz), 7.78(1H, dd, J=7.9, 7.9Hz), 7.98(1H, dd, J=7.9, 7.6Hz), 8.24(1H, d, J=7.6Hz), 8.37(1H, d, J=8.3Hz) |
| 84 | (solvent:CDCl$_3$) 1.26(3H, t, J=7.6Hz), 1.9-2.3(4H, m), 2.58(3H, s), 2.70(2H, q, J=7.5Hz), 3.6-3.8(2H, m), 3.88(2H, s), 4.12(2H, q, J=7.2Hz), 4.63(1H, dd, J=8.3, 3.6Hz), 5.17(2H, d, J=7.9Hz), 5.31(2H, s), 6.47(1H, s), 7.15(1H, d, J=6.6Hz), 7.34(5H, m), 7.50(1H, s), 7.67(1H, d, J=7.6Hz), 7.68(1H, dd, J=7.9, 7.6Hz), 7.97(1H, dd, J=7.9, 7.6Hz), 8.26(1H, d, J=6.9Hz), 8.30(1H, d, J=8.3Hz) |
| 85 | (solvent:CDCl$_3$) 1.28(3H, t, J=7.4Hz), 2.60(3H, s), 2.72(2H, q, J=7.4Hz), 3.79(2H, s), 3.8-4.1(1H, m), 4.59(1H, t, J=3.5Hz), 5.39(2H, s), 6.52(1H, s), 7.54(1H, s), 7.74(1H, d, J=7.9Hz), 7.80(1H, dd, J=7.6, 8.3Hz), 8.02(1H, dd, J=7.9, 7.6Hz), 8.24(1H, d, J=7.9Hz), 8.31(1H, d, J=8.2Hz), 7.15(1H, d, J=7.3Hz) |

TABLE 86

| Ex. No. | Structural formula |
|---|---|
| 86 | (structure) |

TABLE 86-continued

| Ex. No. | Structural formula |
|---|---|
| 87 | |
| 88 | |
| 89 | |
| 90 | |

TABLE 87

| | $^1$H-NMR δ ppm |
|---|---|
| 86 | (solvent:CDCl$_3$) 1.27(3H, t, J=7.4Hz), 2.58(3H, s), 2.69(2H, q, J=7.4Hz), 3.74(3H, s), 3.79(2H, s), 4.00(2H, d, J=3.3Hz), 4.71(1H, dt, J=7.3, 3.6Hz), 5.38(2H, s), 6.50(1H, s), 7.05(1H, d, J=6.6Hz), 7.49(1H, s), 7.70(1H, d, J=7.9Hz), 7.75(1H, dd, J=7.6, 8.2Hz), 7.98(1H, dd, J=7.9, 6.7Hz), 8.25(1H, d, J=6.6Hz), 8.27(1H, d, J=8.2Hz) |
| 87 | (solvent:DMSO-d$_6$) 1.19(3H, t, J=7.6Hz), 2.60(3H, s), 2.64(2H, q, J=7.6Hz), 3.53(2H, s), 5.49(2H, s), 6.55(1H, s), 6.89(1H, s), 7.64(1H, s), 8.04(1H, d, J=5.0Hz), 9.05(1H, s)(DMSO-d$_6$) |
| 88 | (solvent:CDCl$_3$) 1.27(3H, t, J=7.6Hz), 1.29(3H, t, J=7.3Hz), 2.58(3H, s), 2.71(2H, q, J=7.6Hz), 3.76(2H, s), 4.21(2H, q, J=7.3Hz), 5.43(2H, s), 6.41(1H, s), 6.94(1H, s), 7.51(1H, s), 8.13(1H, d, J=5.0Hz), 9.09(1H, d, J=5.0Hz), 10.93(br), 12.64(1H, s) |
| 89 | (sovlent:DMSO-d$_6$) 1.22(3H, t, J=7.6Hz), 2.59(3H, s), 2.67(2H, q, J=7.6Hz), 3.73(2H, s), 5.56(2H, s), 6.71(1H, s), 7.20(1H, d, J=7.6Hz), 7.71(1H, s), 7.89(1H, dd, J=7.6Hz, 7.9Hz), 8.16(1H, d, J=7.9Hz), 9.08(1H, s), 9.32(1H, s), 10.22(1H, s), 12.58(1H, s) |
| 90 | (solvent:CDCl$_3$) 1.27(3H, i, J=7.6Hz), 1.28(3H, t, J=7.3Hz), 2.60(3H, s), 2.70(2H, q, J=7.6Hz), 3.80(2H, s), 4.21(2H, q, J=7.3Hz), 5.38(2H, s), 6.50(1H, s), 7.12(1H, dd, J=0.7Hz, 7.6Hz), 7.52(1H, s), 7.78(1H, t, J=7.9Hz), 8.34(1H, d, J=8.3Hz), 9.04(1H, s), 10.06(1H, s), 12.68(1H, s) |

TABLE 88

| Ex. No. | Structural formula |
|---|---|
| 91 | |

TABLE 88-continued

| Ex. No. | Structural formula |
|---|---|
| 92 | 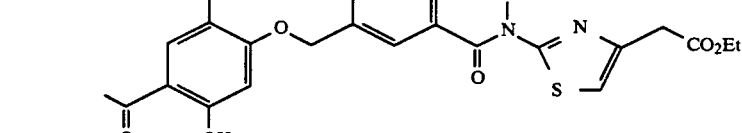 |
| 93 | 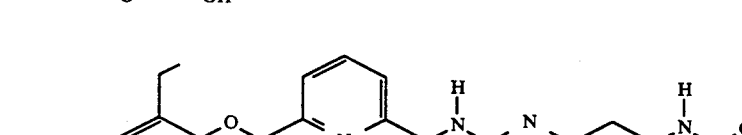 |
| 94 | 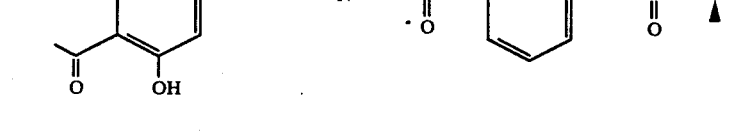 |
| 95 | 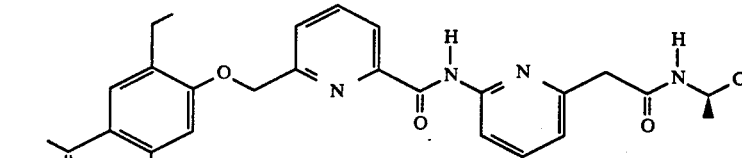 |

TABLE 89

| | $^1$H-NMR     δ ppm |
|---|---|
| 91 | (solvent:CDCl$_3$) 1.22(3H, t, J=7.6Hz), 2.58(3H, s), 2.65(2H, q, J=7.6Hz), 3.72(2H, s), 5.20(2H, s), 6.47(1H, s), 6.87(1H, s), 7.50(1H, s), 7.58(1H, dd, J=7.6, 7.6Hz), 7.69(1H, d, J=7.6Hz), 7.98(1H, d, J=7.6Hz), 8.09(1H, s) |
| 92 | (solvent:CDCl$_3$) 1.22(3H, t, J=7.4Hz), 1.28(3H, t, J=7.1Hz), 2.58(3H, s), 2.64(2H, q, J=7.4Hz), 3.69(2H, s), 4.19(2H, q, J=7.1Hz), 5.18(2H, s), 6.45(1H, s), 6.86(1H, s), 7.47(1H, s), 7.57(1H, dd, J=7.6, 7.6Hz), 7.68(1H, d, J=7.6Hz), 7.88(1H, d, J=7.6Hz), 8.02(1H, s) |
| 93 | (solvent:CDCl$_3$) 1.28(3H, t, J=7.6Hz), 1.47(3H, d, J=7.3Hz), 2.60(3H, s), 2.72(2H, q, J=7.6Hz), 3.89(2H, s), 4.50(1H, dt, J=7.2, 7.3Hz), 5.45(2H, s), 6.57(1H, s), 7.34(1H, d, J=7.6Hz), 7.53(1H, s), 7.78(1H, d, J=7.9Hz), 8.02(1H, dd, J=7.6, 7.9Hz), 8.03(1H, dd, J=7.6, 7.6Hz), 8.23(1H, d, J=7.6Hz), 8.45(1H, d, J=8.2Hz), |
| 94 | (solvent:CDCl$_3$) 1.27(3H, t, J=7.6Hz), 1.43(3H, d, J=7.3Hz), 2.59(3H, s), 2.71(2H, q, J=7.6Hz), 3.72(3H, s), 3.74(2H, s), 4.61(1H, qd, J=7.1Hz), 5.39(2H, s), 6.49(1H, s), 7.06(1H, d, J=7.3Hz), 7.51(1H, s), 7.72(1H, d, J=7.3Hz), 7.76(1H, dd, J=7.9, 7.6Hz), 8.00(1H, dd, J=7.9, 7.6Hz), 8.27(1H, d, J=8.6Hz), 8.34(1H, d, J=8.3Hz) |
| 95 | (solvent:CDCl$_3$/MeOD(4/1)) 1.28(3H, t, J=7.6Hz), 2.60(3H, s), 2.72(2H, q, J=7.6Hz), 3.77(2H, s), 3.97(2H, s), 3.99(2H, s), 5.38(2H, s), 6.53(1H, s), 7.14(1H, d, J=7.6Hz), 7.37(1H, s), 7.75(1H, d, J=7.9Hz), 7.79(1H, dd, J=7.6, 8.2Hz), 8.02(1H, dd, J=7.6, 7.9Hz), 8.25(1H, d, J=7.9Hz), 8.30(1H, d, J=8.2Hz) |

TABLE 90

| Ex. No. | Structural formula |
|---|---|
| 96 |

TABLE 90-continued

| Ex. No. | Structural formula |
|---|---|
| 97 | [structure: 4-acetyl-2-ethyl-5-hydroxyphenoxymethyl-pyridine linked via carboxamide to pyridine N-oxide bearing CH2CO2H] |
| 98 | [structure: same as 97 but with CO2Et instead of CO2H] |
| 99 | [structure: 4-acetyl-2-ethyl-5-hydroxyphenoxymethyl-pyridine-carboxamido-pyridine-CH2-C(O)NH-CH(CO2H)-CH2-CO2H (aspartate)] |
| 100 | [structure: same as 99 but with CO2Et diester] |

TABLE 91

| | $^1$H-NMR δ ppm |
|---|---|
| 96 | (solvent:CDCl$_3$) 1.21(3H, t, J=7.1Hz), 1.27(3H, t, J=7.4Hz), 2.58(3H, s), 2.71(2H, q, J=7.4Hz), 3.78(2H, s), 4.0-4.1(4H, m), 4.12(2H, q, J=7.1Hz), 5.40(2H, s), 6.52(1H, s), 7.07(1H, d, J=7.3Hz), 7.50(1H, s), 7.72(1H, d, J=7.9Hz), 7.76(1H, t, J=8.3, 7.6Hz), 7.99(1H, dd, J=7.9, 7.9Hz), 8.27(1H, d, J=8.6Hz), 8.30(1H, d, J=8.9Hz) |
| 97 | (solvent:DMSO-d$_6$) 1.30(3H, t, J=7.6Hz), 2.59(3H, s), 2.72(2H, q, J=7.6Hz), 3.49(1H, s), 4.13(2H, s), 5.40(2H, s), 6.48(1H, s), 7.17(1H, dd, J=1.8Hz, 7.9Hz), 7.51(1H, s), 7.61(1H, dd, J=7.9Hz, 8.3Hz), 7.76(1H, d, J=7.9Hz), 8.02(1H, dd, J=7.9Hz, 7.9Hz), 8.26(1H, d, J=8.6Hz), 8.75(1H, dd, J=1.8Hz, 8.3Hz), 12.18(1H, br), 12.63(1H, s), |
| 98 | (solvent:CDCl$_3$) 1.27(3H, t, J=7.6Hz), 1.31(1H, t, J=7.1Hz), 2.58(3H, s), 2.70(2H, q, J=7.6Hz), 3.99(2H, s), 4.26(2H, q, J=7.1Hz), 5.35(2H, s), 6.46(1H, s), 7.11(1H, dd, J=1.7Hz, 7.9Hz), 7.36(1H, dd, J=7.9Hz, 7.9Hz), 7.49(1H, s), 7.72(1H, dd, J=1.0Hz, 7.9Hz), 7.98(1H, dd, J=7.9Hz, 7.9Hz), 8.23(1H, dd, J=1.0Hz, 7.9Hz), 8.63(1H, dd, J=2.0Hz), 8.6Hz), 12.29(1H, br), 12.62(1H, s) |
| 99 | (solvent:CDCl$_3$) 1.29(3H, t, J=7.4Hz), 2.57(3H, s), 2.72(2H, t, J=7.4Hz), 2.96(1H, dd, J=17.0, 4.5Hz), 3.09(1H, dd, J=17.0, 4.5Hz), 3.77(2H, s), 4.85(1H, br), 5.49(2H, d, J=3.3Hz), 6.72(1H, s), 7.02(1H, d, J=8.3Hz), 7.49(1H, s), 7.65(1H, d, J=7.9Hz), 7.75(1H, dd, J=7.6, 8.3Hz), 7.94(1H, dd, J=7.6, 8.3Hz), 7.94(1H, dd, J=7.9, 7.6Hz), 8.19(1H, d, J=7.6Hz), 8.32(1H, d, J=8.3Hz) |
| 100 | (solvent:CDCl$_3$) 1.10(3H, t, J=7.0Hz), 1.17(3H, t, J=7.1Hz), 1.28(3H, t, J=7.4Hz), 2.59(3H, s), 2.71(2H, q, J=7.4Hz), 2.85(1H, dd, J=17.0, 4.6Hz), 3.02(1H, dd, J=17.0, 4.6Hz), 3.75(2H, s), 4.00(2H, q, J=7.1Hz), 4.16(2H, q, J=7.0Hz), 4.85(1H, dt, J=7.6, 4.6Hz), 5.39(2H, s), 6.49(1H, s), 7.05(1H, d, J=7.3Hs), 7.51(1H, s), 7.72(1H, d, J=7.6Hz), 7.73(1H, dd, J=7.3, 7.6Hz), 7.99(1H, dd, J=7.6, 7.9Hz), 8.27(1H, d, J=7.3Hz), 8.34(1H, d, J=8.3Hz) |

TABLE 92

| Ex. No. | Structural formula |
|---|---|
| 101 | [structure: 4-acetyl-2-ethyl-5-hydroxyphenoxymethyl-phenyl-C(O)NH-C(=N-)-S-CH=C(NH-)-CH(CO2H)-CH2-CO2H thiazole-containing aspartate derivative] |

TABLE 92-continued

| Ex. No. | Structural formula |
|---|---|
| 102 | |
| 103 | |
| 104 | |
| 105 | |

TABLE 93

| | $^1$H-NMR   δ ppm |
|---|---|
| 101 | (solvent:DMSO-d$_6$) 1.17(3H, t, J=7.6Hz), 2.56(3H, s), 2.59(1H, m), 2.69(1H, m), 3.59(2H, s), 3.6-4.3(2H, br), 4.56(1H, m), 5.29(2H, s), 6.60(1H, s), 6.96(1H, s), 6.96(1H, s), 7.56(1H, t, J=7.9Hz), 7.64(1H, s), 7.68(1H, d, J=7.9Hz), 8.07(1H, d, J=7.9Hz), 8.19(1H, s), 8.23(1H, d, J=7.6Hz), 12.6(1H, s) |
| 102 | (solvent:CDCl$_3$/DMSO-d$_6$(10/1)) 1.15-1.31(9H, m), 2.57(3H, s), 2.64(2H, q, J=7.3Hz), 2.84(1H, dd, J=17.2, 4.6Hz), 3.03(1H, dd, J=17.2, 4.3Hz), 3.67(2H, s), 4.15-4.27(4H, m), 4.85(1H, ddd, J=7.9, 4.6, 4.3Hz), 5.19(1H, s), 6.46(1H, s), 6.78(1H, s), 7.48(1H, s), 7.57(1H, t, J=7.9Hz), 7.69(1H, d, J=7.9Hz), 7.94(1H, brd, J=8.3Hz), 7.97(1H, d, J=7.9Hz), 8.10(1H, s), 12.68(1H, s) |
| 103 | (solvent:DMSOO-d$_6$) 1.21(3H, t, J=7.3Hz), 2.58(H, s), 2.6-2.7(4H, m), 4.08(1H, s), 4.60(1H, m), 5.46(2H, s), 5.6-6.4(2H, br), 6.62(1H, s), 7.68(1H, s), 7.80(2H, d), 8.15(2H, m), 8.78(1H, d, J=7.9Hz), 12.55(1H, s) |
| 104 | (solvent:CDCl$_3$) 1.23-1.65(9H, m), 2.59(3H, s), 2.70(2H, q, J=7.3Hz), 2.85(1H, dd, J=17.2, 4.6Hz), 3.05(1H, dd, J=17.2, 4.6Hz), 4.10(2H, s), 4.15(2H, q, J=7.3Hz), 4.22(2H, q, J=7.3Hz), 4.87(1H, dt, J=7.9, 4.6Hz), 5.32(1H, s), 6.45(1H, s), 7.24(1H, brd), 7.52(1H, s), 7.75(1H, d, J=7.3Hz), 8.01(1H, t, J=7.9Hz), 8.26(1H, d, J=7.9Hz), 12.67(1H, s) |
| 105 | (solvent:DMSO-d$_6$) 0.96(6H, m), 1.30(3H, t, J=7.6Hz), 2.17(1H, m), 2.58(3H, s), 2.73(2H, q, J=7.6Hz), 3.75(2H, m), 4.67(1H, m), 5.42(2H, s), 6.83(1H, s), 7.02(1H, d, J=7.9Hz), 7.51(1H, s), 7.65(1H, d, J=7.9Hz), 7.75(1H, t, J=7.9Hz), 7.95(1H, t, J=7.9Hz), 8.22(1H, d, J=7.9Hz), 8.32(1H, d, J=7.9Hz), 8.91(1H, brd), 10.87(1H, s) |

TABLE 94

| Ex. No. | Structural formula |
|---|---|
| 106 | |

TABLE 94-continued

| Ex. No. | Structural formula |
|---|---|
| 107 | (structure with pyridine-methyleneoxy linker to acetyl-hydroxy-ethylphenyl group, amide to aminopyridine, CH₂C(O)NH-CH(CO₂H)(CH₂SMe)) |
| 108 | (same as 107 but CO₂Et instead of CO₂H) |
| 109 | (same as 107 but middle pyridine is N-oxide, and side chain is Asp: CH(CO₂H)CH₂CO₂H) |
| 110 | (same as 109 but diethyl ester: CH(CO₂Et)CH₂CO₂Et) |

TABLE 95

| | ¹H-NMR δ ppm |
|---|---|
| 106 | (solvent:CDCl₃) 0.91(3H, m), 1.27(3H, t, J=7.3Hz), 2.18(1H, m), 2.59(3H, s), 2.71(2H, q, J=7.3Hz), 3.71(3H, s), 3.76(2H, s), 4.60(1H, s), 5.34(2H, s), 6.46(1H, s), 7.05(1H, d, J=7.6Hz), 7.51(1H, s), 7.73(1H, t, J=7.6Hz), 7.78(1H, d, J=7.9Hz), 7.97(1H, br), 8.00(1H, t, J=7.9Hz), 8.27(1H, d, J=7.9Hz), 8.35(1H, d, J=7.9Hz), 10.54(1H, s), 12.62(1H, s) |
| 107 | (solvent:DMSO-d₆) 1.31(3H, t, J=7.6Hz), 2.01(3H, s), 2.15(1H, m), 2.35(1H, m), 2.55(2H, m), 2.58(3H, s), 2.74(2H, q, J=7.6Hz), 3.80(1H, d, J=15.8Hz), 3.68(1H, d, J=15.8Hz), 4.73(1H, m), 5.48(2H, s), 6.83(1H, s), 7.02(1H, d, J=7.6Hz), 7.51(1H, s), 7.63(1H, d, J=7.6Hz), 7.75(1H, t, J=7.6Hz), 7.94(1H, t, J=7.6Hz), 8.22(1H, d, J=7.6Hz), 8.33(1H, d, J=7.6Hz), 9.08(1H, brd), 10.87(1H, s) |
| 108 | (solvent:CDCl₃) 1.1–1.3(6H, m), 2.00(3H, s), 2.05–2.2(2H, m), 2.47(2H, m), 2.59(3H, s), 2.70(2H, q, J=7.3Hz), 3.74(2H, s), 4.16(2H, m), 4.71(1H, m), 5.40(2H, s), 6.50(1H, s), 7.06(1H, d, J=7.6Hz), 7.51(1H, s), 7.75(1H, t, J=7.6Hz), 7.77(1H, d, J=7.9Hz), 7.96(1H, br), 8.00(1H, t, J=7.6Hz), 8.27(1H, d, J=7.3Hz), 8.34(1H, d, J=8.3Hz), 10.53(1H, s), 12.63(1H, s) |
| 109 | (solvent:DMSO-d₆) 1.21(3H, t, J=7.3Hz), 2.51(3H, s), 2.63(4H, m), 3.89(2H, s), 4.59(1H, m), 5.42(2H, s), 6.63(1H, s), 7.29(1H, d, J=8.3Hz), 7.44(1H, t, J=8.3Hz), 7.65(1H, s), 7.83(1H, d, J=7.3Hz), 8.18(1H, t, J=7.3Hz), 8.23(1H, brd), 8.47(1H, d, J=8.3Hz), 8.59(1H, d, J=7.3Hz), 12.16(1H, s), 12.51(1H, s), 12.6(2H, br) |
| 110 | (solvent:CDCl₃) 1.15(3H, t, J=7.3Hz), 1.17(3H, t, J=7.3Hz), 1.27(3H, t, J=7.3Hz), 2.59(3H, s), 2.71(1H, q, J=7.3Hz), 2.83(1H, dd, J=16.8Hz, 5.3Hz), 2.94(1H, dd, J=16.8Hz, 5.3Hz), 3.96(1H, d, J=13.5Hz), 4.07(1H, d, J=13.5Hz), 4.11(2H, q, J=7.3Hz), 4.12(2H, q, J=7.3Hz), 4.81(1H, dt, J=8.2Hz, 5.3Hz), 5.39(2H, s), 6.48(1H, s), 7.18(1H, dd, J=7.9Hz, 1.7Hz), 7.41(1H, t, J=7.9Hz), 7.50(1H, s), 7.76(1H, d, J=7.9Hz), 8.01(1H, t, J=7.9Hz), 8.25(1H, d, J=7.9Hz), 8.63(1H, dd, J=7.4Hz, 1.7Hz), 8.69(1H, d, J=8.2Hz), 12.32(1H, s), 12.61(1H, s) |

TABLE 96

| Ex. No. | Structural formula |
|---|---|
| 111 | (structure) |
| 112 | (structure) |
| 113 | (structure) |
| 114 | (structure) |
| 115 | (structure) |

TABLE 97

$^1$H-NMR δ ppm 111 (solvent:DMSO-d$_6$) 1.12(3H, d, J=6.6Hz), 1.22(3H, t, J=7.6Hz), 2.30(1H, dd, J=15.2Hz, 7.3Hz), 2.46(1H, dd, J=15.2Hz, 7.3Hz), 2.58(3H, s), 2.67(2H, q, J=7.6Hz), 3.56(2H, s), 4.10(1H, m), 5.47(2H, s), 6.64(2H, s), 7.13(1H, d, J=7.6Hz), 7.69(1H, s), 7.80-7.86(2H, m), 8.10-8.30(4H, m), 10.35(1H, s), 12.17(1H, s), 12.56(1H, s)

112 (solvent:CDCl$_3$) 1.26(6H, m), 2.53(2H, d, J=5.3Hz), 2.59 (3H, s), 2.71(3H, s), 2.71(2H, m), 3.55(3H, s), 3.68(2H, s), 4.36(1H, m), 5.36(2H, s), 6.47(1H, s), 7.06(1H, d, J=7.6Hz), 7.42(1H, brd, J=7.9Hz), 7.51(1H, s), 7.70(1H, d, J=7.6Hz), 7.75(1H, t, J=7.6Hz), 7.99(1H, t, J=7.6Hz), 8.27(1H, d, J=7.6Hz), 8.31(1H, d, J=7.6Hz), 10.48(1H, s), 12.65(1H, s)

113 (solvent:DMSO-d$_6$) 1.23(3H, t, J=7.3Hz), 2.14(1H, m), 2.6 (1H, m), 2.58(3H, s), 2.67(2H, q, J=7.3Hz), 3.45-3.70(2H, m), 3.83(1H, m), 4.22(1H, m), 5.02(0.4H, m), 4.57(0.6H, m), 5.48(2H, s), 6.65(1H, s), 7.14(1H, m), 7.69(1H, s), 7.65-7.90 (2H, m), 8.15-8.30(3H, m), 10.32(0.6H, s), 10.34(0.4H, s), 12.55(1H, s), 12.90(1H, br)

114 (solvent:CDCl$_3$) 1.27(3H, t, J=7.6Hz), 2.20-2.40(1H, m), 2.5-2.7(1H, m), 2.59(3H, s), 2.71(2H, q, J=7.6Hz), 3.64 (0.4H, s), 3.68(0.6H, s), 3.77(0.6H, s), 3.80(0.4H, s), 4.05-4.40 (2H, m), 4.79(0.6H, m), 4.95(0.4H, m), 5.34(2H, s), 6.48(1H, s), 7.13(0.4H, d, J=7.6Hz), 7.19(0.6H, d, J=7.6Hz), 7.51 (1H, s), 7.70(1H, d, J=7.6Hz), 7.75(1H, m), 7.98(1H, t, J=7.6Hz), 8.27(1H, d, J=7.6Hz), 8.32(1H, d, J=7.6Hz), 10.34 (1H, s), 12.67(1H, s)

115 (solvent:CDCl$_3$) 1.28(3H, t, J=7.6Hz), 2.58(3H, s), 2.72(2H, q, J=7.6Hz), 2.91(2H, t, J=5.7Hz), 3.87(2H, s), 3.92(2H, t, J=5.7Hz), 5.46(2H, s), 6.60(1H, s), 6.88(1H, d, J=7.3Hz), 7.12(1H, d, J=6.6Hz), 7.50(1H, s), 7.62(1H, dd, J=7.6, 8.3Hz), 7.73(1H, d, J=7.9Hz), 7.78(1H, dd, J=7.6, 8.3Hz), 7.98(1H, dd, J=7.6, 7.9Hz), 8.06(1H, d, J=8.3Hz), 8.27(1H, d, J=7.9Hz), 8.40(1H, d, J=7.6Hz)

TABLE 98

| Ex. No. | Structural formula |
|---|---|
| 116 | |
| 117 | |
| 118 | |
| 119 | |
| 120 | |

TABLE 99

$^1$H-NMR δ ppm 116 (solvent:CDCl$_3$/MeODC(1/4))1.28(3H, t, J=7.6Hz), 2.60 (3H, s), 2.72(2H, q, J=7.6Hz), 2.88(2H, t, J=6.3Hz), 3.86 (2H, t, J=6.3Hz), 3.97(2H, s), 5.39(2H, s), 6.52(1H, s), 6.68 (1H, s), 7.19(1H, d, J=7.6Hz), 7.55(1H, s), 7.76(1H, d, J= 7.9Hz), 7.83(1H, dd, J=8.2, 7.6Hz), 8.05(1H, dd, J=7.6, J= 7.9Hz), 8.25(1H, d, J=7.6Hz), 8.33(1H, d, J=8.2Hz)

117 (solvent:CDCl$_3$) 1.0–1.3(5H, m), 2.59(3H, s), 2.71(2H, q, J=7.5Hz), 3.4–3.9(6H, m), 3.4–3.9(6H, m), 3.93(2H, s), 5.35(2H, s), 6.49(1H, s), 7.0–7.2(1H, m), 7.51(1H, s), 7.6–8.4(5H, m)

118 (solvent:CDCl$_3$) 1.27(3H, t, J=7.4Hz), 2.58(3H, s), 2.70(2H, q, J=7.4Hz), 3.6–4.0(8H, m), 4.00(2H, s), 5.35(2H, s), 6.51(1H, s), 7.11(1H, d, J=7.6Hz), 7.50(1H, s), 7.70(1H, d, J=7.6Hz), 7.76(1H, dd, J=7.6, 7.6Hz),

TABLE 99-continued $^1$H-NMR δ ppm 7.97(1H, dd, J=7.6, 7.9Hz), 8.24(1H, d, J=7.9Hz), 8.32(1H, d, J=7.6Hz)

119 (solvent:CDCl$_3$) 1.28(3H, t, J=7.4Hz), 2.60(3H, s), 2.71(2H, q, J=7.4Hz), 3.42(2H, t, J=6.6Hz), 3.68(2H, t, J=6.6Hz), 3.71(2H, s), 5.37(2H, s), 6.50(1H, s), 7.13(1H, d, J=7.6Hz), 7.53(1H, s), 7.74(1H, d, J=7.6Hz), 7.76(1H, dd, J=8.2, 7.6Hz), 8.02(1H, dd, J=7.6, 7.6Hz), 8.25(1H, d, J=7.6Hz), 8.27(1H, d, J=8.2Hz)

120 (solvent:CDCl$_3$) 1.27(3H, t, J=7.4Hz), 2.59(3H, s), 2.71(2H, q, J=7.4Hz), 2.93(2H, t, J=6.8Hz), 4.48(2H, t, J=6.8Hz), 5.32(2H, s), 6.31(1H, d, J=8.1Hz), 6.45(1H, d, J=8.1Hz), 7.03(1H, d, J=7.6Hz), 7.29(1H, d, J=8.1, 8.1Hz), 7.69(1H, d, J=7.6Hz) 7.71(1H, dd, J=7.6, 7.6Hz), 7.97(1H, dd, J=7.6, 7.6Hz), 8.26(1H, d, J=7.6Hz), 8.33(1H, d, J=7.6Hz)

TABLE 100

| Ex. No. | Structural formula |
|---|---|
| 121 | 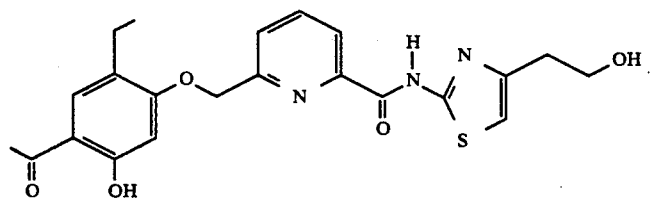 |
| 122 | 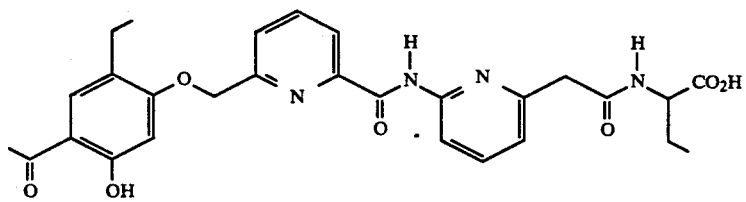 |
| 123 | 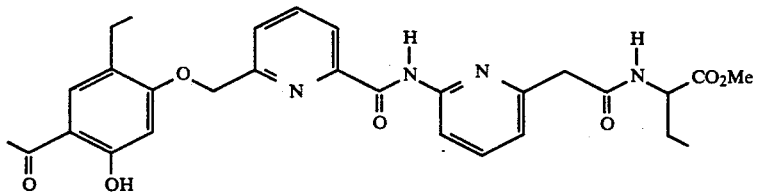 |
| 124 | 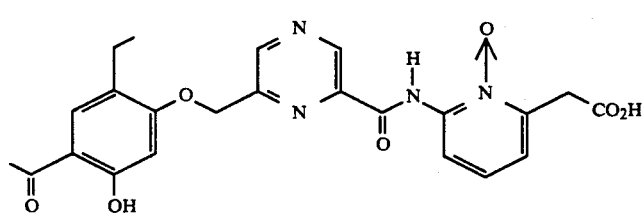 |
| 125 | 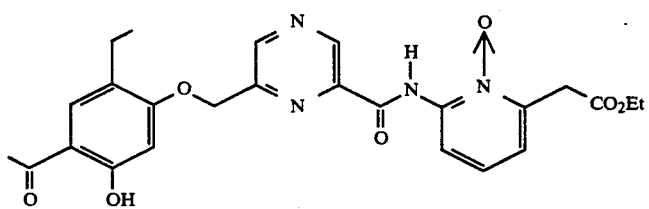 |

TABLE 101

$^1$H-NMR δ ppm 121 (solvent:CDCl$_3$) 1.28(3H, t, J=7.4Hz), 2.59(3H, s), 2.71(2H, q, J=7.4Hz), 2.96(2H, t, J=5.5Hz), 3.96(2H, t, J=5.5Hz), 5.33(2H, s), 6.45(1H, s), 6.73(1H, s), 7.51(1H, s), 7.72(1H, d, J=6.9Hz), 8.00(1H, dd, J=7.9, 7.6Hz), 8.25(1H, dd, J=7.6Hz)

122 (solvent:DMSO-d$_6$) 0.41(3H, t, J=7.6Hz), 1.30(3H, t, J=7.6Hz), 1.7–1.9(2H, m), 2.57(3H, s), 3.74(2H, ABq, J=15.4Hz, 5.5Hz), 4.66(1H, m), 5.46(2H, s), 6.83(1H, s), 7.02 (1H, d, J=7.6Hz), 7.51(1H, s), 7.63(1H, d, J=7.6Hz), 7.75 (1H, t, J=7.6Hz), 7.94(1H, t, J=7.6Hz), 8.22(1H, d, J=7.6Hz), 8.32(1H, d, J=7.6Hz), 8.94(1H, m), 10.86(1H, s)

123 (solvent:CDCl$_3$) 0.88(3H, t, J=7.3Hz), 1.27(3H, t, J=7.6Hz), 1.7–1.9(2H, m), 2.59(3H, s), 2.71(2H, q, J=7.6Hz), 3.71(3H, s), 3.74(2H, s), 4.63(1H, m), 5.37(2H, s), 6.47(1H, TABLE 101-continued $^1$H-NMR δ ppm s), 7.06(1H, d, J=7.6Hz), 7.71(1H, d, J=7.6Hz), 7.75(1H, t, J=7.6Hz), 7.86(1H, m), 8.00(1H, t, J=7.6Hz), 8.27(1H, d, J=7.6Hz), 8.35(1H, m, J=7.6Hz), 10.53(1H, s), 12.63(1H, s)

124 (solvent:DMSO-d$_6$) 1.19(3H, t, J=7.6Hz), 2.59(3H, s), 2.65(2H, q, J=7.6Hz), 3.89(2H, s), 5.53(2H, s), 6.73(1H, s), 7.37(1H, d, J=7.9Hz), 7.51(1H, t, J=7.9Hz), 7.69(1H, s), 8.46(1H, d, J=7.9Hz), 9.13(1H, s), 9.37(1H, s), 11.96(1H, s), 12.50(1H, br), 12.54(1H, s)

125 (solvent:CDCl$_3$) 1.26(3H, t, J=7.6Hz), 1.31(3H, t, J=7.3Hz), 2.60(3H, s), 2.69(2H, q, J=7.6Hz), 3.98(3H, s), 4.25(2H, q, J=7.3Hz), 5.39(2H, s), 6.47(1H, s), 7.15(1H, dd, J=8.3Hz, 2.0Hz), 7.39(1H, t, J=8.3Hz), 7.52(1H, s), 8.61(1H, dd, J=8.3Hz, 2.0Hz), 9.07(1H, s), 9.46(1H, s), 12.12(1H, s), 12.65(1H, s)

TABLE 102

| Ex. No. | Structural formula |
|---|---|
| 126 | 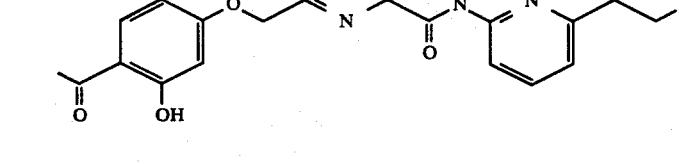 |
| 127 | 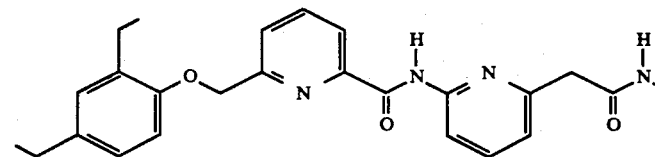 |
| 128 | 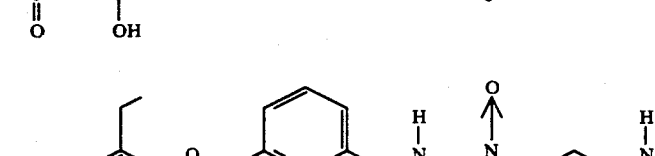 |
| 129 | 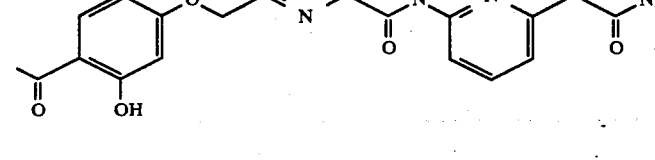 |
| 130 | 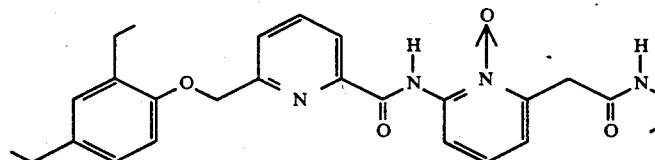 |

TABLE 103

$^1$H-NMR δ ppm 126 (solvent:CDCl$_3$) 1.28(3H, t, J=7.4Hz), 2.58(3H, s), 2.71(2H, q, J=7.4Hz), 3.02(2H, t, J=5.5Hz), 4.05(2H, t, J=5.5Hz), 5.34(2H, s), 6.49(1H, s), 6.98(1H, d, J=7.6Hz), 7.50(1H, s), 7.70(1H, d, J=7.9Hz), 7.72(1H, dd, J=7.9, 7.9Hz), 7.98(1H, d, J=7.9, 7.6Hz), 8.27(1H, d, J=7.6Hz), 8.30(1H, d, J=8.2Hz)

127 (solvent:CDCl$_3$) 1.10(3H, t, J=7.1Hz), 1.17(3H, t, J=7.3Hz), 1.27(3H, t, J=8.1Hz), 2.59(3H, s), 2.71(2H, q, J=7.2Hz), 2.84(1H, dd, J=16.8, 4.6Hz), 3.02(1H, dd, J=16.8, 4.3Hz), 3.75(2H, s), 4.00(2H, q, J=7.1Hz), 4.16(2H, q, J=7.0Hz), 4.85(1H, dt, J=7.9, 4.6Hz), 5.39(2H, s), 6.49(1H, s), 7.05(1H, dd, J=7.6, 0.6Hz), 7.51(1H, s), 7.72(1H, d, J=7.6Hz), 7.75(1H, dd, J=7.9, 7.9Hz), 7.99(1H, dd, J=7.6, 7.9Hz), 8.26(1H, dd, J=8.6, 1.0Hz), 8.34(1H, dd, J=8.2, 0.7Hz)

128 (solvent:DMSO-d$_6$) 0.90(3H, d, J=7.6Hz), 0.91(3H, d, J=7.6Hz), 1.19(3H, t, J=7.3Hz), 2.07(1H, m), 2.58(3H, s), 2.65(2H, q, J=7.3Hz) 3.92(2H, ABq, J=21.8, 15.5Hz), 4.18 (1H, dd, J=8.3, 5.6Hz), 5.42(2H, s), 6.62(1H, s), 7.29 (1H, dd, J=8.3, 2.0Hz), 7.48(1H, t, J=8.3Hz), 7.68(1H, s), 7.85(1H, m), 8.20(2H, m), 8.45(1H, dd, J=8.3, 2.0Hz), 8.46 (1H, d, J=8.3Hz), 12.17(1H, s), 12.51(1H, s), 12.60(1H, s)

129 (solvent:CDCl$_3$) 0.88(3H, t, J=7.3Hz), 0.89(3H, t, J=7.3Hz), 1.27(3H, t, J=7.6Hz), 2.18(1H, m), 2.59(3H, s), 2.71 (2H, q, J=7.6Hz) 3.65(3H, s), 4.04(2H, Abq, J=17.5, 13.2Hz), 4.40(1H, m), 5.36(2H, s) 6.45(1H, s), 7.18(1H, dd, J=8.3, 2.0Hz), 7.41(1H, t, J=8.3Hz), 7.51(1H, s), 7.74 (1H, d, J=7.9Hz), 8.00(1H, t, J=7.9Hz), 8.25(1H, d, J=7.9Hz), 8.63(1H, dd, J=8.3, 2.0Hz), 8.78(1H, d, J=8.6Hz), 12.38(1H, s), 12.62(1H, s)

130 (solvent:DMSO-d$_6$) 1.10(3H, d, J=7.3Hz), 1.22(3H, t, J=7.6Hz), 2.58(3H, s), 2.67(2H, q, J=7.6Hz), 3.76(2H, ABq, J=20.5, 14.9Hz), 4.17(1H, br), 4.26(1H, m), 4.95(1H, m), 5.47(2H, s), 6.63(1H, s), 7.20(1H, d, J=7.6Hz), 7.69(1H, s), 7.82(2H, m), 8.18(4H, m), 10.36(1H, s), 12.50(1H, br), 12.55 (1H, s)

TABLE 104

| Ex. No. | Structural formula |
|---|---|
| 131 | [structure: 2-ethyl-4-acetyl-5-hydroxyphenoxy-methyl-pyridine-carboxamide linked to N-oxide pyridyl-acetamide-threonine methyl ester] |
| 132 | [structure: same aryl-pyridine-carboxamide linked to N-oxide pyridyl-acetamide-alanine] |
| 133 | [structure: same aryl-pyridine-carboxamide linked to N-oxide pyridyl-acetamide-α-aminobutyric acid] |
| 134 | [structure: same aryl-pyridine-carboxamide linked to N-oxide pyridyl-acetamide-α-aminobutyric acid methyl ester] |
| 135 | [structure: same aryl-pyridine-carboxamide linked to N-oxide pyridyl-acetamide-aspartic acid] |

TABLE 105

$^1$H-NMR δ ppm 131 (solvent:CDCl$_3$) 1.16(3H, d, J=7.3Hz), 1.26(3H, t, J=7.6Hz), 2.57(3H, s), 2.69(2H, q, J=7.6Hz), 3.01(1H, br), 3.69 (3H, s), 4.05(2H, ABq, J=20.1Hz, 13.9Hz), 4.50(1H, m), 4.54(1H, m), 5.36(2H, s), 6.49(1H, s), 7.20(1H, dd, J=8.3Hz, 1.7Hz), 7.41(1H, t, J=8.3Hz), 7.48(1H, s), 7.72(1H, d, J=7.9Hz), 7.98(1H, t, J=7.9Hz), 8.21(1H, d, J=7.9Hz), 8.51 (1H, d, J=8.6Hz), 8.60(1H, dd, J=8.3, 1.7Hz), 12.34(1H, s), 12.64(1H, s)

132 (solvent:DMSO-d$_6$) 1.19(3H, t, J=7.3Hz), 1.31(3H, d, J=7.3Hz), 2.58(3H, s), 2.64(2H, q, J=7.6Hz), 3.85(2H, m), 4.24 (1H, m), 5.43(2H, s), 6.63(1H, s), 7.31(1H, dd, J=8.3, 1.7Hz), 7.47(1H, t, J=8.3Hz), 7.68(1H, s), 7.85(1H, m), 8.21 (2H, m), 8.46(1H, dd, J=8.3, 1.7Hz), 8.54(1H, d, J=7.9Hz), 12.15(1H, s), 12.50(1H, s), 12.55(1H, br)

133 (solvent:DMSO-d$_6$) 0.92(3H, t, J=7.6Hz), 1.20(3H, t, J=7.6Hz), 1.6–1.9(1H, m), 2.58(3H, s), 2.65(2H, q, J=7.6Hz), 3.89(2H, ABq, J=20.8, 15.8Hz), 4.17(1H, m), 5.42(2H, s), 6.63(1H, s), 7.30(1H, dd, J=8.3Hz, 2.0Hz), 7.47(1H, t, J=8.3Hz), 7.68(1H, s), 7.85(2H, m), 8.21(2H, m), 8.45(1H, dd, J=8.3, 2.0Hz), 8.50(1H, d, J=7.9Hz), 12.16(1H, s), 12.50 (1H, s), 12.55(1H, br)

134 (solvent:CDCl$_3$) 0.89(3H, t, J=7.3Hz), 1.27(3H, t, J=7.6Hz), 1.70–1.85(2H, m), 2.59(3H, s), 2.71(2H, q, J=7.6Hz), 3.66(3H, s), 4.02(2H, ABq, J=18.8, 13.2Hz), 4.45(1H, m), 5.38(2H, s), 6.48(1H, s), 7.18(1H, dd, J=7.9, 2.0Hz), 7.41 (1H, t, J=7.9Hz), 7.50(1H, s), 7.75(1H, d, J=7.9Hz), 8.00 (1H, t, J=7.9Hz), 8.25(1H, d, J=7.9Hz), 8.61(1H, brd), 8.63 (1H, dd, J=7.9Hz, 2.0Hz), 12.33(1H, s), 12.63(1H, s)

135 (solvent:DMSO-d$_6$) 1.20(3H, t, J=7.6Hz), 2.58(3H, s), 2.65 (2H, q, J=7.6Hz), 2.7–2.9(2H, m), 3.87(2H, s), 4.58(1H, m), 5.43(2H, s), 6.64(1H, s), 7.30(1H, dd, J=8.3, 2.0Hz), 7.47(1H, t, J=8.3Hz), 7.68(1H, s), 7.84(1H, m), 8.21(1H, m), 8.46(1H, dd, J=8.3Hz, 2.0Hz), 8.61(1H, d, J=7.9Hz), 12.14 (1H, s), 12.51(1H, s), 12.55(2H, br)

TABLE 106

| Ex. No. | Structural formula |
|---|---|
| 136 | |
| 137 | |
| 138 | |
| 139 | |
| 140 | |

TABLE 107

$^1$H-NMR δ ppm 136 (solvent: CDCl$_3$) 1.15(3H, t, J=7.3Hz), 1.17(3H, t, J=7.3Hz), 1.27(3H, t, J=7.6Hz), 2.59(3H, s), 2.71(2H, q, J=7.6Hz), 2.80-2.95(2H, m), 3.93-4.16(6H, m), 4.81(1H, m), 5.39(2H, s), 6.47(1H, s), 7.18(1H, d, J=8.3Hz), 7.41(1H, t, J=8.3Hz), 7.51(1H, s), 7.76(1H, d, J=7.9Hz), 8.01(1H, t, J=7.9Hz), 8.25(1H, d, J=7.9Hz), 8.62(1H, dd, J=8.3, 1.7Hz), 8.69(1H, d, J=7.9Hz), 12.31(1H, s), 12.61(1H, s)

137 (solvent:DMSO-d$_6$) 1.09(3H, d, J=7.6Hz), 1.20(3H, t, J=7.6Hz), 2.58(3H, s), 2.66(2H, q, J=7.6Hz), 3.96(2H, ABq, J=20.8, 15.8Hz), 4.10(1H, br), 4.24(1H, m), 4.90(1H, m), 5.42(2H, s), 6.63(1H, s), 7.31(1H, dd, J=7.9, 2.0Hz), 7.48(1H, t, J=7.9Hz), 7.68(1H, s), 7.85(1H, m), 8.17-8.30(3H, m), 12.16(1H, s), 12.50(1H, s), 12.55(1H, br)

138 (solvent:CDCl$_3$) 1.18(2H, d, J=6.6Hz), 1.27(3H, t, J=7.6Hz), 2.58(3H, s), 2.69(2H, q, J=7.6Hz), 3.72(3H, s), 3.80(2H, s), 4.34(4H, m), 4.61(1H, m), 5.37(2H, s), 6.49(1H, s), 7.06(1H, d, J=7.9Hz), 7.49(1H, s), 7.70(1H, d, J=7.9Hz), 7.76(1H, t, J=7.9Hz), 7.97(1H, t, J=7.9Hz), 8.25(1H, d, J=7.9Hz), 8.29(1H, d, J=7.9Hz), 8.46(1H, brd, J=8.3Hz), 10.57(1H, s), 12.70(1H, s)

139 (solvent:CDCl$_3$) 1.27(3H, t, J=7.6Hz), 1.41(3H, d, J=7.3Hz), 2.59(3H, s), 2.71(2H, q, J=7.6Hz), 3.66(3H, s), 4.01(2H, ABq, J=29.7Hz, 13.2Hz), 4.51(1H, m), 5.40(2H, s), 6.50(1H, s), 7.18(1H, dd, J=8.3, 2.0Hz), 7.41(1H, t, J=8.3Hz), 7.50(1H, s), 7.75(1H, d, J=7.9Hz), 8.00(1H, t, J=7.9Hz), 8.26(1H, d, J=7.9Hz), 8.52(1H, d, J=7.6Hz), 8.64(1H, dd, J=8.3, 2.0Hz), 12.31(1H, s), 12.63(1H, s)

140 (solvent:DMSO-d$_6$) 1.20(3H, t, J=7.6Hz), 1.90-2.52(4H, m), 2.58(3H, s), 2.66(2H, q, J=7.6Hz), 3.70(2H, m), 3.99(2H, ABq, J=29.7, 16.2Hz), 4.29(1H, m), 5.24(2H, s), 6.63(1H, s), 7.33(1H, dd, J=7.6, 2.0Hz), 7.47(1H, t, J=8.3Hz), 7.68(1H, s), 7.85(1H, dd, J=5.6, 3.3Hz), 8.20(2H, s), 8.46(1H, dd, J=8.3, 2.0Hz), 12.14(1H, s), 12.51(1H, s)

TABLE 108

| Ex. No. | Structural formula |
|---|---|
| 141 | *(structure)* |
| 142 | *(structure)* |

TABLE 109

¹H-NMR δ ppm

141 (solvent:CDCl₃) 1.27(3H, t, J=7.6Hz), 1.9-2.3(4H, m), 2.59(3H, s), 2.71(2H, q, J=7.6Hz), 3.73(3H, s), 3.6-3.9(2H, m), 3.87(2H, m), 4.55(1H, m), 5.33(2H, s), 6.47(1H, s), 7.18(1H, d, J=7.9Hz), 7.51(1H, s), 7.69(1H, d, J=7.9Hz), 7.74(1H, t, J=7.9Hz), 7.98(1H, t, J=7.9Hz), 8.27(1H, d, J=7.9Hz), 8.31(1H, d, J=7.9Hz), 10.34(1H, s), 12.67(1H, s)

142 (solvent:CDCl₃) 1.27(3H, t, J=7.6Hz), 1.9-2.3(4H, m), 2.58(3H, s), 2.70(2H, q, J=7.6Hz), 3.74(3H, s), 3.7-3.9(2H, m), 3.90(1H, d, J=15.8Hz), 4.26(1H, d, J=15.8Hz), 4.61(1H, m), 5.35(2H, s), 6.46(1H, s), 7.25(1H, brd), 7.37(1H, t, J=7.9Hz), 7.50(1H, s), 7.73(1H, d, J=7.9Hz), 7.98(1H, t, J=7.9Hz), 8.24(1H, d, J=7.9Hz), 8.59(1H, d, J=7.9Hz), 12.29(1H, s), 12.65(1H, s)

TABLE 110

| Ex. No. | Structural formula |
|---|---|
| 143 | *(structure)* |
| 144 | *(structure)* |
| 145 | *(structure)* |
| 146 | *(structure)* |

TABLE 110-continued

| Ex. No. | Structural formula |
|---|---|
| 147 | (structure) |

TABLE 111

| | $^1$H-NMR δ ppm |
|---|---|
| 143 | (solvent:CDCl$_3$) 1.26(3H, t, J=7.4Hz), 1.27(3H, t, J=7.4Hz), 1.30(3H, t, J=7.0Hz), 2.58(3H, t), 2.69(2H, q, J=7.4Hz), 2.97(1H, dd, J=16.8, 4.6Hz), 3.13(1H, dd, J=16.8, 4.0Hz), 4.19(2H, qd, J=7.3, 3.0Hz), 4.27(2H, q, J=7.3, 3.0Hz) 5.06(1H, td, J=8.3, 5.0Hz), 5.27(1H, s), 6.46(1H, s), 7.49(1H, s), 7.64(1H, dd, J=7.6, 1.0Hz), 7.91(1H, dd, J=7.6, 7.6Hz), 8.14(1H, dd, J=7.6, 1.0Hz) |
| 144 | (solvent:CDCl$_3$) 1.26(3H, t, J=7.6Hz), 1.32(3H, t, J=7.3Hz), 2.58(3H, s), 2.68(2H, q, J=7.6Hz), 4.2-4.3(4H, m), 5.26(2H, s), 6.45(1H, s), 7.49(1H, s), 7.64(1H, d, J=7.6Hz), 7.92(1H, dd, J=6.9, 7.6Hz), 8.15(1H, d, J=6.9Hz), 12.66 (1H, s) |
| 145 | (solvent:CDCl$_3$) 1.25(3H, t, J=7.6Hz), 1.28(3H, t, J=7.3Hz), 2.6-2.7(4H, m), 3.7-3.8(2H, m), 4.1-4.2(2H, q, J=7.3Hz), 5.24(2H, s), 6.45(1H, s), 7.49(1H, s), 7.61(1H, d, J=7.9Hz), 7.90(1H, dd, J=6.6, 7.9Hz), 8.14(1H, d, J=6.6Hz), 8.42(1H, br), 12.66(1H, s) |
| 146 | (solvent:CDCl$_3$) 1.02(6H, dd, J=4.0Hz, 6.9Hz, 1.26(3H, t, J=7.6Hz), 2.2-2.4(1H, m), 2.58(3H, s), 2.69(2H, q, J=7.6Hz), 3.78(3H, s), 4.75(1H, dd, J=5.3, 9.2Hz), 5.29(2H, s), 6.49(1H, s), 7.50(1H, s), 7.64(1H, d, J=7.9Hz), 7.91(1H, dd, J=7.9, 7.9Hz), 8.15(1H, d, J=7.9Hz), 8.44(1H, d, J=9.2Hz), 12.66(1H, s) |
| 147 | (solvent:CDCl$_3$) 1.25(3H, t, J=7.6Hz), 2.58(3H, s), 2.68(2H, q, J=7.6Hz), 3.85(3H, s), 4.0-4.2(2H, m), 4.8-4.9(1H, m), 5.29(2H, s), 6.51(1H, s), 7.49(1H, s), 7.65(1H, d, J=7.6Hz), 7.92(1H, dd, J=7.6, 7.9Hz), 8.15(1H, d, J=7.9Hz), 8.80(1H, d, J=7.9Hz), 12.70 (1H, s) |

TABLE 112

| Ex. No. | Structural formula |
|---|---|
| 148 | (structure) |
| 149 | (structure) |
| 150 | (structure) |
| 151 | (structure) |

TABLE 112-continued

| Ex. No. | Structural formula |
|---|---|
| 152 | (structure: 2-ethyl-4-acetyl-5-hydroxyphenoxymethyl-pyridine-2-carboxamide linked to alanine methyl ester) |

TABLE 113

| | ¹H-NMR δ ppm |
|---|---|
| 148 | (solvent:CDCl₃) 1.26(3H, t, J=7.6Hz), 1.32(3H, t, J=7.3Hz), 2.0–2.2(1H, m), 2.12(3H, s), 2.3–2.4(1H, m), 2.5–2.7 (4H, m), 2.58(3H, s), 4.26(2H, q, J=7.3Hz), 4.8–5.0(1H, m), 5.29(2H, s), 6.47(1H, s), 7.50(1H, s), 7.64(1H, dd, J=1.0, 7.6Hz), 7.91(1H, dd, J=7.6, 7.6Hz), 8.14(1H, dd, J=1.0Hz, 7.6Hz), 8.52(1H, d, J=8.6Hz), 12.66(1H, s) |
| 149 | (solvent:CDCl₃) 1.25(3H, t, J=7.6Hz), 2.58(3H, s), 2.67(2H, q, J=7.6Hz), 3.26(2H, dd, J=1.8Hz, 6.3Hz), 3.75(3H, s), 5.07(1H, dt, J=8.3, 6.3Hz), 5.22(2H, s), 6.45(1H, s), 7.1–7.4(5H, m), 7.50(1H, s), 7.62(1H, d, J=7.3Hz), 7.89(1H, dd, J=6.9Hz, 7.3Hz), 8.11(1H, d, J=6.9Hz), 8.41(1H, d, J=8.3Hz), 12.67(1H, s) |
| 150 | (solvent:CDCl₃) 1.25(3H, t, J=7.6Hz), 2.58(3H, s), 2.68(2H, q, J=7.6Hz), 3.1–3.2(2H, m), 3.76(3H, s), 5.02(1H, dt, J=8.6Hz, 5.9Hz), 5.21(2H, d, J=2.0Hz), 6.09(1H, s), 6.42(1H, s), 6.76(1H, dd, J=2.3Hz, 8.9Hz), 7.02(1H, d, J=8.9Hz), 7.50(1H, s), 7.61(1H, d, J=7.6Hz), 7.88(1H, dd, J=7.5Hz, 7.6Hz), 8.10(1H, d, J=7.5Hz), 8.40(1H, d, J=8.6Hz), 12.63(1H, s) |
| 151 | (solvent:CDCl₃) 1.25(3H, t, J=7.6Hz), 2.58(3H, s), 2.68(2H, q, J=7.6Hz), 3.30(2H, d, J=5.6Hz), 3.79(3H, s), 5.0–5.1(1H, m), 5.27(2H, d, J=4.6Hz), 6.42(1H, s), 6.86(1H, d, J=1.3Hz), 7.49(1H, s), 7.6–7.7(2H, m), 7.89(1H, dd, J=7.6Hz, 7.6Hz), 8.12(1H, dd, J=1.0Hz, 7.9Hz), 8.8–8.9(1H, m), 12.80(1H, s) |
| 152 | (solvent:CDCl₃) 1.26(3H, t, J=7.6Hz), 1.57(3H, d, J=6.9Hz), 2.58(3H, s), 2.69(2H, q, J=7.6Hz), 3.80(3H, s), 4.82 (1H, dq, J=6.9Hz, 8.3Hz), 5.28(2H, s), 6.47(1H, s), 7.50(1H, s), 7.63(1H, dd, J=1.0Hz, 7.9Hz), 7.91(1H, dd, J=7.9Hz, 7.9Hz), 8.14(1H, dd, J=1.0, 7.9Hz), 8.43(1H, d, J=8.3Hz), 12.66(1H, s) |

TABLE 114

| Ex. No. | Structural formula |
|---|---|
| 153 | (structure: 2-ethyl-4-acetyl-5-hydroxyphenoxymethyl-pyridine-2-carboxamide linked to alanine methyl ester) |
| 154 | (structure: 2-ethyl-4-acetyl-5-hydroxyphenoxymethyl-pyridine-2-carboxamide linked to glutamic acid dimethyl ester) |
| 155 | (structure: 2-ethyl-4-acetyl-5-hydroxyphenoxymethyl-pyridine-2-carboxamide linked to glycine-thiazole-acetic acid ethyl ester) |
| 156 | (structure: 2-ethyl-4-acetyl-5-hydroxyphenoxymethyl-pyridine-2-carboxamide linked to β-phenyl-β-amino propionic acid methyl ester) |

TABLE 114-continued

| Ex. No. | Structural formula |
|---|---|
| 157 | (acetyl-ethyl-hydroxyphenoxy)methyl-pyridine-carboxamide-N-(CH$_2$)$_3$-CO-OMe |

TABLE 115

| | $^1$H-NMR δ ppm |
|---|---|
| 153 | (solvent:CDCl$_3$) 1.26(3H, t, J=7.6Hz), 1.57(3H, d, J=7.3Hz), 2.58(3H, s), 2.69(2H, q, J=7.6Hz), 3.80(3H, s), 4.82 (1H, dq, J=7.3Hz, 7.9Hz), 5.28(2H, s), 6.45(1H, s), 7.50(1H, s), 7.63(1H, d, J=7.6Hz), 7.91(1H, dd, J=7.6, 7.6Hz), 8.14(1H, d, J=7.6Hz), 8.43(1H, d, J=7.9Hz), 12.66(1H, s) |
| 154 | (solvent:CDCl$_3$) 1.26(3H, t, J=7.6Hz), 2.1–2.5(4H, m), 2.58(3H, s), 2.69(2H, q, J=7.6Hz), 3.66(3H, s), 3.70(3H, s), 4.8–4.9(1H, m), 5.29(2H, s), 6.48(1H, s), 7.50(1H, s), 7.64(1H, dd, J=1.0Hz, 7.6Hz), 7.91(1H, dd, J=7.6Hz, 7.6Hz), 8.13(1H, dd, J=1.0, 7.6Hz), 8.47(1H, d J=8.6Hz), 12.65(1H, s) |
| 155 | (solvent:CDCl$_3$) 1.25(3H, t, J=7.3Hz), 1.26(3H, t, J=7.6Hz), 2.58(3H, s), 2.69(2H, q, J=7.6Hz), 3.68(2H, d, J=1.0Hz), 4.17(2H, q, J=7.3Hz), 4.42(2H, d, J=6.3Hz), 5.26 (2H, s), 6.45(1H, s), 6.82(1H, t, J=1.0Hz), 7.50(1H, s), 7.69(1H, d, J=7.9Hz), 7.96(1H, dd, J=7.9Hz, 8.9Hz), 8.63 (1H, br), 9.80(1H, br), 12.67(1H, s) |
| 156 | (solvent:CDCl$_3$) 1.25(3H, t, J=7.6Hz), 2.58(3H, s), 2.68(2H, q, J=7.6Hz), 2.97(1H, dd, J=6.3Hz, 15.8Hz), 3.09(1H, dd, J=6.6, 15.8Hz), 3.64(3H, s), 5.27(2H, s), 5.64 (1H, ddd, J=6.3Hz, 6.6Hz, 8.9Hz), 6.49(1H, s), 7.2–7.5(5H, m), 7.49(1H, s), 7.63(1H, d, J=7.3Hz), 7.90(1H, dd, J=7.3Hz. 7.3Hz), 8.15(1H, d, J=7.3Hz), 8.80(1H, d, J=8.9Hz), 12.66(1H, s) |
| 157 | (solvent:CDCl$_3$) 1.25(3H, t, J=7.6Hz), 1.9–2.1(2H, m), 2.45(2H, t, J=7.6Hz), 2.58(3H, s), 2.68(2H, q, J=7.6Hz), 3.54(2H, m), 3.68(3H, s), 5.25(2H, s), 6.47(1H, s), 7.50(1H, s), 7.61(1H, d, J=7.6Hz), 7.90(1H, dd, J=7.6Hz, 7.9Hz), 8.10(1H, br), 8.15(1H, d, J=7.9Hz) |

TABLE 116

| Ex. No. | Structural formula |
|---|---|
| 158 | (acetyl-ethyl-hydroxyphenoxy)methyl-pyridine-carboxamide-N-(CH$_2$)$_5$-CO-OMe |
| 159 | (acetyl-ethyl-hydroxyphenoxy)methyl-pyridine-carboxamide-N-CH$_2$-CH(OH)-(4-hydroxyphenyl) |
| 160 | (acetyl-ethyl-hydroxyphenoxy)methyl-pyridine-carboxamide-N-CH$_2$CH$_2$OH |
| 161 | (acetyl-ethyl-hydroxyphenoxy)methyl-pyridine-carboxamide-N,N-bis(CH$_2$CH$_2$OH) |

TABLE 116-continued

| Ex. No. | Structural formula |
|---|---|
| 162 | (structure: 2-ethyl-4-acetyl-5-hydroxyphenyl-O-CH2-pyridine-2-C(O)NH-CH2CH2CH2-OH) |

TABLE 117

$^1$H-NMR δ ppm 158 (solvent:CDCl$_3$) 1.25(3H, t, J=7.6Hz), 1.3–1.5(2H, m), 1.6–1.8(4H, m), 2.34(2H, t, J=7.6Hz), 2.58(3H, s), 2.68(2H, q, J=7.6Hz), 3.4–3.5(2H, m), 3.67(3H, s), 5.25(2H, s), 6.47(1H, s), 7.49(1H, s), 7.51(1H, d, J=7.9Hz), 7.90(1H, dd, J=7.9Hz, 7.9Hz), 8.02(1H, br), 8.16(1H, d, J=7.9Hz), 12.67(1H, s)

159 (solvent:DMSO-d$_6$) 1.19(3H, t, J=7.6Hz), 2.52(3H, s), 2.60 (2H, q, J=7.6Hz), 3.5–3.7(2H, m), 4.6–4.8(1H, m), 5.36(2H, s), 5.57(1H, d, J=4.3Hz), 6.58(1H, s), 6.6–6.7(1H, m), 6.8–6.9(2H, m), 7.1–7.2(1H, m), 7.7–7.8(2H, m), 7.9–8.2(2H, m), 8.5–8.6(1H, m), 9.34(1H, s), 12.56(1H, s)

160 (solvent:DMSO-d$_6$) 1.25(3H, t, J=7.6Hz), 2.59(3H, s), 2.67 (2H, q, J=7.6Hz), 2.73(1H, t, J=5.4Hz), 3.6–3.7(2H, m), 3.8–3.9(2H, m), 5.25(2H, m), 6.49(1H, s), 7.49(1H, s), 7.62(1H, d, J=7.6Hz), 7.91(1H, dd, J=7.6Hz, 7.6Hz), 8.16(1H, d, J=7.6Hz), 8.40(1H, br). 12.69(1H, s)

161 (solvent:DMSO-d$_6$) 1.24(3H, t, J=7.6Hz), 2.59(3H, s), 2.68(2H, q, J=7.6Hz), 3.6–4.0(9H, m), 5.25(2H, s), 5.84(1H, t, J=4.6Hz), 6.43(1H, s), 7.49(1H, s), 7.62(1H, d, J=7.6Hz), 7.81(1H, d, J=7.6Hz), 7.95(1H, dd, J=7.6Hz, 7.6Hz), 12.62(1H, s)

162 (solvent:DMSO-d$_6$) 1.25(3H, t, J=7.6Hz), 1.8–1.9(2H, m), 2.58(3H, s), 2.67(2H, q, J=7.6Hz), 3.30(1H, t, J=6.4Hz), 5.25(2H, s), 6.50(1H, s), 7.63(1H, d, J=7.6Hz), 7.91(1H, dd, J=7.6Hz, 7.6Hz), 8.16(1H, d, J=7.6Hz), 8.30(1H, br), 12.71(1H, s)

TABLE 118

| Ex. No. | Structural formula |
|---|---|
| 163 | (structure: 2-ethyl-4-acetyl-5-hydroxyphenyl-O-CH2-pyridine-2-C(O)N(Et)-CH2CH2-OH) |
| 164 | (structure: 2-ethyl-4-acetyl-5-hydroxyphenyl-O-CH2-phenyl-C(O)NH-CH2-CO2Et) |
| 165 | (structure: 2-ethyl-4-acetyl-5-hydroxyphenyl-O-CH2-phenyl-C(O)NH-CH(CH3)-CO2Me) |
| 166 | (structure: 2-ethyl-4-acetyl-5-hydroxyphenyl-O-CH2-phenyl-C(O)NH-CH(CO2Et)-CH2-CO2Et) |
| 167 | (structure: 2-ethyl-4-acetyl-5-hydroxyphenyl-O-CH2-phenyl-C(O)NH-CH(CO2Me)-CH2OH) |

TABLE 119

$^1$H-NMR δ ppm 163 (solvent:DMSO-d$_6$) 1.25(3H, t, J=7.6Hz), 1.32(3H, t, J=7.1Hz), 2.57(3H, s), 2.68(2H, q, J=7.6Hz), 3.4–4.0(6H, m), 5.25(2H, s), 6.45(1H, s), 7.49(1H, s), 7.5–7.9(3H, m), 12.61 (1H, s)

164 (solvent:CDCl$_3$) 1.22(3H, t, J=7.4Hz), 1.32(3H, t, J=7.1Hz), 2.57(3H, s), 2.63(2H, q, J=7.4Hz), 4.26(2H, s), 4.27(2H, q, J=7.1Hz), 5.13(2H, s), 6.44(1H, s), 7.46(1H, s), 7.49(1H, dd, J=7.6, 7.6Hz), 7.59(1H, d, J=7.6Hz), 7.77(1H, d, J=7.6Hz), 7.90(1H, s)

165 (solvent:CDCl$_3$) 1.22(3H, t, J=7.4Hz), 1.54(2H, d, J=7.0Hz), 2.57(3H, s), 2.63(2H, q, J=7.4Hz), 3.80(3H, s), 4.82(1H, q, J=7.0Hz), 5.14(2H, s), 6.44(1H, s), 7.46(1H, s), 7.48(1H, dd, J=7.6, 7.6Hz), 7.58(1H, q, J=7.6 Hz), 7.76(1H, d, J=7.6Hz), 7.88(1H, s)

166 (solvent:CDCl$_3$) 1.22(3H, t, J=7.6Hz), 1.26(3H, t, J=7.1Hz), 1.29(3H, t, J=7.1Hz), 2.57(3H, s), 2.64(2H, q, J=7.4Hz), 2.97(1H, dd, J=17.2, 4.3Hz), 3.14(1H, dd, J=17.2, 4.3Hz), 4.16(2H, q, J=7.1Hz), 4.27(2H, q, J=7.1Hz), 5.04 (1H, td, J=4.3, 7.9Hz), 5.15(1H, s), 6.45(1H, s), 7.46(1H, s), 7.49(1H, dd, J=7.6, 7.6Hz), 7.59(1H, d J=7.6Hz), 7.77(1H, d, J=7.6Hz), 7.90(1H, s)

167 (solvent:CDCl$_3$) 1.22(3H, t, J=7.4Hz), 2.57(3H, s), 2.63(2H, q, J=7.4Hz), 3.83(3H, s), 4.1–4.2(2H, br), 4.89(1H, dt, J=7.3, 3.6Hz), 5.14(2H, s), 6.44(1H, s), 7.47(1H, s), 7.49(1H dd, J=7.6, 7.6Hz), 7.60(1H, d, J=7.6Hz), 7.80(1H, d, J=7.6Hz), 7.91(1H, s)

TABLE 120

| Ex. No. | Structural formula |
|---|---|
| 168 | 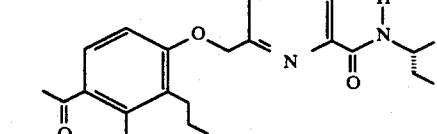 |
| 169 | 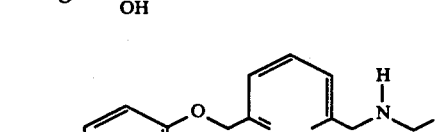 |
| 170 | 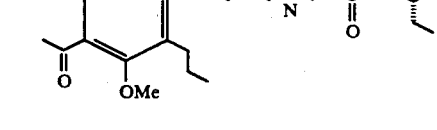 |
| 171 | 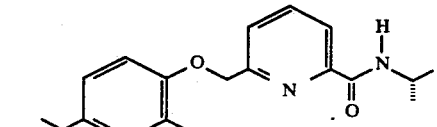 |

TABLE 120-continued

| Ex. No. | Structural formula |
|---|---|
| 172 | 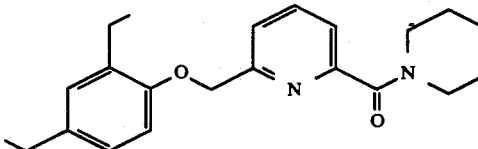 |

TABLE 121

$^1$H-NMR δ ppm 168 (solvent:CDCl$_3$) 0.98(3H, t, J=7.3Hz), 1.27(3H, t, J=7.3Hz), 1.30(3H, t, J=7.1Hz), 1.5–1.7(2H, m), 2.58(3H, s), 2.76(2H, t, J=7.6Hz), 2.98(1H, dd, J=16.8, 4.9Hz), 3.14(1H, dd, J=16.8, 4.9Hz), 4.1–4.4(4H, m), 5.06(1H, dt, J=8.6, 4.9Hz), 5.32(2H, s), 6.50(1H, d, J=8.9Hz), 7.61(1H, d, J=8.9Hz), 7.66(1H, d, J=8.9Hz), 7.66(1H, d, J=7.9Hz), 7.91(1H, dd, J=7.6, 7.9Hz), 8.13(1H, d, J=7.6Hz)

169 (solvent:CDCl$_3$) 1.02(3H, t, J=7.4Hz), 1.27(3H, t, J=7.1Hz), 1.30(3H, t, J=7.1Hz), 1.6–1.7(2H, m), 2.62(3H, t), 2.74(2H, t, J=7.9Hz), 2.97(1H, dd, J=17.0, 4.9Hz), 3.13(1H, dd, J=17.0, 4.9Hz), 4.1–4.4(4H, m), 5.06(1H, dt, J=8.3, 4.9Hz), 5.29(2H, s), 6.74(1H, d, J=8.8Hz), 7.57(1H, d, J=8.8Hz), 7.66(1H, d, J=7.9Hz), 7.91(1H, dd, J=7.6, 7.9Hz), 8.14(1H, d, J=7.6Hz)

170 (solvent:CDCl$_3$) 1.02(3H, t, J=7.3Hz), 1.32(3H, t, J=7.3Hz), 1.56(3H, d, J=7.3Hz), 1.6–1.7(2H, m), 2.62(3H, s), 2.75(2H, t, J=7.9Hz), 3.78(3H, s), 4.26(2H, q, J=7.2Hz), 4.79(1H, qd, J=7.8, 7.8Hz), 5.29(2H, s), 6.73(1H, d, J=7.6Hz), 7.57(1H, d J=8.6Hz), 7.64(1H, d, J=7.9Hz), 7.91(1H, dd, J=7.6, 7.9Hz), 8.14(1H, d, J=7.6Hz)

171 (solvent:CDCl$_3$) 1.24(3H, t, J=7.2Hz), 1.32(3H, t, J=7.1Hz), 1.56(3H, d, J=1.0Hz), 2.58(3H, s), 2.69(2H, q, J=7.5Hz), 3.88(3H, s), 4.26(2H, q, J=7.2Hz), 4.81(1H, qd, J=7.7, 7.7Hz), 5.32(2H, s), 6.51(1H, s), 7.72(1H, s), 7.70(1H, d, J=8.3Hz), 7.93(1H, dd, J=7.9, 7.6Hz), 8.15(1H, d, J=7.9Hz)

172 (solvent:CDCl$_3$) 1.24(3H, t, J=7.5Hz), 1.6–2.2(4H, m), 2.57(3H, s), 2.67(2H, q, J=7.5Hz), 3.5–5.4(7H, m), 6.44–6.46(2H, m), 7.5–8.0(4H, m)

TABLE 122

| Ex. No. | Structural formula |
|---|---|
| 173 | 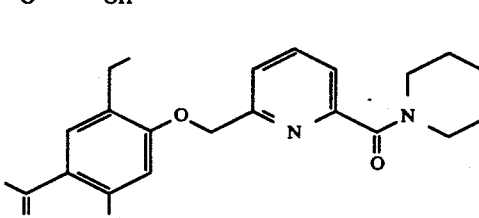 |
| 174 | 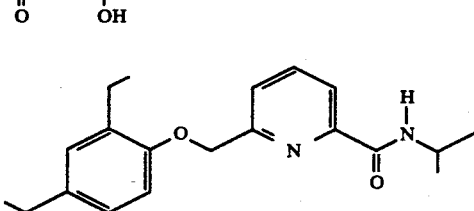 |
| 175 |  |

TABLE 122-continued

| Ex. No. | Structural formula |
|---|---|
| 176 |  |
| 177 | 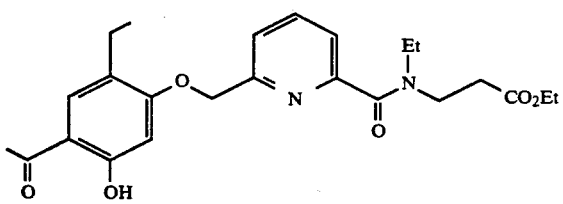 |

TABLE 123

¹H-NMR δ ppm 173 (solvent:CDCl₃) 1.25(3H, t, J=7.5Hz), 1.7-2.1(5H, m), 2.57 (3H, s), 2.67(2H, q, J=7.5Hz), 3.0-3.3(2H, m), 3.72(3H, s), 3.8-4.0(2H, m), 4.5-4.7(2H, m), 5.24(2H, s), 6.44(1H, s), 7.48(1H, s), 7.53(1H, d, J=7.6Hz), 7.56(1H, d, J=7.6Hz), 7.84(1H, dd, J=7.9, 7.9Hz)

174 (solvent:CDCl₃) 1.25(3H, td, J=7.6, 2.0Hz), 1.5-2.0(4H, m), 2.57(3H, s), 2.68(2H, q, J=7.6Hz), 3.61(1.5H, s), 3.73(1.5H, s), 2.5-5.0(5H, m), 5.24(2H, s), 6.44(1H, s), 7.48(1H, s), 7.5-8.0(3H, m)

175 (solvent:CDCl₃) 1.26(3H, t, J=7.4Hz), 1.38(2H, d, J= 6.9Hz), 2.58(3H, s), 2.5-2.7(4H, m), 3.72(3H, s), 4.5-4.6(1H, m), 5.27(2H, s), 6.48(1H, s), 7.49(1H, s), 7.61(1H, d, J= 7.9Hz), 7.89(1H, dd, J=7.9, 7.6Hz), 8.15(1H, d, J=7.6Hz)

176 (solvent:CDCl₃) 1.22(3H, t, J=6.9Hz), 1.25(3H, t, J= 7.1Hz), 1.29(3H, t, J=7.1Hz), 2.57(3H, s), 2.68(2H, q, J= 7.4Hz), 2.78(1H, t, J=7.1Hz), 3.44(1H, q, J=7.1Hz), 3.58 (1H, q, J=7.1Hz), 3.70(1H, t, J=7.4Hz), 3.79(1H, t, J= 7.4Hz), 4.10(1H, q, J=7.1Hz), 4.18(1H, q, J=7.1Hz), 5.21 (1H, s), 5.23(1H, s), 6.43(1H, s), 7.48(1H, s), 7.5-7.9(3H, m), 2.84(1H, t, J=7.1Hz)

177 (solvent:CDCl₃) 1.25(3H, t, J=7.4Hz), 1.29(3H, d, J= 6.3Hz), 2.58(3H, s), 2.69(2H, q, J=7.4Hz), 4.4-4.6(1H, m), 4.7-4.9(1H, m), 5.30(2H, s), 6.50(1H, s), 7.50(1H, s), 7.66 (1H, d, J=7.6Hz), 7.93(1H, dd, J=7.6, 7.6Hz), 8.13(1H, d, J=7.6Hz)

TABLE 124

| Ex. No. | Structural formula |
|---|---|
| 178 | 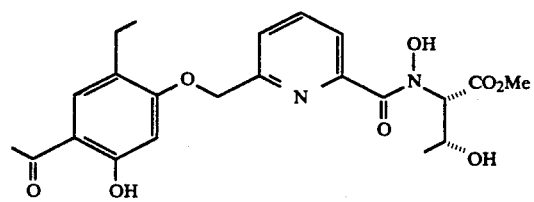 |

TABLE 125

¹H-NMR δ ppm 178 (solvent:CDCl₃) 1.23(1.2H, t, J=7.6Hz), 1.26(1.8H, t, J= 7.6Hz), 2.1-2.6(2H, m), 2.59(3H, s), 2.8-3.0(2H, m), 3.8-4.8 (3H, m), 5.3-5.4(3H, m), 6.44(0.6H, s), 6.48(0.4H, s), 7.5-8.1 (3H, s)

TABLE 126

| ¹H-NMR | δppm |
|---|---|
| 179 | ![structure 179] |
| 180 | ![structure 180] |
| 181 | ![structure 181] |
| 182 | ![structure 182] |
| 183 | ![structure 183] |

TABLE 127

| | $^1$H-NMR δ ppm |
|---|---|
| 179 | (solvent:CD$_3$OD/CDCl$_3$(1/4)) 1.26(3H, t, J=7.4Hz), 2.60 (3H, s), 2.70(2H, q, J=7.4Hz), 2.97(1H, dd, J=17.5, 4.8Hz), 3.15(1H, dd, J=17.5, 4.8Hz), 5.00(1H, t, J=8.9Hz), 5.29(2H, s), 6.47(1H, s), 7.53(1H, s), 7.68(1H, d, J=7.9Hz), 7.95(1H, dd, J=7.9, 7.6Hz), 8.11(1H, d, J=7.6Hz) |
| 180 | (solvent:d$_6$-DMSO) 1.18(3H, t, J=7.6Hz), 2.58(3H, S), 2.62(2H, q, J=7.6Hz), 4.00(2H, d, J=5.9Hz), 5.36(2H, s), 6.57(1H, s), 7.69(1H, s), 7.73(1H, d, J=6.3Hz), 8.01(1H, d, J=6.3Hz), 8.10(1H, dd, J=6.3Hz, 6.3Hz), 8.88(1H, t, J=5.9Hz), 12.55(1H, s) |
| 181 | (solvent:d$_6$-DMSO) 1.18(3H, s, J=7.6Hz), 2.58(3H, s), 2.61(2H, q, J=7.6Hz), 2.69(2H, q, J=7.6Hz), 3.4–3.5(2H, m), 5.35(2H, s), 6.57(1H, s) 7.69(1H, s), 7.70(1H, dd, J= 1.0Hz, 7.6Hz), 7.99(1H, dd, J=1.0Hz, 7.6Hz), 8.07(1H, dd, J=7.6Hz, 7.6Hz), 8.72(1H, t, J=5.9Hz), 12.54(1H, br) |
| 182 | (solvent:d$_6$-DMSO) 0.91(6H, t, J=6.4Hz), 1.18(3H, t, J=7.6Hz), 2.1–2.2(1H, m), 2.57(3H, s), 2.63(1H, q, J=7.6Hz), 4.41(1H, dd, J=5.1Hz, 8.9Hz), 5.42(2H, s), 6.63(1H, s), 7.68(1H, s), 7.76(1H, d, J=6.6Hz), 8.01(1H, d, J=6.9Hz), 8.11(1H, dd, J=6.6Hz, 6.9Hz), 8.38(1H, d, J=8.9Hz), 12.55(1H, s) |
| 183 | (solvent:d$_6$-DMSO) 1.19(3H, t, J=7.6Hz), 2.58(3H, s), |

TABLE 127-continued

| | $^1$H-NMR δ ppm |
|---|---|
| | 2.63(2H, q, J=7.6Hz), 3.77(1H, dd, J=3.6Hz, 10,9Hz), 3.91(1H, dd, J=3.6Hz, 10.9Hz), 4.4–4.5(1H, s), 5.39(2H, s) 6.61(1H, s), 7.69(1H, s), 7.75(1H, d, J=7.6Hz), 8.03(1H, dd, J=1.0Hz, 7.6Hz), 8.11(1H, dd, J=7.6Hz, 7.6Hz), 8.63(1H, d, J=8.3Hz), 12.55(1H, s) |

TABLE 128

| Ex. No. | Structural formula |
|---|---|
| 184 | [Structure: ethyl/acetyl/OH-substituted phenoxy-methyl pyridine carboxamide linked to amino acid with SMe side chain] |
| 185 | [Structure: ethyl/acetyl/OH-substituted phenoxy-methyl pyridine carboxamide linked to phenylalanine] |
| 186 | [Structure: ethyl/acetyl/OH-substituted phenoxy-methyl pyridine carboxamide linked to tyrosine] |
| 187 | [Structure: ethyl/acetyl/OH-substituted phenoxy-methyl pyridine carboxamide linked to histidine] |
| 188 | [Structure: ethyl/acetyl/OH-substituted phenoxy-methyl pyridine carboxamide linked to alanine] |

TABLE 129

| | $^1$H-NMR δ ppm |
|---|---|
| 184 | (solvent:d$_6$-DMSO) 1.18(3H, t, J=7.6Hz), 2.04(3H, s), 2.1–2.2(2H, m), 2.4–2.5(2H, m), 2.58(3H, s), 2.62(2H, q, J=7.6Hz), 4.5–4.6(1H, m), 5.40(2H, s), 6.60(1H, s), 7.69(1H, s), 7.74(1H, d, J=7.6Hz), 7.99(1H, d, J=6.6Hz), 8.09(1H, dd, J=6.6Hz, 7.6Hz), 8.74(1H, d, J=8.2Hz), 12.55 (1H, s) |
| 185 | (solvent:d$_6$-DMSO) 1.16(3H, t, J=7.6Hz), 2.59(3H, s), 2.63(2H, q, J=7.6Hz), 3.1–3.4(2H, m), 4.6–4.7(1H, m), 5.34 (2H, s), 6.60(1H, s), 7.1–7.3(5H, m), 7.68(1H, s), 7.71(1H, d, J=7.6Hz), 7.97(1H, dd, J=1.0Hz, 8.07(1H, dd, J= 7.6Hz, 7.6Hz), 8.61(1H, d, J=8.2Hz), 12.56(1H, s) |
| 186 | (solvent:d$_6$-DMSO) 1.17(3H, t, J=7.6Hz), 2.58(3H, s), 2.61 |

TABLE 129-continued

| | ¹H-NMR δ ppm |
|---|---|
| | (2H, q, J=7.6Hz), 3.5–3.6(2H, m), 4.6–4.7(1H, m), 5.36(1H, s), 6.62(2H, d, J=8.5Hz), 6.99(2H, d, J=8.5Hz), 7.69(1H, s), 7.73(1H, dd, J=1.0Hz, 7.6Hz), 7.96(1H, dd, J=1.0Hz, 7.6Hz) 8.08(1H, dd, J=7.6Hz, 7.6Hz), 8.52(1H, d, J=8.3Hz), 9.21(1H, br), 12.56(1H, s) |
| 187 | (solvent:d₆-DMSO) 1.17(3H, t, J=7.6Hz), 2.58(3H, s), 2.62(2H, q, J=7.6Hz), 3.20(2H, d, J=6.3Hz), 4.7–4.8(1H, m), 5.37(2H, s), 6.60(1H, s), 7.12(1H, s), 7.69(1H, s), 7.72(1H, d, J=7.6Hz), 7.98(1H, dd, J=0.7Hz, 7.6Hz) 8.08(1H, dd, J=7.6Hz, 7.6Hz), 8.28(1H, s) 8.99(1H, d, J=8.3Hz), 12.54(1H, br), |
| 188 | (solvent:d₆-DMSO) 1.89(3H, t, J=7.6Hz), 1.43(3H, d, J=7.3Hz), 2.58(3H, s), 2.63(2H, q, J=7.6Hz), 4.4–4.5(1H, m), 5.39(2H, s), 6.59(1H, s), 7.69(1H, s), 7.73(1H, d, J=7.6Hz), 8.00(1H, d, J=7.6Hz), 8.09(1H, dd, J=7.6Hz, 7.6Hz), 8.67(1H, d, J=7.9Hz), 12.55(1H, s) |

TABLE 130

| Ex. No. | Structural formula |
|---|---|
| 189 | |
| 190 | |
| 191 | |
| 192 | |
| 193 | |

TABLE 131

| | ¹H-NMR δ ppm |
|---|---|
| 189 | (solvent:d₆-DMSO) 1.89(3H, t, J=7.6Hz), 1.43(3H, d, J= |

TABLE 131-continued

| | ¹H-NMR δ ppm |
|---|---|
| | 7.3Hz), 2.58(3H, s), 2.63(2H, q, J=7.6Hz), 4.4–4.5(1H, m), 5.39(2H, s), 6.59(1H, s), 7.69(1H, s), 7.73(1H, d, J=7.6Hz), 8.00(1H, d, J=7.6Hz), 8.09(1H, dd, J=7.6Hz, 7.6Hz), 8.67(1H, d, J=7.9Hz), 12.55(1H, s) |
| 190 | (solvent:d₆-DMSO) 1.86(3H, t, J=7.6Hz), 1.9-2.3(4H, m), 2.58(3H, s), 2.63(2H, q, J=7.6Hz), 4.4–4.5(1H, m), 5.40(2H, s), 6.60(1H, s), 7.69(1H, s), 7.73(1H, d, J=7.6Hz), 8.00(1H, d, J=7.6Hz), 8.10(1H, dd, J=7.6Hz, 7.6Hz), 8.70(1H, d, J=8.6Hz), 12.55(1H, s) |
| 191 | (solvent:d₆-DMSO) 1.19(3H, t, J=7.6Hz), 2.58(3H, s), 2.63(2H, q, J=7.6Hz), 3.60(2H, s), 4.24(2H, d, J=5.9Hz), 5.38(2H, s), 6.58(1H, s), 6.96(1H, s), 7.70(1H, s), 7.75(1H, d, J=7.6Hz), 8.02(1H, d, J=7.6Hz), 8.10(1H, dd, J=7.6Hz, 7.6Hz), 8.98(1H, d, J=5.9Hz), 12.34(1H, br), 12.55(1H, s) |
| 192 | (solvent:d₆-DMSO) 1.17(3H, t, J=7.6Hz), 2.58(3H, s), 2.62(2H, q, J=7.6Hz), 2.88(1H, dd, J=6.3Hz, 16.2Hz), 4.0–4.2(1H, m), 5.39(2H, s), 5.4–5.5(1H, m), 6.60(1H, s), 7.2–7.7(5H, m), 7.69(1H, s), 7.72(1H, d, J=7.6Hz), 7.98(1H, d, J=7.3Hz), 8.07(1H, dd, J=7.3Hz, 7.6Hz), 9.13(1H, d, J=8.9Hz), 12.32(1H, br), 12.56(1H, s) |
| 193 | (solvent:d₆-DMSO) 1.18(3H, t, J=7.6Hz), 1.7–1.8(2H, m), 2.26(2H, t, J=7.6Hz), 2.58(3H, s), 2.62(2H, q, J=7.6Hz), |

TABLE 131-continued

| ¹H-NMR δ ppm |
|---|
| 3.3–3.5(2H, m), 5.36(2H, s), 6.57(1H, s), 7.69(1H, s), 7.70(1H, d, J=7.6Hz), 7.98(1H, d, J=7.6Hz), 8.06(1H, dd, J=7.6Hz, 7.6Hz), 8.68(1H, d, J=5.6Hz), 12.00 (1H, br), 12.55(1H, br) |

TABLE 133-continued

| | ¹H-NMR δ ppm |
|---|---|
| | 7.80(1H, d, J=7.6Hz), 7.90(1H, s) |
| 197 | (solvent:CD₃OD:CDCl₃=1:4) 1.22(3H, td, J=7.6, 0.9Hz), 2.65(2H, q, J=7.6Hz), 2.98(1H, dd, J=17.2, 5.0Hz), 3.11 (1H, dd, J=17.5, 5.0Hz), 4.99(1H, dt, J=4.3, 8.6Hz), 5.18 (2H, s), 6.47(1H, s), 7.51(1H, dd, J=7.6, 8.3Hz), 7.63(1H, d, J=8.3Hz), 7.81(1H, d, J=7.6Hz), 7.92(1H, s), 2.59(3H, s), |

TABLE 132

| Ex. No. | Structural formula |
|---|---|
| 194 | 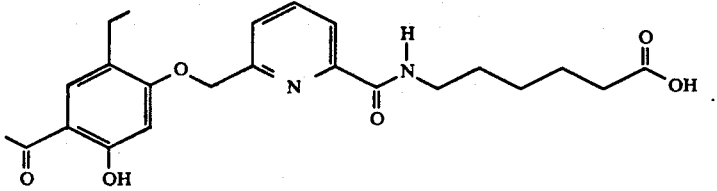 |
| 195 | 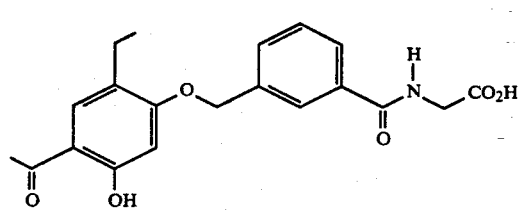 |
| 196 | 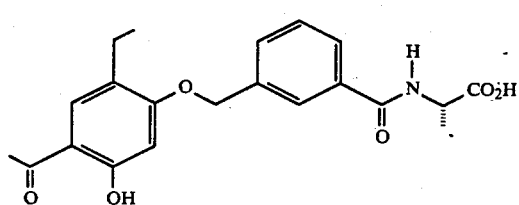 |
| 197 | 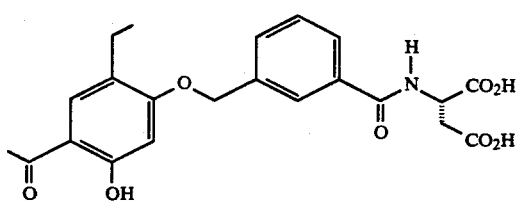 |
| 198 | 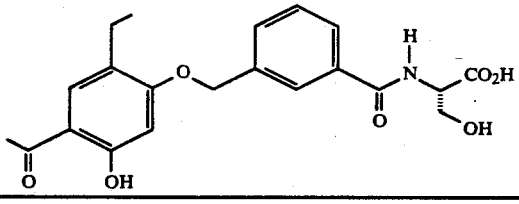 |

TABLE 133

| | ¹H-NMR δ ppm |
|---|---|
| 194 | (solvent:DMSO-d₆) 1.18(3H, t, J=7.6Hz), 1.2–1.3(2H, m), 1.5–1.7(4H, m), 2.21(2H, t, J=7.3Hz), 2.58(3H, s), 2.62(2H, q, J=7.6Hz), 5.36(2H, s), 6.57(1H, s), 7.68(1H, d, J=7.6Hz), 7.69(1H, s), 7.98(1H, d, J=7.6Hz), 8.06(1H, dd, J=7.6Hz, 7.6Hz), 8.61(1H, m), 12.55(1H, br) |
| 195 | (solvent:CD₃OD/CDCl₃(1/4)) 1.21(3H, t, J=7.6Hz), 2.58 (3H, s), 2.64(2H, q, J=7.6Hz), 4.18(2H, d, J=1.7Hz), 5.16 (2H, s), 6.46(1H, s), 7.49(1H, s), 7.50(1H, dd, J=7.6, 7.6Hz), 7.61(1H, d, J=7.6Hz), 7.81(1H, d, J=7.6Hz), 7.91(1H, s), 7.51(1H, s) |
| 196 | (solvent:CD₃OD:CDCl₃=1:4) 1.22(3H, t, J=7.4Hz), 1.55(3H, d, J=6.9Hz), 2.58(3H, s), 2.64(2H, q, J=7.4Hz), 4.72(1H, td, J=5.9, 7.3Hz), 5.17(2H, s), 6.46(1H, s), 7.50(1H, dd, J=7.9, 7.6Hz), 7.61(1H, d, J=7.9Hz), |
| 198 | (solvent:CD₃OD:CDCl₃=1:4) 1.22(3H, t, J=7.4Hz), 2.58 (3H, s), 2.64(2H, q, J=7.4Hz), 3.97(1H, dd, J=11.6, 3.5Hz), 4.10(1H, dd, J=11.2, 3.9Hz), 4.67(1H, t, J=3.6Hz), 5.17(1H, s), 6.46(1H, s), 7.50(1H, s), 7.51(1H, dd, J=7.6, 7.6Hz), 7.62(1H, d, J=7.6Hz), 7.85(1H, d, J=7.6Hz) |

TABLE 134

| Ex. No. | Structural formula |
|---|---|
| 199 | 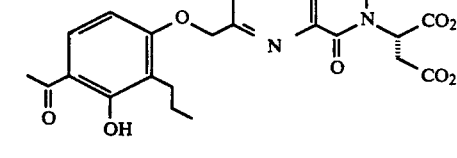 |
| 200 | |
| 201 | |
| 202 | |
| 203 | |

TABLE 135

¹H-NMR δ ppm 199 (solvent:CD₃OD/CDCl₃(1/4)) 0.99(3H, t, J=7.6Hz), 1.5–1.7(2H, m), 2.60(3H, s), 2.70(2H, t, J=7.8Hz), 3.0–3.3(2H, m), 5.1–5.2(1H, m), 5.27(2H, s), 6.76(2H, d, J=8.9Hz), 7.53 (2H, d, J=8.9Hz), 7.64(1H, d, J=7.9Hz), 7.90(1H, dd, J=7.9, 7.6Hz), 8.11(1H, d, J=7.6Hz)

200 (solvent:CD₃OD/CDCl₃(1/4)) 0.98(3H, t, J=7.3Hz), 1.5–1.7(2H, m), 2.57(3H, s), 2.75(2H, t, J=7.6Hz), 3.0–3.3(2H, m), 3.75(3H, s), 5.1–5.2(1H, m), 5.31(2H, s), 6.50(1H, d, J=8.9Hz), 7.60(1H, d, J=8.9Hz), 7.67(1H, d, J=7.6Hz), 7.92(1H, dd, J=7.6, 7.3Hz), 8.14(1H, d, J=7.3Hz)

201 (solvent:CD₃OD/CDCl₃(1/4)) 1.01(3H, t, J=7.3Hz), 1.63(3H, d, J=7.3Hz), 1.5–1.7(2H, m), 2.62(3H, s), 2.74(2H, t, J=7.6Hz), 3.78(3H, s), 4.80(1H, t, J=7.3Hz), 5.29(2H, s), 6.73(1H, d, J=8.9Hz), 7.55(1H, d, J=8.9Hz), 7.66(1H, d, J=7.6Hz), 7.93(1H, dd, J=7.6, 7.6Hz), 8.15(1H, d, J=7.6Hz)

202 (solvent:CD₃OD/CDCl₃(1/4)) 1.23(3H, t, J=7.4Hz), 1.62(3H, d, J=7.3Hz), 2.58(3H, s), 2.69(2H, q, J=7.4Hz), 3.87(3H, s), 4.82(1H, q, J=7.3, 7.3Hz), 5.31(2H, s), 6.49(1H, s), 7.71(1H, d, J=7.9Hz), 7.71(1H, s), 7.94(1H, dd, J=7.6, 7.9Hz), 8.16(1H, d, J=7.6Hz)

203 (solvent:CD₃OD/CDCl₃(1/4)) 1.24(3H, t, J=7.6Hz), 1.7–2.2(4H, m), 2.57(3H, s), 2.6–2.8(1H, m), 2.67(2H, q, J=7.6Hz), 3.0–3.3(2H, m), 3.8–4.0(1H, m), 4.4–4.6(1H, m), 5.25 (2H, s), 6.44(1H, s), 7.47(1H, s), 7.54(1H, d, J=7.6Hz), 7.57 (1H, d, J=7.0Hz), 7.85(1H, dd, J=7.6, 7.9Hz)

TABLE 136

| Ex. No. | Structural formula |
|---|---|
| 204 | 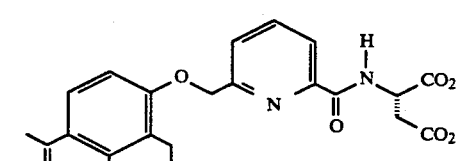 |
| 205 | |
| 206 | |
| 207 | |
| 208 | |

TABLE 137

¹H-NMR δ ppm 204 (solvent:CD₃OD/CDCl₃(1/4)) 1.25(3H, t, J=7.4Hz), 1.5–2.3(5H, m), 2.57(3H, s), 2.67(2H, q, J=7.4Hz), 2.7–2.9(1H, m), 3.1–4.8(4H, m), 5.25(2H, s), 6.44(1H, s), 7.47(1H, s), 7.5–7.7(2H, m), 7.85(1H, dd, J=7.6, 7.9Hz)

205 (solvent:CD₃OD/CDCl₃(1/4)) 1.24(3H, t, J=7.6Hz), 1.43(3H, d, J=6.6Hz), 2.58(3H, s), 2.67(2H, q, J=7.4Hz), 2.74(2H, dd, J=5.6, 3.0Hz), 4.5–4.6(1H, m), 5.25(2H, s), 6.51(1H, s), 7.48(1H, s), 7.61(1H, d, J=7.9Hz), 7.89(1H, dd, J=7.6, 7.9Hz), 8.14(1H, d, J=7.6Hz)

206 (solvent:CD₃OD/CDCl₃(1/4)) 1.2–1.3(6H, m), 2.57(1H, s), 2.67(2H, q, J=7.5Hz), 2.8–3.0(2H, m), 3.4–3.8(4H, m), 5.24 (2H, s), 6.4–6.5(1H, m), 7.48(1H, s), 7.5–7.7(2H, m), 7.85(1H, dd, J=7.6, 7.9Hz)

207 (solvent:CD₃OD/CDCl₃(1/9)) 1.25(3H, t, J=7.4Hz), 1.29(3H, d, J=6.3Hz), 2.58(3H, s), 2.69(2H, q, J=7.4Hz),

TABLE 137-continued

| | $^1$H-NMR δ ppm |
|---|---|
| | 4.4–4.6(1H, m), 4.7–4.9(1H, m), 5.30(2H, s), 6.50(1H, s), 7.50(1H, s), 7.66(1H, d, J=7.6Hz), 7.93(1H, dd, J=7.6, 7.6Hz), 8.13(1H, d, J=7.6Hz) |
| 208 | (solvent:CD$_3$OD/CDCl$_3$(1/9)) 1.23(1.2H, t, J=7.6Hz), 1.26(1.8H, t, J=7.6Hz), 2.1–2.6(2H, m), 2.59(3H, s), 2.8–3.0(2H, m), 3.8–4.8(3H, m), 5.3–5.4(3H, m), 6.44(0.6H, s), 6.48(0.4H, s), 7.5–8.1(3H, s), |

TABLE 138

| Ex. No. | Structural formula |
|---|---|
| 209 | |
| 210 | |
| 211 | |
| 212 | |
| 213 | |

TABLE 139

| | $^1$H-NMR δ ppm |
|---|---|
| 209 | (solvent:CDCl$_3$/MeOD(9/1)) 1.26(3H, t, J=7.4Hz), 1.9–2.1(1H, m), 2.2–2.4(1H, m), 2.59(3H, s), 2.70(1H, q, J=7.4Hz), 3.6–3.9(1H, m), 4.84(1H, dt, J=4.3, 4.6Hz), 5.30(2H, s), 6.49(1H, s), 7.53(1H, s), 7.69(1H, d, J=7.6Hz), 7.96(1H, dd, J=7.6, 7.6Hz), 8.11(1H, d, J=7.6Hz) |
| 210 | (solvent:DMSO-d$_6$) 1.19(3H, t, J=7.6Hz), 2.57(3H, s), 2.63(2H, q, J=7.6Hz), 3.78(2H, s), 4.02(2H, s), 5.36(2H, s), 6.56(1H, s), 7.67(1H, s), 7.71(1H, d, J=7.3Hz), 8.03(1H, dd, J=6.6, 5.9Hz), 8.09(1H, d, J=6.6Hz), |
| 211 | (solvent:CDCl$_3$/MeOD(4/1)) 1.26(3H, t, J=7.6Hz), 1.29(3H, t, J=7.3Hz), 2.59(3H, s), 2.69(2H, q, J=7.5Hz), 3.68(2H, s), 4.05(2H, s), 4.20(2H, q, J=7.3Hz), 5.29(2H, s), 6.46(1H, s), 7.52(1H, s), 7.67(1H, d, J=7.9Hz), 7.95(1H, dd, J=7.6, 7.9Hz), 8.11(1H, d, J=7.6Hz) |
| 212 | (solvent:DMSO-d$_6$) 1.25(3H, t, J=7.6Hz), 2.58(3H, s), 2.68(2H, q, J=7.6Hz), 3.50(1H, m), 3.78(1H, m), 4.74(1H, m), 5.30(2H, s), 5.46(1H, d, J=2.0Hz), 6.49(1H, s), 6.69(1H, m), 6.85(1H, d, J=7.9Hz), 6.91(1H, s), 7.13(1H, t, J=7.9Hz), 7.56(1H, s), 7.67(1H, d, J=7.6Hz), 7.98(1H, t, J=7.6Hz), 8.08(1H, d, J=7.6Hz), 8.51(1H, m), 9.08(1H, s), 12.61(1H, s) |
| 213 | (solvent:DMSO-d$_6$) 1.19(3H, t, J=7.6Hz), 2.58(3H, s), 2.64(2H, q, J=7.6Hz), 3.85(2H, m), 4.55(1H, m), 5.34(1H, br), 5.39(2H, s), 6.60(1H, s), 7.68(1H, s), 7.74(1H, d, J=7.6Hz), 8.05(1H, t, J=7.6Hz), 8.12(1H, d, J=7.6Hz), 8.63(1H, d, J=8.3Hz), 12.55(1H, s), 12.90(1H, br) |

TABLE 140

| Ex. No. | Structural formula |
|---|---|
| 214 | (structure) |
| 215 | (structure) |
| 216 | (structure) |
| 217 | (structure) |
| 218 | (structure) |

TABLE 141

$^1$H-NMR δ ppm 214 (solvent:CDCl$_3$) 1.25(3H, t, J=7.6Hz), 2.58(3H, s), 2.68(2H, q, J=7.6Hz), 3.85(3H, s), 4.11(2H, m), 4.88(1H, m), 5.29(2H, s), 6.52(1H, s), 7.49(1H, s), 7.65(1H, d, J=8.3Hz), 7.91(1H, t, J=8.3Hz), 8.15(1H, d, J=8.3Hz), 8.80 (1H, d, J=8.3Hz) 12.69(1H, s)

215 (solvent:DMSO-d$_6$) 1.18(3H, t, J=7.3Hz), 2.51(3H, s), 2.63(2H, q, J=7.3Hz), 3.79(1H, dd, J=11.2Hz, 3.9Hz), 3.91(1H, dd, J=11.2Hz, 3.9Hz), 4.55(1H, m), 5.48(2H, s), 6.68(1H, s), 7.70(1H, s), 8.58(1H, d, J=7.9Hz), 9.05(1H, s), 9.21(1H, s), 12.57(1H, s)

216 (solvent:CDCl$_3$) 1.27(3H, t, J=7.3Hz), 2.59(3H, br), 2.89(3H, s), 2.68(2H, q, J=7.3Hz), 3.85(3H, s), 4.06(1H, dd, J=11.2Hz, 3.6Hz), 4.18(1H, dd, J=11.2Hz, 3.6Hz), 4.90(1H, m), 5.34(2H, s), 6.52(1H, s), 7.51(1H, s), 8.58(1H, m), 9.00(1H, s), 9.37(1H, s), 12.71(1H, s), 217 (solvent:CDCl$_3$) 1.27(3H, t, J=7.6Hz), 2.60(3H, s), 2.71(2H, q, J=7.6Hz), 3.79(2H, s), 3.85-4.10(4H, m), 4.64-4.80(2H, m), 5.33(2H, s), 6.49(1H, s), 7.57(1H, s), 7.72(1H, d, J=7.6Hz), 8.00(1H, t, J=7.6Hz), 8.10(1H, d, J=7.6Hz)

218 (solvent:CDCl$_3$) 1.25(3H, t, J=7.6Hz), 2.57(3H, s), 2.67(2H, q, J=7.6Hz), 3.2-3.7(2H, m), 3.70(s, 1.2H), 3.81(s, 1.8H), 4.0-4.3(2H, m), 4.37(0.6H, m), 4.90(0.4H, m), 5.24 (2H, s), 6.44(1H, s), 7.48(1H, s), 7.5-7.9(3H, m), 12.63(1H, s)

TABLE 142

| Ex. No. | Structural formula |
|---|---|
| 219 | 4'-acetyl-2'-ethyl-phenoxymethyl-pyridine-2-carboxamide with 2-amino-2-ethyl-1,3-propanediol substituent |
| 220 | 4'-acetyl-2'-ethyl-phenoxymethyl-pyridine-2-carboxamide with 2-amino-2-methyl-1,3-propanediol substituent |
| 221 | 4'-acetyl-2'-ethyl-phenoxymethyl-pyridine-2-carboxamide with tris(hydroxymethyl)aminomethane substituent |
| 222 | 4'-acetyl-2'-ethyl-phenoxymethyl-pyridine-2-carboxamide with 2-amino-1,3-propanediol substituent |
| 223 | 4'-acetyl-2'-ethyl-phenoxymethyl-pyridine-2-carboxamide with serylglycine substituent |

TABLE 143

$^1$H-NMR δ ppm 219 (solvent:CDCl$_3$) 1.00(3H, t, J=7.6Hz), 1.24(3H, t, J=7.6Hz), 1.81(2H, q, J=7.6Hz), 2.58(3H, s), 2.67(2H, q, J=7.6Hz), 3.72(2H, m), 3.94–4.06(4H, m), 5.27(2H, s), 6.56(1H, s), 7.48(1H, s), 7.63(1H, d, J=7.6Hz), 7.93(1H, t, J=7.6Hz), 8.15(1H, d, J=7.6Hz), 8.52(1H, brs), 12.73(1H, s), 220 (solvent:CDCl$_3$) 1.24(3H, t, J=7.3Hz), 1.38(3H, s), 2.58(3H, s), 2.67(2H, q, J=7.3Hz), 3.7–4.1(6H, m), 5.27(2H, s), 6.56 (1H, s), 7.48(1H, s), 7.64(1H, d, J=7.6Hz), 7.92(1H, t, J=7.6Hz), 8.14(1H, d, J=7.6Hz), 8.49(1H, s), 12.73(1H, s)

221 (solvent:CDCl$_3$) 1.22(3H, t, J=7.6Hz), 2.57(3H, s), 2.65(2H, q, J=7.6Hz), 3.83(8H, s), 5.29(2H, s), 6.66(1H, s), 7.46(1H, s), 7.65(1H, d, J=6.6Hz), 7.93(1H, t, J=7.6Hz), 8.14(1H, d, J=7.9Hz), 9.12(1H, s), 12.82(1H, s)

222 (solvent:CDCl$_3$) 1.26(3H, t, J=7.6Hz), 2.58(3H, s), 2.67–2.72(2H, m), 3.75–3.82(2H, m), 3.83–3.95(2H, m), 4.14–4.20(1H, m), 4.20–4.26(2H, m), 5.27(2H, s), 6.45(1H, s), 7.50(1H, s), 7.62(1H, d, J=6.9Hz), 7.92(1H, t, J=6.9Hz), 8.13(1H, d, J=6.9Hz), 8.53(1H, d, J=7.9Hz), 12.66(1H, s)

223 (solvent:DMSO-d$_6$) 1.21(3H, t, J=7.6Hz), 2.58(3H, s), 2.65(2H, q, J=7.6Hz), 3.7–3.9(4H, m), 4.61(1H, m), 5.05(1H, br), 5.37(2H, s), 6.58(1H, s), 7.65(1H, s), 7.71(1H, dd, J=6.8Hz, 2.1Hz), 8.02–8.25(2H, m), 8.39(1H, t, J=5.8Hz), 8.62(1H, d, J=8.3Hz), 12.54(1H, s),

TABLE 144

| Ex. No. | Structural formula |
|---|---|
| 224 | ![structure 224] |
| 225 | ![structure 225] |
| 226 | ![structure 226] |

TABLE 145

¹H-NMR δ ppm 224 (solvent:DMSO-d₆) 1.21(3H, t, J=7.6Hz), 2.57(3H, s), 2.64(2H, q, J=7.6Hz), 3.54(1H, m), 3.72(1H, m), 4.19(1H, m), 5.34(2H, s), 5.59(1H, br), 6.55(1H, s), 7.63(1H, s), 7.69(1H, dd, J=6.1Hz, 2.8Hz), 8.05(2H, m), 8.51(1H, t, J=6.1Hz), 12.55(1H, s), 12.65(1H, br)

225 (solvent:CDCl₃) 1.25(3H, t, J=7.6Hz), 1.26(3H, t, J=7.3Hz), 2.58(3H, s), 2.68(2H, q, J=7.6Hz), 3.10(1H, dd, J=8.9Hz, 5.6Hz), 3.80–3.88(1H, m), 4.06(2H, d, J=5.6Hz), 4.20 (2H, qJ=7.3Hz), 4.25, 4.35(1H, m), 4.70(1H, m), 5.28(2H, s), 6.45(1H, s), 7.15(1H, br), 7.49(1H, s), 7.63(1H, d, J=6.9Hz), 7.92(1H, t, J=6.9Hz), 8.15(1H, d, J=6.9Hz), 8.85 (1H, d, J=7.6Hz), 12.66(1H, s)

226 (solvent:CDCl₃) 1.25(3H, t, J=7.6Hz), 2.58(3H, s), 2.68(2H, q, J=7.6Hz), 3.57(1H, d, J=5.3Hz), 3.83(3H, s), 3.88(2H, m), 4.44(1H, m), 5.25(2H, s), 6.47(1H, s), 7.49(1H, s), 7.63(1H, d, J=7.6Hz), 7.91(1H, t, J=7.6Hz), 8.14(1H, d, J=7.6Hz), 8.36(1H, br), 12.68(1H, s)

What is claimed is:

1. A compound represented by the formula:

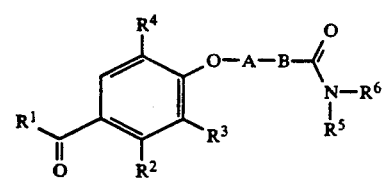

wherein
A is a $C_1$–$C_5$ alkylene chain;
B is a pyridinediyl group;
$R^1$ is a $C_1$–$C_5$ alkyl group;
$R^2$ is a hydroxyl group or a $C_1$–$C_5$ alkoxy group;
$R^3$ and $R^4$ are each independently a hydrogen atom, a $C_1$–$C_5$ alkyl group, a $C_2$–$C_5$ alkenyl group or a $C_2$–$C_5$ alkynyl group;
$R^5$ is a hydrogen atom, a $C_1$–$C_5$ alkyl group or a hydroxy $C_1$–$C_5$ alkyl group;
$R^6$ is a $CHR^{20}(CH_2)_n COOR^7$ group, wherein $R^7$ and $R^{20}$ are each a hydrogen atom and n is 0, 1, 2, 3, 4, or 5;
and pharmaceutically acceptable salts thereof.

2. A compound according to claim 1, wherein $R^1$ is a methyl group and $R^2$ is a hydroxyl group.

3. A compound according to claim 1, wherein $R^3$ is a hydrogen atom and A is a methylene group.

4. A compound according to claim 1, wherein $R^1$ is a methyl group, $R^2$ is a hydroxyl group, $R^3$ is a hydrogen atom and A is a methylene group.

5. A compound according to claim 4, wherein $R^4$ is an ethyl group.

6. A compound according to claim 1, wherein $R^6$ is a —$CH_2CH_2CO_2H$ group.

7. A compound according to claim 4, wherein $R^6$ is a —$CH_2CH_2CO_2H$ group.

8. A compound according to claim 1, which has the formula:

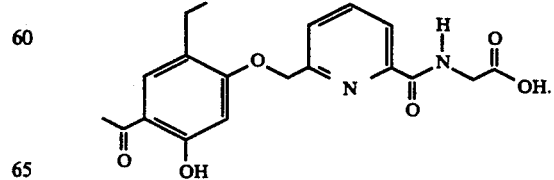

9. A compound according to claim 1, which has the formula:

10. A compound according to claim 1, which has the formula:

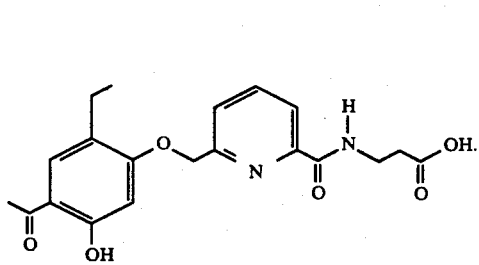

11. A compound according to claim 1, which has the formula:

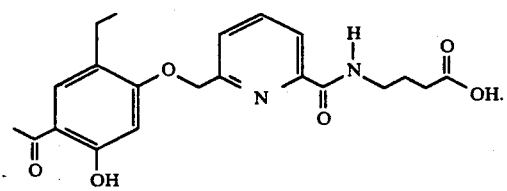

12. A compound according to claim 1, which has the formula:

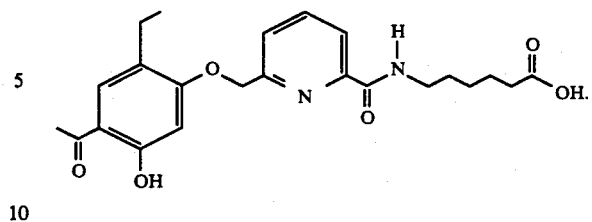

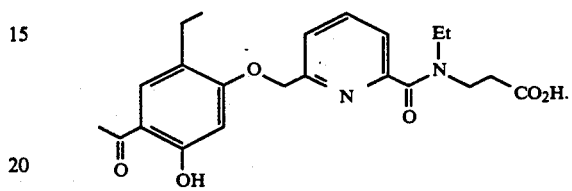

13. A pharmaceutical composition useful as an antiinflammatory agent or an antiallergic agent, which comprises an effective amount of a compound of claim 1 or a pharmaceutically acceptable salt thereof as an active ingredient and a pharmaceutically acceptable carrier or diluent.

14. A method of treating inflammatory or allergic states which comprises administering a pharmaceutically effective amount of a compound of claim 1 or a pharmaceutically acceptable salt thereof to a patient.

15. A compound according to claim 5, wherein $R^6$ is a —$CH_2CH_2CO_2H$ group.

* * * * *